(12) United States Patent
Benjamin et al.

(10) Patent No.: US 7,794,057 B2
(45) Date of Patent: Sep. 14, 2010

(54) FLUID EJECTION DEVICE

(75) Inventors: Trudy L. Benjamin, Portland, OR (US);
James P Axtell, Portland, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 43 days.

(21) Appl. No.: 12/150,160

(22) Filed: Apr. 25, 2008

(65) Prior Publication Data

US 2008/0204493 A1 Aug. 28, 2008

Related U.S. Application Data

(62) Division of application No. 10/827,163, filed on Apr. 19, 2004, now Pat. No. 7,384,113.

(51) Int. Cl.
*B41J 2/05* (2006.01)

(52) U.S. Cl. .................. 347/57; 347/5; 347/12

(58) Field of Classification Search ........ 347/5, 347/9, 10–12, 57, 13, 40; 358/296
See application file for complete search history.

(56) References Cited

U.S. PATENT DOCUMENTS

| | | | |
|---|---|---|---|
| 5,541,629 A | 7/1996 | Saunders et al. | |
| 5,608,431 A * | 3/1997 | Kishida et al. | 347/13 |
| 5,621,440 A | 4/1997 | Takahashi | |
| 5,629,771 A * | 5/1997 | Mikami | 358/296 |
| 5,648,804 A | 7/1997 | Keefe et al. | |
| 5,757,394 A | 5/1998 | Gibson et al. | |
| 6,022,094 A | 2/2000 | Gibson et al. | |
| 6,036,297 A | 3/2000 | Hayasaki | |
| 6,176,569 B1 | 1/2001 | Anderson et al. | |
| 6,270,180 B1 | 8/2001 | Arakawa et al. | |
| 6,318,828 B1 | 11/2001 | Barbour et al. | |
| 6,398,347 B1 | 6/2002 | Torgerson et al. | |
| 6,402,279 B1 | 6/2002 | Torgerson et al. | |
| 6,422,676 B1 | 7/2002 | Torgerson et al. | |
| 6,476,839 B1 | 11/2002 | Nakajima et al. | |
| 6,491,377 B1 | 12/2002 | Cleland et al. | |
| 6,536,877 B2 | 3/2003 | Miyamoto et al. | |
| 6,540,333 B2 | 4/2003 | Axtell et al. | |
| 6,543,883 B1 | 4/2003 | Dodd et al. | |
| 6,582,062 B1 | 6/2003 | Childers et al. | |
| 2001/0012032 A1 | 8/2001 | Kawamura et al. | |
| 2002/0060722 A1 | 5/2002 | Axtell et al. | |
| 2002/0140772 A1 | 10/2002 | Torgerson et al. | |
| 2002/0140779 A1 | 10/2002 | Torgerson et al. | |
| 2002/0180839 A1 | 12/2002 | Torgerson et al. | |
| 2002/0186265 A1 | 12/2002 | Schloeman et al. | |
| 2003/0063161 A1 | 4/2003 | Dodd et al. | |
| 2003/0189608 A1 | 10/2003 | Hung et al. | |

FOREIGN PATENT DOCUMENTS

| | | |
|---|---|---|
| EP | 0405574 | 1/1991 |
| EP | 1072412 | 1/2001 |
| EP | 1080903 | 3/2001 |

* cited by examiner

*Primary Examiner*—Lam S Nguyen

(57) ABSTRACT

A fluid ejection device having firing cells, signal lines configured to receive a series of pulses, and an address generator configured to receive pulses from the series of pulses and generate a set of address signals in response to the received pulses, wherein the set of address signals is adapted to enable the firing cells for activation.

17 Claims, 24 Drawing Sheets

FLUID EJECTION DEVICE

CROSS-REFERENCE TO RELATED APPLICATIONS

This application is a divisional of the U.S. application Ser. No. 10/827,163, filed on Apr. 19, 2004, now U.S. Pat. No. 7,384,113 entitled "Fluid Ejection Device With Address Generator", by Benjamin et al., which is assigned to the assignee of the present invention and hereby incorporated by reference herein in its entirety.

BACKGROUND

An inkjet printing system, as one embodiment of a fluid ejection system, may include a printhead, an ink supply that provides liquid ink to the printhead, and an electronic controller that controls the printhead. The printhead, as one embodiment of a fluid ejection device, ejects ink drops through a plurality of orifices or nozzles. The ink is projected toward a print medium, such as a sheet of paper, to print an image onto the print medium. The nozzles are typically arranged in one or more arrays, such that properly sequenced ejection of ink from the nozzles causes characters or other images to be printed on the print medium as the printhead and the print medium are moved relative to each other.

In a typical thermal inkjet printing system, the printhead ejects ink drops through nozzles by rapidly heating small volumes of ink located in vaporization chambers. The ink is heated with small electric heaters, such as thin film resistors referred to herein as firing resistors. Heating the ink causes the ink to vaporize and be ejected through the nozzles.

To eject one drop of ink, the electronic controller that controls the printhead activates an electrical current from a power supply external to the printhead. The electrical current is passed through a selected firing resistor to heat the ink in a corresponding selected vaporization chamber and eject the ink through a corresponding nozzle. Known drop generators include a firing resistor, a corresponding vaporization chamber, and a corresponding nozzle.

As inkjet printheads have evolved, the number of drop generators in a printhead has increased to improve printing speed and/or quality. The increase in the number of drop generators per printhead has resulted in a corresponding increase in the number of input pads required on a printhead die to energize the increased number of firing resistors. In one type of printhead, each firing resistor is coupled to a corresponding input pad to provide power to energize the firing resistor. One input pad per firing resistor becomes impractical as the number of firing resistors increases.

The number of drop generators per input pad is significantly increased in another type of printhead having primitives. A single power lead provides power to all firing resistors in one primitive. Each firing resistor is coupled in series with the power lead and the drain-source path of a corresponding field effect transistor (FET). The gate of each FET in a primitive is coupled to a separately energizable address lead that is shared by multiple primitives.

Manufacturers continue reducing the number of input pads and increasing the number of drop generators on a printhead die. A printhead with fewer input pads typically costs less than a printhead with more input pads. Also, a printhead with more drop generators typically prints with higher quality and/or printing speed. To maintain costs and provide a particular printing swath height, printhead die size may not significantly change with an increased number of drop generators. As drop generator densities increase and the number of input pads decrease, printhead die layouts can become increasingly complex.

For these and other reasons, there is a need for the present invention.

DETAILED DESCRIPTION

In the following detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
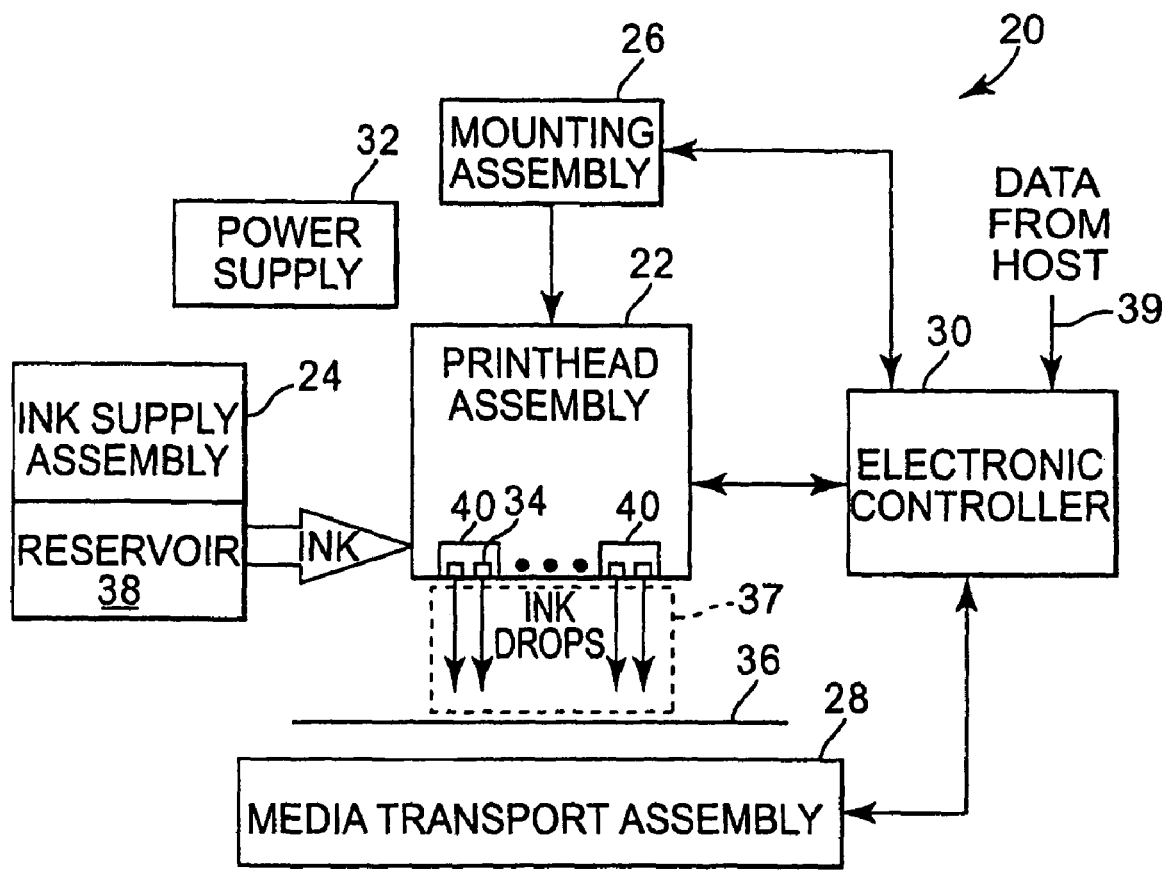
FIG. 1 illustrates one embodiment of an ink jet printing system.

FIG. 1 illustrates one embodiment of an inkjet printing system 20. Inkjet printing system 20 constitutes one embodiment of a fluid ejection system that includes a fluid ejection device, such as inkjet printhead assembly 22, and a fluid supply assembly, such as ink supply assembly 24. The inkjet printing system 20 also includes a mounting assembly 26, a media transport assembly 28, and an electronic controller 30. At least one power supply 32 provides power to the various electrical components of inkjet printing system 20.

In one embodiment, inkjet printhead assembly 22 includes at least one printhead or printhead die 40 that ejects drops of ink through a plurality of orifices or nozzles 34 toward a print medium 36 so as to print onto print medium 36. Printhead 40 is one embodiment of a fluid ejection device. Print medium 36 may be any type of suitable sheet material, such as paper, card stock, transparencies, Mylar, fabric, and the like. Typically, nozzles 34 are arranged in one or more columns or arrays such that properly sequenced ejection of ink from nozzles 34 causes characters, symbols, and/or other graphics or images to be printed upon print medium 36 as inkjet printhead assembly 22 and print medium 36 are moved relative to each other. While the following description refers to the ejection of ink from printhead assembly 22, it is understood that other liquids, fluids or flowable materials, including clear fluid, may be ejected from printhead assembly 22.

Ink supply assembly 24 as one embodiment of a fluid supply assembly provides ink to printhead assembly 22 and includes a reservoir 38 for storing ink. As such, ink flows from reservoir 38 to inkjet printhead assembly 22. Ink supply assembly 24 and inkjet printhead assembly 22 can form either a one-way ink delivery system or a recirculating ink delivery system. In a one-way ink delivery system, substantially all of the ink provided to inkjet printhead assembly 22 is consumed during printing. In a recirculating ink delivery system, only a portion of the ink provided to printhead assembly 22 is consumed during printing. As such, ink not consumed during printing is returned to ink supply assembly 24.

In one embodiment, inkjet printhead assembly 22 and ink supply assembly 24 are housed together in an inkjet cartridge or pen. The inkjet cartridge or pen is one embodiment of a fluid ejection device. In another embodiment, ink supply assembly 24 is separate from inkjet printhead assembly 22 and provides ink to inkjet printhead assembly 22 through an interface connection, such as a supply tube (not shown). In either embodiment, reservoir 38 of ink supply assembly 24 may be removed, replaced, and/or refilled. In one embodiment, where inkjet printhead assembly 22 and ink supply assembly 24 are housed together in an inkjet cartridge, reservoir 38 includes a local reservoir located within the cartridge and may also include a larger reservoir located separately from the cartridge. As such, the separate, larger reservoir serves to refill the local reservoir. Accordingly, the separate, larger reservoir and/or the local reservoir may be removed, replaced, and/or refilled.

Mounting assembly 26 positions inkjet printhead assembly 22 relative to media transport assembly 28 and media transport assembly 28 positions print medium 36 relative to inkjet printhead assembly 22. Thus, a print zone 37 is defined adjacent to nozzles 34 in an area between inkjet printhead assembly 22 and print medium 36. In one embodiment, inkjet printhead assembly 22 is a scanning type printhead assembly. As such, mounting assembly 26 includes a carriage (not shown) for moving inkjet printhead assembly 22 relative to media transport assembly 28 to scan print medium 36. In another embodiment, inkjet printhead assembly 22 is a non-scanning type printhead assembly. As such, mounting assembly 26 fixes inkjet printhead assembly 22 at a prescribed position relative to media transport assembly 28. Thus, media transport assembly 28 positions print medium 36 relative to inkjet printhead assembly 22.

Electronic controller or printer controller 30 typically includes a processor, firmware, and other electronics, or any combination thereof, for communicating with and controlling inkjet printhead assembly 22, mounting assembly 26, and media transport assembly 28. Electronic controller 30 receives data 39 from a host system, such as a computer, and usually includes memory for temporarily storing data 39. Typically, data 39 is sent to inkjet printing system 20 along an electronic, infrared, optical, or other information transfer path. Data 39 represents, for example, a document and/or file to be printed. As such, data 39 forms a print job for inkjet printing system 20 and includes one or more print job commands and/or command parameters.

In one embodiment, electronic controller 30 controls inkjet printhead assembly 22 for ejection of ink drops from nozzles 34. As such, electronic controller 30 defines a pattern of ejected ink drops that form characters, symbols, and/or other graphics or images on print medium 36. The pattern of ejected ink drops is determined by the print job commands and/or command parameters.

In one embodiment, inkjet printhead assembly 22 includes one printhead 40. In another embodiment, inkjet printhead assembly 22 is a wide-array or multi-head printhead assembly. In one wide-array embodiment, inkjet printhead assembly 22 includes a carrier, which carries printhead dies 40, provides electrical communication between printhead dies 40 and electronic controller 30, and provides fluidic communication between printhead dies 40 and ink supply assembly 24.

Figure 2:
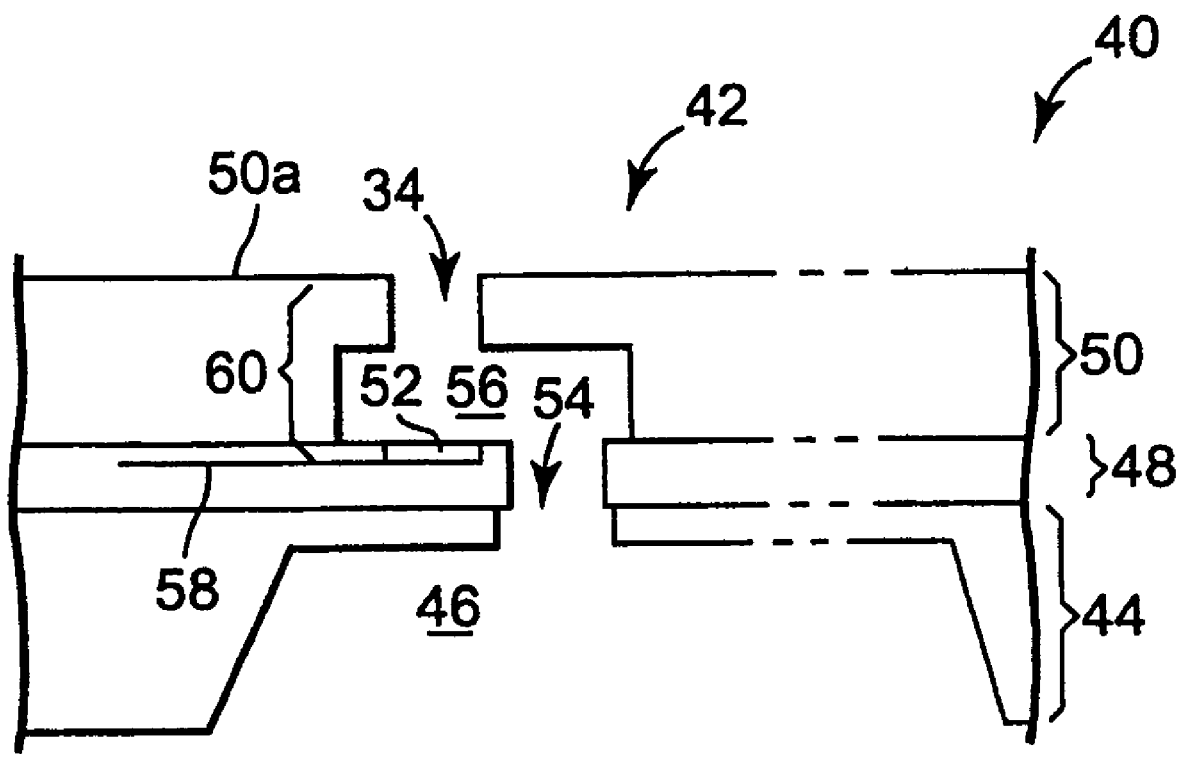
FIG. 2 is a diagram illustrating a portion of one embodiment of a printhead die.

FIG. 2 is a diagram illustrating a portion of one embodiment of a printhead die 40. The printhead die 40 includes an array of printing or fluid ejecting elements 42. Printing elements 42 are formed on a substrate 44, which has an ink feed slot 46 formed therein. As such, ink feed slot 46 provides a supply of liquid ink to printing elements 42. Ink feed slot 46 is one embodiment of a fluid feed source. Other embodiments of fluid feed sources include but are not limited to corresponding individual ink feed holes feeding corresponding vaporization chambers and multiple shorter ink feed trenches that each feed corresponding groups of fluid ejecting elements. A thin-film structure 48 has an ink feed channel 54 formed therein which communicates with ink feed slot 46 formed in substrate 44. An orifice layer 50 has a front face 50a and a nozzle opening 34 formed in front face 50a. Orifice layer 50 also has a nozzle chamber or vaporization chamber 56 formed therein which communicates with nozzle opening 34 and ink feed channel 54 of thin-film structure 48. A firing resistor 52 is positioned within vaporization chamber 56 and leads 58 electrically couple firing resistor 52 to circuitry controlling the application of electrical current through selected firing resistors. A drop generator 60 as referred to herein includes firing resistor 52, nozzle chamber or vaporization chamber 56 and nozzle opening 34.

During printing, ink flows from ink feed slot 46 to vaporization chamber 56 via ink feed channel 54. Nozzle opening 34 is operatively associated with firing resistor 52 such that droplets of ink within vaporization chamber 56 are ejected through nozzle opening 34 (e.g., substantially normal to the plane of firing resistor 52) and toward print medium 36 upon energizing of firing resistor 52.

Example embodiments of printhead dies 40 include a thermal printhead, a piezoelectric printhead, an electrostatic printhead, or any other type of fluid ejection device known in the art that can be integrated into a multi-layer structure. Substrate 44 is formed, for example, of silicon, glass, ceramic, or a stable polymer and thin-film structure 48 is formed to include one or more passivation or insulation layers of silicon dioxide, silicon carbide, silicon nitride, tantalum, polysilicon glass, or other suitable material. Thin-film structure 48, also, includes at least one conductive layer, which defines firing resistor 52 and leads 58. In one embodiment, the conductive layer comprises, for example, aluminum, gold, tantalum, tantalum-aluminum, or other metal or metal alloy. In one embodiment, firing cell circuitry, such as described in detail below, is implemented in substrate and thin-film layers, such as substrate 44 and thin-film structure 48.

In one embodiment, orifice layer 50 comprises a photoimageable epoxy resin, for example, an epoxy referred to as SU8, marketed by Micro-Chem, Newton, Mass. Exemplary techniques for fabricating orifice layer 50 with SU8 or other polymers are described in detail in U.S. Pat. No. 6,162,589, which is herein incorporated by reference. In one embodiment, orifice layer 50 is formed of two separate layers referred to as a barrier layer (e.g., a dry film photo resist barrier layer) and a metal orifice layer (e.g., a nickel, copper, iron/nickel alloys, palladium, gold, or rhodium layer) formed over the barrier layer. Other suitable materials, however, can be employed to form orifice layer 50.

Figure 3:
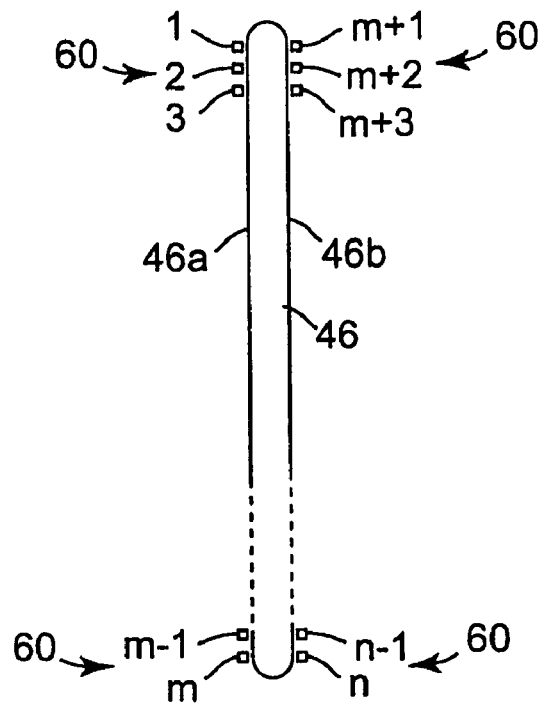
FIG. 3 is a diagram illustrating a layout of drop generators located along an ink feed slot in one embodiment of a printhead die.

FIG. 3 is a diagram illustrating drop generators 60 located along ink feed slot 46 in one embodiment of printhead die 40. Ink feed slot 46 includes opposing ink feed slot sides 46a and 46b. Drop generators 60 are disposed along each of the opposing ink feed slot sides 46a and 46b. A total of n drop generators 60 are located along ink feed slot 46, with m drop generators 60 located along ink feed slot side 46a, and n–m drop generators 60 located along ink feed slot side 46b. In one embodiment, n equals 200 drop generators 60 located along ink feed slot 46 and m equals 100 drop generators 60 located along each of the opposing ink feed slot sides 46a and 46b. In other embodiments, any suitable number of drop generators 60 can be disposed along ink feed slot 46.

Ink feed slot 46 provides ink to each of the n drop generators 60 disposed along ink feed slot 46. Each of the n drop generators 60 includes a firing resistor 52, a vaporization chamber 56 and a nozzle 34. Each of the n vaporization chambers 56 is fluidically coupled to ink feed slot 46 through at least one ink feed channel 54. The firing resistors 52 of drop generators 60 are energized in a controlled sequence to eject fluid from vaporization chambers 56 and through nozzles 34 to print an image on print medium 36.

Figure 4:
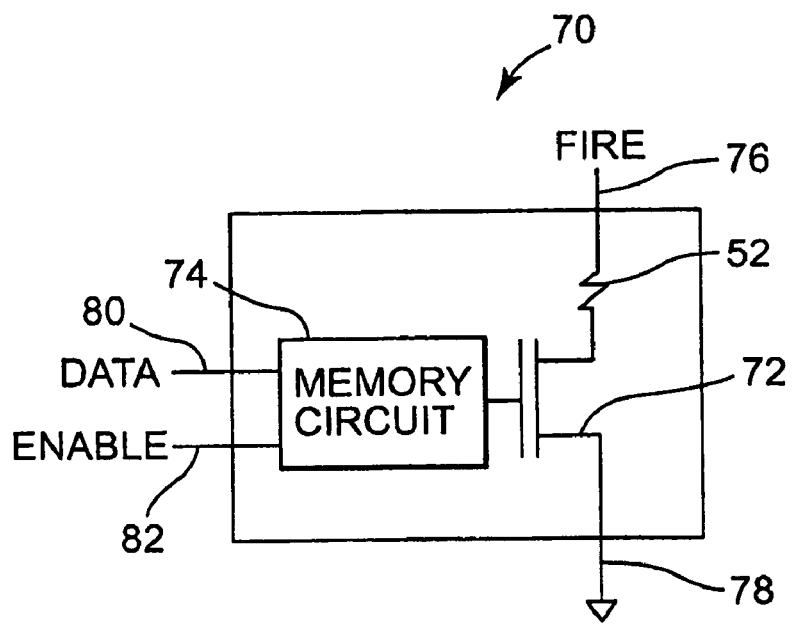
FIG. 4 is a diagram illustrating one embodiment of a firing cell employed in one embodiment of a printhead die.

FIG. 4 is a diagram illustrating one embodiment of a firing cell 70 employed in one embodiment of printhead die 40. Firing cell 70 includes a firing resistor 52, a resistor drive switch 72, and a memory circuit 74. Firing resistor 52 is part of a drop generator 60. Drive switch 72 and memory circuit 74 are part of the circuitry that controls the application of electrical current through firing resistor 52. Firing cell 70 is formed in thin-film structure 48 and on substrate 44.

In one embodiment, firing resistor 52 is a thin-film resistor and drive switch 72 is a field effect transistor (FET). Firing resistor 52 is electrically coupled to a fire line 76 and the drain-source path of drive switch 72. The drain-source path of drive switch 72 is also electrically coupled to a reference line 78 that is coupled to a reference voltage, such as ground. The gate of drive switch 72 is electrically coupled to memory circuit 74 that controls the state of drive switch 72.

Memory circuit 74 is electrically coupled to a data line 80 and enable lines 82. Data line 80 receives a data signal that represents part of an image and enable lines 82 receive enable signals to control operation of memory circuit 74. Memory circuit 74 stores one bit of data as it is enabled by the enable signals. The logic level of the stored data bit sets the state (e.g., on or off, conducting or non-conducting) of drive switch 72. The enable signals can include one or more select signals and one or more address signals.

Fire line 76 receives an energy signal comprising energy pulses and provides an energy pulse to firing resistor 52. In one embodiment, the energy pulses are provided by electronic controller 30 to have timed starting times and timed duration to provide a proper amount of energy to heat and vaporize fluid in the vaporization chamber 56 of a drop generator 60. If drive switch 72 is on (conducting), the energy pulse heats firing resistor 52 to heat and eject fluid from drop generator 60. If drive switch 72 is off (non-conducting), the energy pulse does not heat firing resistor 52 and the fluid remains in drop generator 60.

Figure 5:
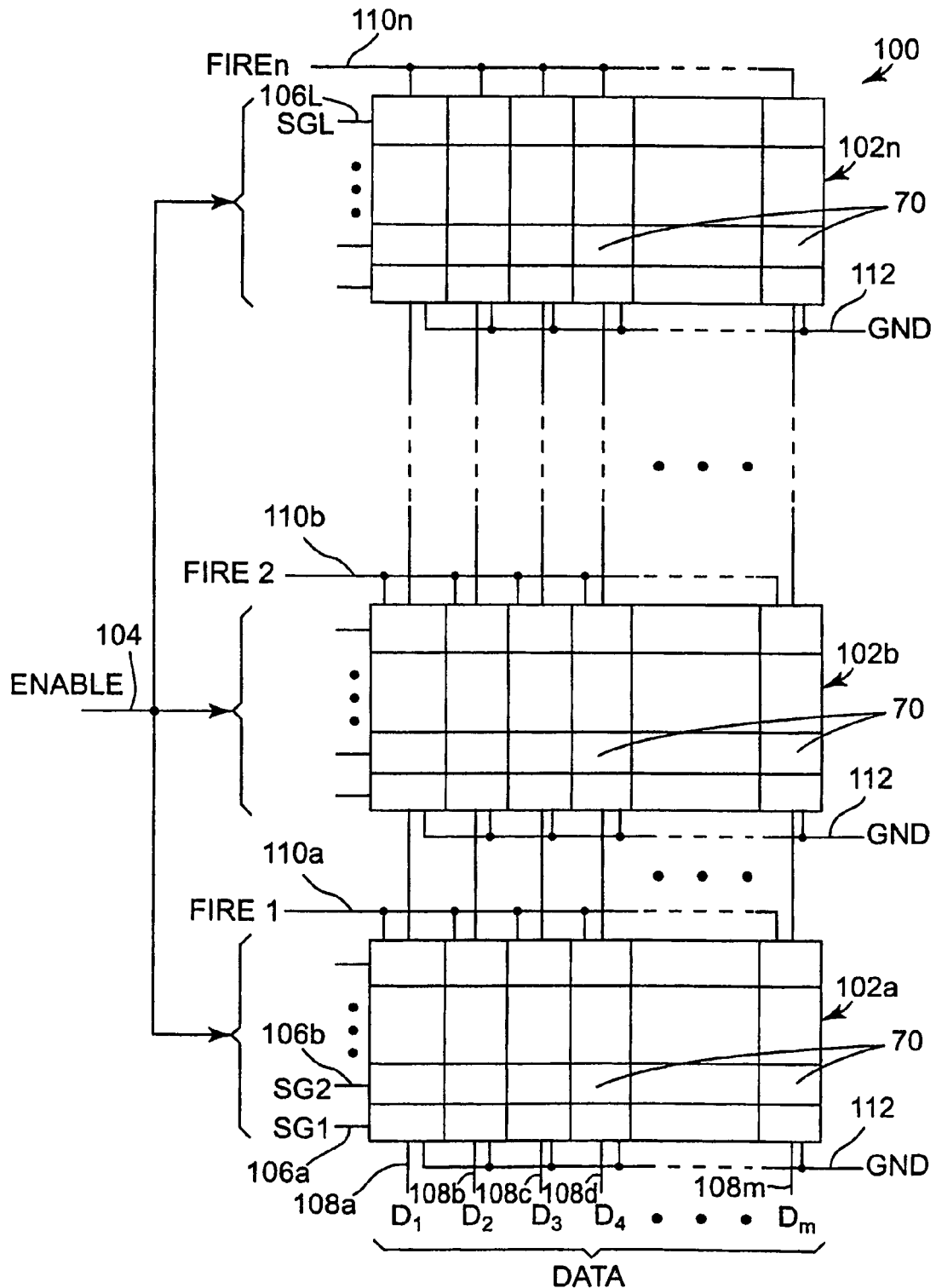
FIG. 5 is a schematic diagram illustrating one embodiment of an ink jet printhead firing cell array.

FIG. 5 is a schematic diagram illustrating one embodiment of an inkjet printhead firing cell array, indicated at 100. Firing cell array 100 includes a plurality of firing cells 70 arranged into n fire groups 102a-102n. In one embodiment, firing cells 70 are arranged into six fire groups 102a-102n. In other embodiments, firing cells 70 can be arranged into any suitable number of fire groups 102a-102n, such as four or more fire groups 102a-102n.

The firing cells 70 in array 100 are schematically arranged into L rows and m columns. The L rows of firing cells 70 are electrically coupled to enable lines 104 that receive enable signals. Each row of firing cells 70, referred to herein as a row subgroup or subgroup of firing cells 70, is electrically coupled to one set of subgroup enable lines 106a-106L. The subgroup enable lines 106a-106L receive subgroup enable signals SG1, SG2, . . . $SG_L$ that enable the corresponding subgroup of firing cells 70.

The m columns are electrically coupled to m data lines 108a-108m that receive data signals D1, D2 . . . Dm, respectively. Each of the m columns includes firing cells 70 in each of the n fire groups 102a-102n and each column of firing cells 70, referred to herein as a data line group or data group, is electrically coupled to one of the data lines 108a-108m. In other words, each of the data lines 108a-108m is electrically coupled to each of the firing cells 70 in one column, including firing cells 70 in each of the fire groups 102a-102n. For example, data line 108a is electrically coupled to each of the firing cells 70 in the far left column, including firing cells 70 in each of the fire groups 102a-102n. Data line 108b is electrically coupled to each of the firing cells 70 in the adjacent column and so on, over to and including data line 108m that is electrically coupled to each of the firing cells 70 in the far right column, including firing cells 70 in each of the fire groups 102a-102n.

In one embodiment, array 100 is arranged into six fire groups 102a-102n and each of the six fire groups 102a-102n includes 13 subgroups and eight data line groups. In other embodiments, array 100 can be arranged into any suitable number of fire groups 102a-102n and into any suitable number of subgroups and data line groups. In any embodiment, fire groups 102a-102n are not limited to having the same number of subgroups and data line groups. Instead, each of the fire groups 102a-102n can have a different number of subgroups and/or data line groups as compared to any other fire group 102a-102n. In addition, each subgroup can have a different number of firing cells 70 as compared to any other subgroup, and each data line group can have a different number of firing cells 70 as compared to any other data line group.

The firing cells 70 in each of the fire groups 102a-102n are electrically coupled to one of the fire lines 110a-110n. In fire group 102a, each of the firing cells 70 is electrically coupled to fire line 110a that receives fire signal or energy signal FIRE1. In fire group 102b, each of the firing cells 70 is electrically coupled to fire line 110b that receives fire signal or energy signal FIRE2 and so on, up to and including fire group 102n wherein each of the firing cells 70 is electrically coupled to fire line 110n that receives fire signal or energy signal FIREn. In addition, each of the firing cells 70 in each of the fire groups 102a-102n is electrically coupled to a common reference line 112 that is tied to ground.

In operation, subgroup enable signals SG1, SG2, . . . $SG_L$ are provided on subgroup enable lines 106a-106L to enable one subgroup of firing cells 70. The enabled firing cells 70 store data signals D1, D2 . . . Dm provided on data lines 108a-108m. The data signals D1, D2 . . . Dm are stored in memory circuits 74 of enabled firing cells 70. Each of the stored data signals D1, D2 . . . Dm sets the state of drive switch 72 in one of the enabled firing cells 70. The drive switch 72 is set to conduct or not conduct based on the stored data signal value.

After the states of the selected drive switches 72 are set, an energy signal FIRE1-FIREn is provided on the fire line 110a-110n corresponding to the fire group 102a-102n that includes the selected subgroup of firing cells 70. The energy signal FIRE1-FIREn includes an energy pulse. The energy pulse is provided on the selected fire line 110a-110n to energize firing resistors 52 in firing cells 70 that have conducting drive switches 72. The energized firing resistors 52 heat and eject ink onto print medium 36 to print an image represented by data signals D1, D2 . . . Dm. The process of enabling a subgroup of firing cells 70, storing data signals D1, D2 . . . Dm in the enabled subgroup and providing an energy signal FIRE1-FIREn to energize firing resistors 52 in the enabled subgroup continues until printing stops.

In one embodiment, as an energy signal FIRE1-FIREn is provided to a selected fire group 102a-102n, subgroup enable signals SG1, SG2, . . . $SG_L$ change to select and enable another subgroup in a different fire group 102a-102n. The newly enabled subgroup stores data signals D1, D2 . . . Dm provided on data lines 108a-108m and an energy signal FIRE1-FIREn is provided on one of the fire lines 110a-110n to energize firing resistors 52 in the newly enabled firing cells 70. At any one time, only one subgroup of firing cells 70 is enabled by subgroup enable signals SG1, SG2, . . . $SG_L$ to store data signals D1, D2 . . . Dm provided on data lines 108a-108m. In this aspect, data signals D1, D2 . . . Dm on data lines 108a-108m are timed division multiplexed data signals. Also, only one subgroup in a selected fire group 102a-102n includes drive switches 72 that are set to conduct while an energy signal FIRE1-FIREn is provided to the selected fire group 102a-102n. However, energy signals FIRE1-FIREn provided to different fire groups 102a-102n can and do overlap.

Figure 6:
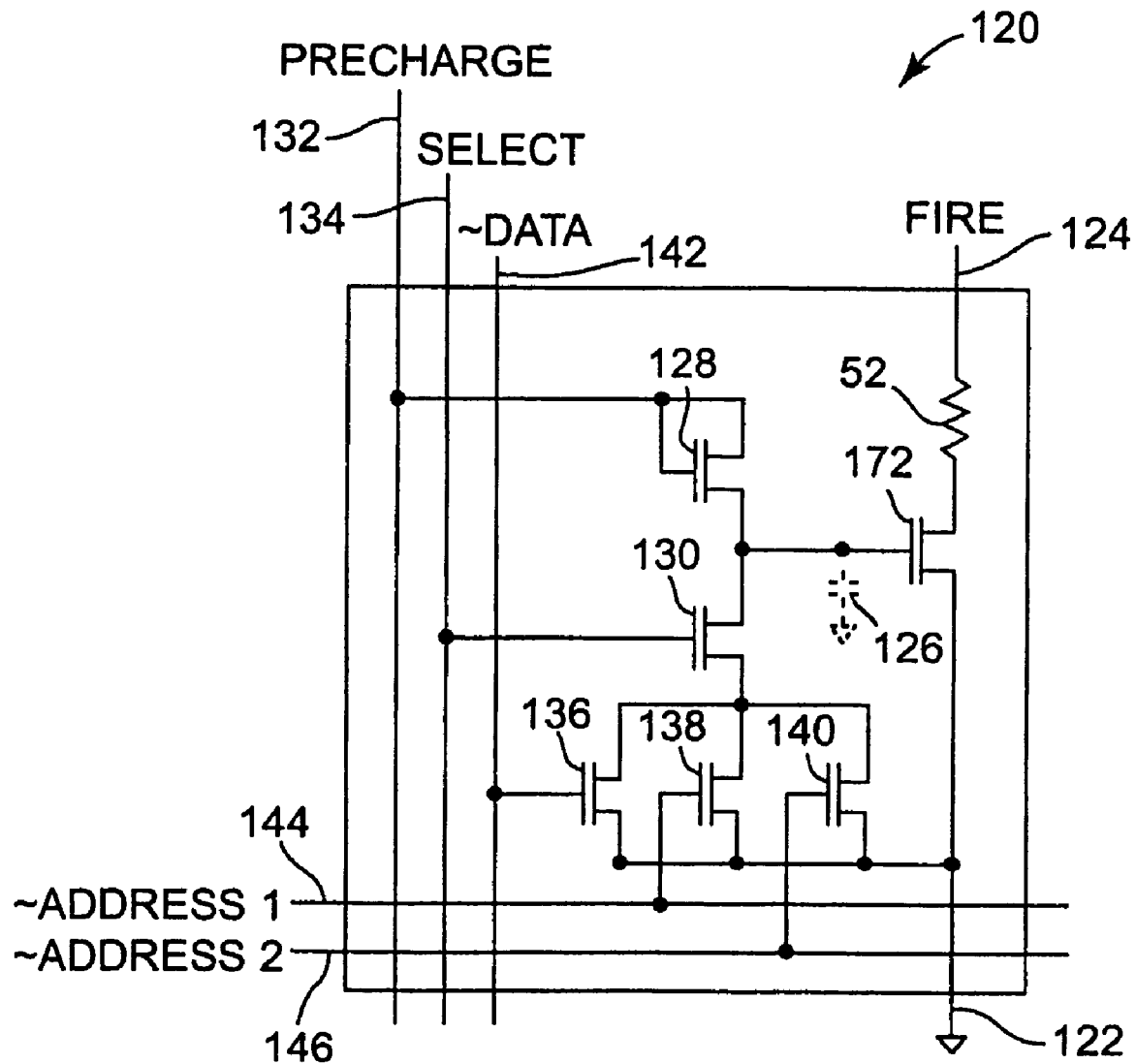
FIG. 6 is a schematic diagram illustrating one embodiment of a pre-charged firing cell.

FIG. 6 is a schematic diagram illustrating one embodiment of a pre-charged firing cell 120. Pre-charged firing cell 120 is one embodiment of firing cell 70. The pre-charged firing cell 120 includes a drive switch 172 electrically coupled to a firing resistor 52. In one embodiment, drive switch 172 is a FET including a drain-source path electrically coupled at one end to one terminal of firing resistor 52 and at the other end to a reference line 122. The reference line 122 is tied to a reference voltage, such as ground. The other terminal of firing resistor 52 is electrically coupled to a fire line 124 that receives a fire signal or energy signal FIRE including energy pulses. The energy pulses energize firing resistor 52 if drive switch 172 is on (conducting).

The gate of drive switch 172 forms a storage node capacitance 126 that functions as a memory element to store data pursuant to the sequential activation of a pre-charge transistor 128 and a select transistor 130. The drain-source path and gate of pre-charge transistor 128 are electrically coupled to a pre-charge line 132 that receives a pre-charge signal. The gate of drive switch 172 is electrically coupled to the drain-source path of pre-charge transistor 128 and the drain-source path of select transistor 130. The gate of select transistor 130 is electrically coupled to a select line 134 that receives a select signal. The storage node capacitance 126 is shown in dashed lines, as it is part of drive switch 172. Alternatively, a capacitor separate from drive switch 172 can be used as a memory element.

A data transistor 136, a first address transistor 138 and a second address transistor 140 include drain-source paths that are electrically coupled in parallel. The parallel combination of data transistor 136, first address transistor 138 and second address transistor 140 is electrically coupled between the drain-source path of select transistor 130 and reference line 122. The serial circuit including select transistor 130 coupled to the parallel combination of data transistor 136, first address transistor 138 and second address transistor 140 is electrically coupled across node capacitance 126 of drive switch 172. The gate of data transistor 136 is electrically coupled to data line 142 that receives data signals ~DATA. The gate of first address transistor 138 is electrically coupled to an address line 144 that receives address signals ~ADDRESS1 and the gate of second address transistor 140 is electrically coupled to a second address line 146 that receives address signals ~ADDRESS2. The data signals ~DATA and address signals ~ADDRESS1 and ~ADDRESS2 are active when low as indicated by the tilda (~) at the beginning of the signal name. The node capacitance 126, pre-charge transistor 128, select transistor 130, data transistor 136 and address transistors 138 and 140 form a memory cell.

In operation, node capacitance 126 is pre-charged through pre-charge transistor 128 by providing a high level voltage pulse on pre-charge line 132. In one embodiment, after the high level voltage pulse on pre-charge line 132, a data signal ~DATA is provided on data line 142 to set the state of data transistor 136 and address signals ~ADDRESS1 and ~ADDRESS2 are provided on address lines 144 and 146 to set the states of first address transistor 138 and second address transistor 140. A voltage pulse of sufficient magnitude is provided on select line 134 to turn on select transistor 130 and node capacitance 126 discharges if data transistor 136, first address transistor 138 and/or second address transistor 140 is on. Alternatively, node capacitance 126 remains charged if data transistor 136, first address transistor 138 and second address transistor 140 are all off.

Pre-charged firing cell 120 is an addressed firing cell if both address signals ~ADDRESS1 and ~ADDRESS2 are low and node capacitance 126 either discharges if data signal ~DATA is high or remains charged if data signal ~DATA is low. Pre-charged firing cell 120 is not an addressed firing cell if at least one of the address signals ~ADDRESS1 and ~ADDRESS2 is high and node capacitance 126 discharges regardless of the data signal ~DATA voltage level. The first and second address transistors 138 and 140 comprise an address decoder, and data transistor 136 controls the voltage level on node capacitance 126 if pre-charged firing cell 120 is addressed.

Pre-charged firing cell 120 may utilize any number of other topologies or arrangements, as long as the operational relationships described above are maintained. For example, an OR gate may be coupled to address lines 144 and 146, the output of which is coupled to a single transistor.

Figure 7:
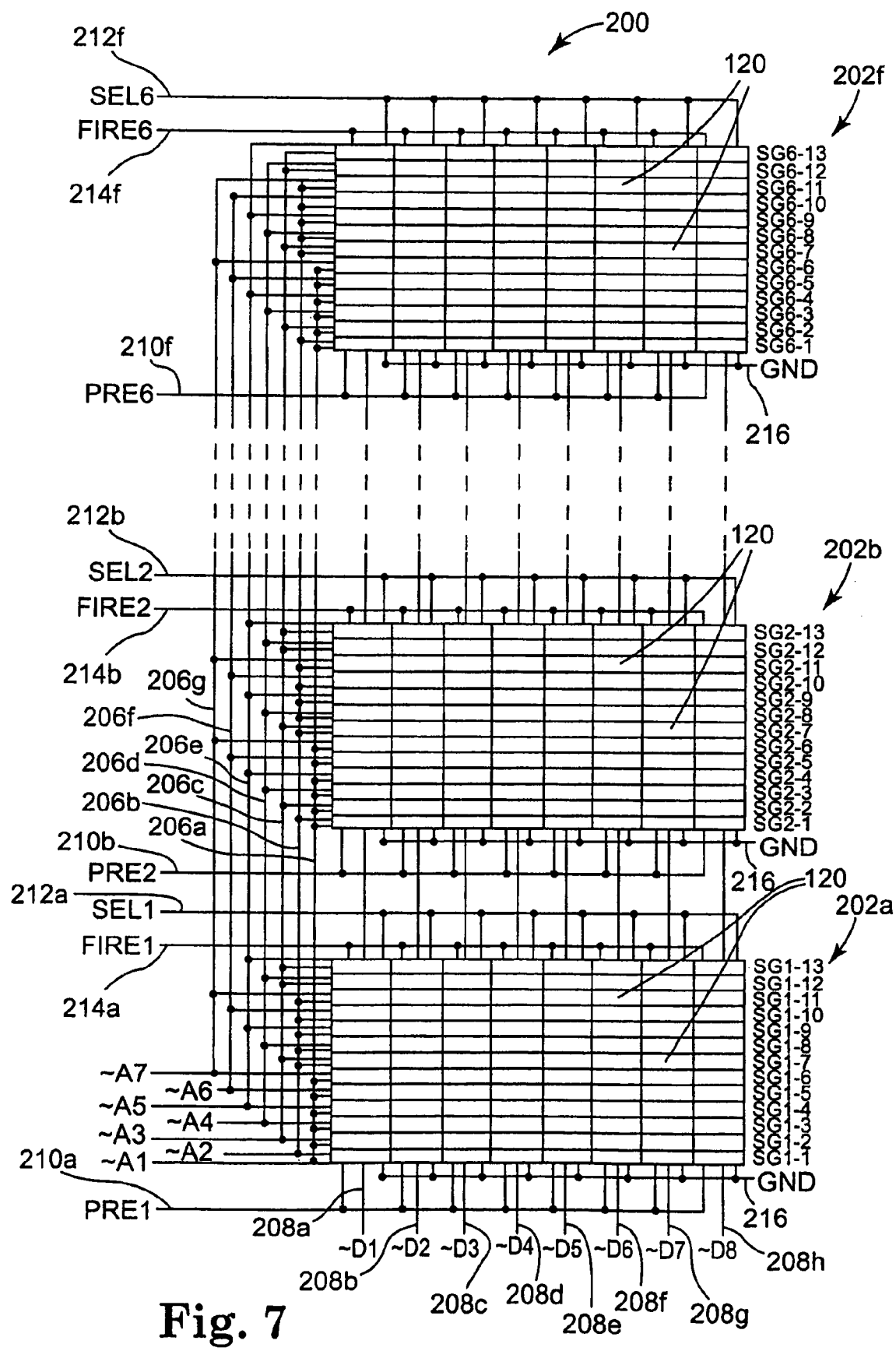
FIG. 7 is a schematic diagram illustrating one embodiment of an ink jet printhead firing cell array.

FIG. 7 is a schematic diagram illustrating one embodiment of an inkjet printhead firing cell array 200. Firing cell array 200 includes a plurality of pre-charged firing cells 120 arranged into six-fire groups 202a-202f. The pre-charged firing cells 120 in each fire group 202a-202f are schematically arranged into 13 rows and eight columns. The fire groups 202a-202f and pre-charged firing cells 120 in array 200 are schematically arranged into 78 rows and eight columns, although the number of pre-charged firing cells and their layout may vary as desired.

The eight columns of pre-charged firing cells 120 are electrically coupled to eight data lines 208a-208h that receive data signals ~D1, ~D2 . . . ~D8, respectively. Each of the eight columns, referred to herein as a data line group or data group, includes pre-charged firing cells 120 in each of the six fire groups 202a-202f. Each of the firing cells 120 in each column of pre-charged firing cells 120 is electrically coupled to one of the data lines 208a-208h. All pre-charged firing cells 120 in a data line group are electrically coupled to the same data line 208a-208h that is electrically coupled to the gates of the data transistors 136 in the pre-charged firing cells 120 in the column.

Data line 208a is electrically coupled to each of the pre-charged firing cells 120 in the far left column, including pre-charged firing cells in each of the fire groups 202a-202f. Data line 208b is electrically coupled to each of the pre-charged firing cells 120 in the adjacent column and so on, over to and including data line 208h that is electrically coupled to each of the pre-charged firing cells 120 in the far right column, including pre-charged firing cells 120 in each of the fire groups 202a-202f.

The rows of pre-charged firing cells 120 are electrically coupled to address lines 206a-206g that receive address signals ~A1, ~A2 . . . ~A7, respectively. Each pre-charged firing cell 120 in a row of pre-charged firing cells 120, referred to herein as a row subgroup or subgroup of pre-charged firing cells 120, is electrically coupled to two of the address lines 206a-206g. All pre-charged firing cells 120 in a row subgroup are electrically coupled to the same two address lines 206a-206g.

The subgroups of the fire groups 202a-202f are identified as subgroups SG1-1 through SG1-13 in fire group one (FG1) 202a, subgroups SG2-1 through SG2-13 in fire group two (FG2) 202b and so on, up to and including subgroups SG6-1 through SG6-13 in fire group six (FG6) 202f. In other embodiments, each fire group 202a-202f can include any suitable number of subgroups, such as 14 or more subgroups.

Each subgroup of pre-charged firing cells 120 is electrically coupled to two address lines 206a-206g. The two address lines 206a-206g corresponding to a subgroup are electrically coupled to the first and second address transistors 138 and 140 in all pre-charged firing cells 120 of the subgroup. One address line 206a-206g is electrically coupled to the gate of one of the first and second address transistors 138 and 140 and the other address line 206a-206g is electrically coupled to the gate of the other one of the first and second address transistors 138 and 140. The address lines 206a-206g receive address signals ~A1, ~A2 . . . ~A7 and are coupled to provide the address signals ~A1, ~A2 . . . ~A7 to the subgroups of the array 200 as follows:

| Row Subgroup Address Signals | Row Subgroups |
| --- | --- |
| ~A1, ~A2 | SG1-1, SG2-1 . . . SG6-1 |
| ~A1, ~A3 | SG1-2, SG2-2 . . . SG6-2 |
| ~A1, ~A4 | SG1-3, SG2-3 . . . SG6-3 |
| ~A1, ~A5 | SG1-4, SG2-4 . . . SG6-4 |
| ~A1, ~A6 | SG1-5, SG2-5 . . . SG6-5 |
| ~A1, ~A7 | SG1-6, SG2-6 . . . SG6-6 |
| ~A2, ~A3 | SG1-7, SG2-7 . . . SG6-7 |
| ~A2, ~A4 | SG1-8, SG2-8 . . . SG6-8 |
| ~A2, ~A5 | SG1-9, SG2-9 . . . SG6-9 |
| ~A2, ~A6 | SG1-10, SG2-10 . . . SG6-10 |
| ~A2, ~A7 | SG1-11, SG2-11 . . . SG6-11 |
| ~A3, ~A4 | SG1-12, SG2-12 . . . SG6-12 |
| ~A3, ~A5 | SG1-13, SG2-13 . . . SG6-13 |

Subgroups of pre-charged firing cells 120 are addressed by providing address signals ~A1, ~A2 . . . ~A7 on address lines 206a-206g. In one embodiment, the address lines 206a-206g are electrically coupled to one or more address generators provided on printhead die 40.

Pre-charge lines 210a-210f receive pre-charge signals PRE1, PRE2 . . . PRE6 and provide the pre-charge signals PRE1, PRE2 . . . PRE6 to corresponding fire groups 202a-202f. Pre-charge line 210a is electrically coupled to all of the pre-charged firing cells 120 in FG1 202a. Pre-charge line 210b is electrically coupled to all pre-charged firing cells 120 in FG2 202b and so on, up to and including pre-charge line 210f that is electrically coupled to all pre-charged firing cells 120 in FG6 202f. Each of the pre-charge lines 210a-210f is electrically coupled to the gate and drain-source path of all of the pre-charge transistors 128 in the corresponding fire group 202a-202f, and all pre-charged firing cells 120 in a fire group 202a-202f are electrically coupled to only one pre-charge line 210a-210f. Thus, the node capacitances 126 of all pre-charged firing cells 120 in a fire group 202a-202f are charged by providing the corresponding pre-charge signal PRE1, PRE2 . . . PRE6 to the corresponding pre-charge line 210a-210f.

Select lines 212a-212f receive select signals SEL1, SEL2 . . . SEL6 and provide the select signals SEL1, SEL2 . . . SEL6 to corresponding fire groups 202a-202f. Select line 212a is electrically coupled to all pre-charged firing cells 120 in FG1 202a. Select line 212b is electrically coupled to all pre-charged firing cells 120 in FG2 202b and so on, up to and including select line 212f that is electrically coupled to all pre-charged firing cells 120 in FG6 202f. Each of the select lines 212a-212f is electrically coupled to the gate of all of the select transistors 130 in the corresponding fire group 202a-202f, and all pre-charged firing cells 120 in a fire group 202a-202f are electrically coupled to only one select line 212a-212f.

Fire lines 214a-214f receive fire signals or energy signals FIRE1, FIRE2 . . . FIRE6 and provide the energy signals FIRE1, FIRE2 . . . FIRE6 to corresponding fire groups 202a-202f. Fire line 214a is electrically coupled to all pre-charged firing cells 120 in FG1 202a. Fire line 214b is electrically coupled to all pre-charged firing cells 120 in FG2 202b and so on, up to and including fire line 214f that is electrically coupled to all pre-charged firing cells 120 in FG6 202f. Each of the fire lines 214a-214f is electrically coupled to all of the firing resistors 52 in the corresponding fire group 202a-202f, and all pre-charged firing cells 120 in a fire group 202a-202f are electrically coupled to only one fire line 214a-214f. The fire lines 214a-214f are electrically coupled to external supply circuitry by appropriate interface pads. (See, FIGS. 25A and 25B). All pre-charged firing cells 120 in array 200 are electrically coupled to a reference line 216 that is tied to a reference voltage, such as ground. Thus, the pre-charged firing cells 120 in a row subgroup of pre-charged firing cells 120 are electrically coupled to the same address lines 206a-206g, pre-charge line 210a-210f, select line 212a-212f and fire line 214a-214f.

In operation, in one embodiment fire groups 202a-202f are selected to fire in succession. FG1 202a is selected before FG2 202b, which is selected before FG3 and so on, up to FG6 202f. After FG6 202f, the fire group cycle starts over with FG1 202a. However, other sequences, and non-sequential selections may be utilized.

The address signals ~A1, ~A2 ... ~A7 cycle through the 13 row subgroup addresses before repeating a row subgroup address. The address signals ~A1, ~A2 ... ~A7 provided on address lines 206a-206g are set to one row subgroup address during each cycle through the fire groups 202a-202f. The address signals ~A1, ~A2 ... ~A7 select one row subgroup in each of the fire groups 202a-202f for one cycle through the fire groups 202a-202f. For the next cycle through fire groups 202a-202f, the address signals ~A1, ~A2 ... ~A7 are changed to select another row subgroup in each of the fire groups 202a-202f. This continues up to the address signals ~A1, ~A2 ... ~A7 selecting the last row subgroup in fire groups 202a-202f. After the last row subgroup, address signals ~A1, ~A2 ... ~A7 select the first row subgroup to begin the address cycle over again.

In another aspect of operation, one of the fire groups 202a-202f is operated by providing a pre-charge signal PRE1, PRE2 ... PRE6 on the pre-charge line 210a-210f of the one fire group 202a-202f. The pre-charge signal PRE1, PRE2 ... PRE6 defines a pre-charge time interval or period during which time the node capacitance 126 on each drive switch 172 in the one fire group 202a-202f is charged to a high voltage level, to pre-charge the one fire group 202a-202f.

Address signals ~A1, ~A2 ... ~A7 are provided on address lines 206a-206g to address one row subgroup in each of the fire groups 202a-202f, including one row subgroup in the pre-charged fire group 202a-202f. Data signals ~D1, ~D2 ... ~D8 are provided on data lines 208a-208h to provide data to all fire groups 202a-202f, including the addressed row subgroup in the pre-charged fire group 202a-202f.

Next, a select signal SEL1, SEL2 ... SEL6 is provided on the select line 212a-212f of the pre-charged fire group 202a-202f to select the pre-charged fire group 202a-202f. The select signal SEL1, SEL2 ... SEL6 defines a discharge time interval for discharging the node capacitance 126 on each drive switch 172 in a pre-charged firing cell 120 that is either not in the addressed row subgroup in the selected fire group 202a-202f or addressed in the selected fire group 202a-202f and receiving a high level data signal ~D1, ~D2 ... ~D8. The node capacitance 126 does not discharge in pre-charged firing cells 120 that are addressed in the selected fire group 202a-202f and receiving a low level data signal ~D1, ~D2 ... ~D8. A high voltage level on the node capacitance 126 turns the drive switch 172 on (conducting).

After drive switches 172 in the selected fire group 202a-202f are set to conduct or not conduct, an energy pulse or voltage pulse is provided on the fire line 214a-214f of the selected fire group 202a-202f. Pre-charged firing cells 120 that have conducting drive switches 172, conduct current through the firing resistor 52 to heat ink and eject ink from the corresponding drop generator 60.

With fire groups 202a-202f operated in succession, the select signal SEL1, SEL2 ... SEL6 for one fire group 202a-202f is used as the pre-charge signal PRE1, PRE2 ... PRE6 for the next fire group 202a-202f. The pre-charge signal PRE1, PRE2 ... PRE6 for one fire group 202a-202f precedes the select signal SEL1, SEL2 ... SEL6 and energy signal FIRE1, FIRE2 ... FIRE6 for the one fire group 202a-202f. After the pre-charge signal PRE1, PRE2 ... PRE6, data signals ~D1, ~D2 ... ~D8 are multiplexed in time and stored in the addressed row subgroup of the one fire group 202a-202f by the select signal SEL1, SEL2 ... SEL6. The select signal SEL1, SEL2 ... SEL6 for the selected fire group 202a-202f is also the pre-charge signal PRE1, PRE2 ... PRE6 for the next fire group 202a-202f. After the select signal SEL1, SEL2 ... SEL6 for the selected fire group 202a-202f is complete, the select signal SEL1, SEL2 ... SEL6 for the next fire group 202a-202f is provided. Pre-charged firing cells 120 in the selected subgroup fire or heat ink based on the stored data signal ~D1, ~D2 ... ~D8 as the energy signal FIRE1, FIRE2 ... FIRE6, including an energy pulse, is provided to the selected fire group 202a-202f.

Figure 8:
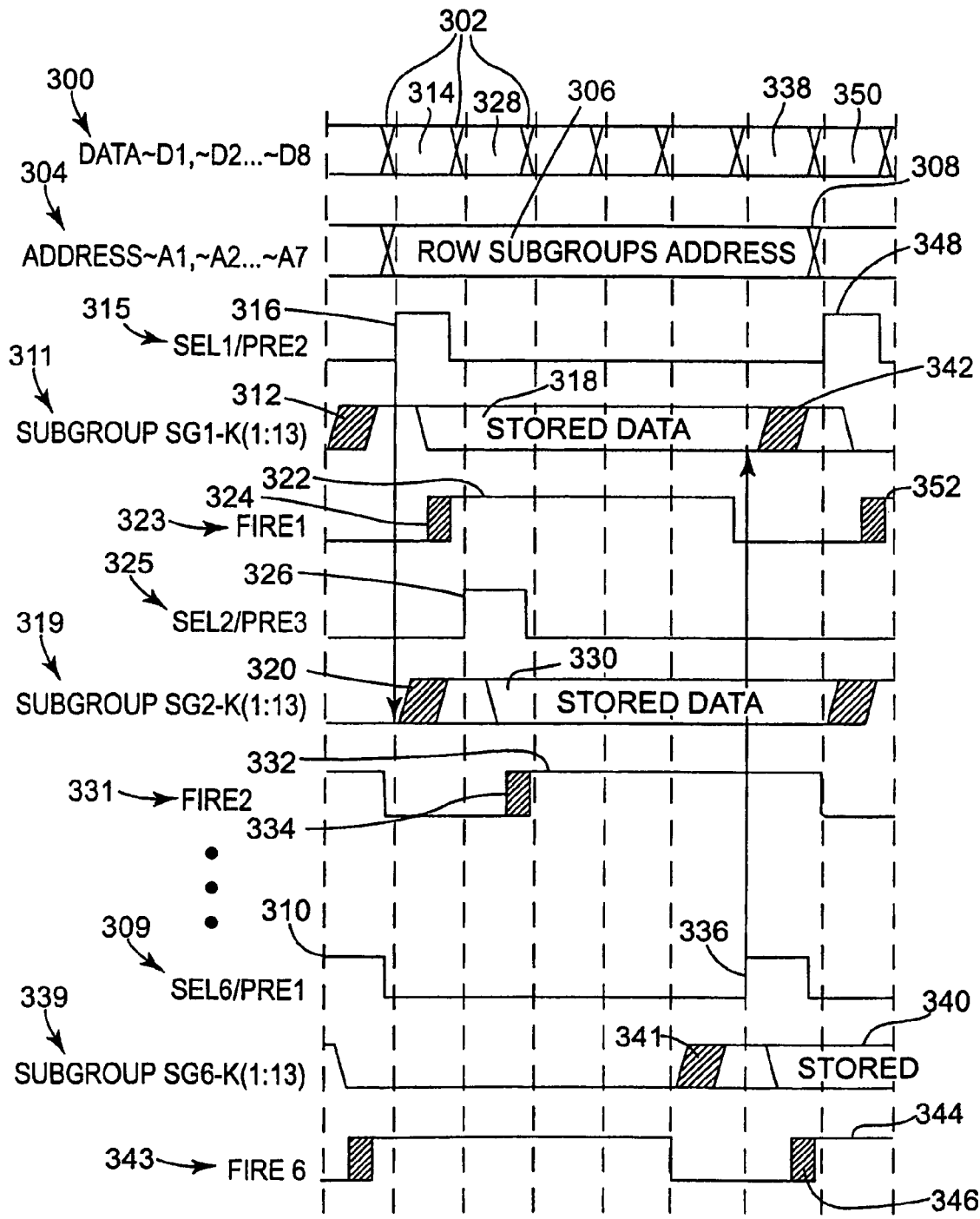
FIG. 8 is a timing diagram illustrating the operation of one embodiment of a firing cell array.

FIG. 8 is a timing diagram illustrating the operation of one embodiment of firing cell array 200. Fire groups 202a-202f are selected in succession to energize pre-charged firing cells 120 based on data signals ~D1, ~D2 ... ~D8, indicated at 300. The data signals ~D1, ~D2 ... ~D8 at 300 are changed depending on the nozzles that are to eject fluid, indicated at 302, for each row subgroup address and fire group 202a-202f combination. Address signals ~A1, ~A2 ... ~A7 at 304 are provided on address lines 206a-206g to address one row subgroup from each of the fire groups 202a-202f. The address signals ~A1, ~A2 ... ~A7 at 304 are set to one address, indicated at 306, for one cycle through fire groups 202a-202f. After the cycle is complete, the address signals ~A1, ~A2 ... ~A7 at 304 are changed at 308 to address a different row subgroup from each of the fire groups 202a-202f. The address signals ~A1, ~A2 ... ~A7 at 304 increment through the row subgroups to address the row subgroups in sequential order from one to 13 and back to one. In other embodiments, address signals ~A1, ~A2 ... ~A7 at 304 can be set to address row subgroups in any suitable order.

During a cycle through fire groups 202a-202f, select line 212f coupled to FG6 202f and pre-charge line 210a coupled to FG1 202a receive SEL6/PRE1 signal 309, including SEL6/PRE1 signal pulse 310. In one embodiment, the select line 212f and pre-charge line 210a are electrically coupled together to receive the same signal. In another embodiment, the select line 212f and pre-charge line 210a are not electrically coupled together, but receive similar signals.

The SEL6/PRE1 signal pulse at 310 on pre-charge line 210a, pre-charges all firing cells 120 in FG1 202a. The node capacitance 126 for each of the pre-charged firing cells 120 in FG1 202a is charged to a high voltage level. The node capacitances 126 for pre-charged firing cells 120 in one row subgroup SG1-K, indicated at 311, are pre-charged to a high voltage level at 312. The row subgroup address at 306 selects subgroup SG1-K, and a data signal set at 314 is provided to data transistors 136 in all pre-charged firing cells 120 of all fire groups 202a-202f, including the address selected row subgroup SG1-K.

The select line 212a for FG1 202a and pre-charge line 210b for FG2 202b receive the SEL1/PRE2 signal 315, including the SEL1/PRE2 signal pulse 316. The SEL1/PRE2 signal pulse 316 on select line 212a turns on the select transistor 130 in each of the pre-charged firing cells 120 in FG1 202a. The node capacitance 126 is discharged in all pre-charged firing cells 120 in FG1 202a that are not in the address selected row subgroup SG1-K. In the address selected row subgroup SG1-K, data at 314 are stored, indicated at 318, in the node capacitances 126 of the drive switches 172 in row subgroup SG1-K to either turn the drive switch on (conducting) or off (non-conducting).

The SEL1/PRE2 signal pulse at 316 on pre-charge line 210b, pre-charges all firing cells 120 in FG2 202b. The node capacitance 126 for each of the pre-charged firing cells 120 in FG2 202b is charged to a high voltage level. The node capacitances 126 for pre-charged firing cells 120 in one row subgroup SG2-K, indicated at 319, are pre-charged to a high voltage level at 320. The row subgroup address at 306 selects subgroup SG2-K, and a data signal set at 328 is provided to data transistors 136 in all pre-charged firing cells 120 of all fire groups 202a-202f, including the address selected row subgroup SG2-K.

The fire line 214a receives energy signal FIRE1, indicated at 323, including an energy pulse at 322 to energize firing resistors 52 in pre-charged firing cells 120 that have conductive drive switches 172 in FG1 202a. The FIRE1 energy pulse 322 goes high while the SEL1/PRE2 signal pulse 316 is high and while the node capacitance 126 on non-conducting drive switches 172 are being actively pulled low, indicated on energy signal FIRE1 323 at 324. Switching the energy pulse 322 high while the node capacitances 126 are actively pulled low, prevents the node capacitances 126 from being inadvertently charged through the drive switch 172 as the energy pulse 322 goes high. The SEL1/PRE2 signal 315 goes low and the energy pulse 322 is provided to FG1 202a for a predetermined time to heat ink and eject the ink through nozzles 34 corresponding to the conducting pre-charged firing cells 120.

The select line 212b for FG2 202b and pre-charge line 210c for FG3 202c receive SEL2/PRE3 signal 325, including SEL2/PRE3 signal pulse 326. After the SEL1/PRE2 signal pulse 316 goes low and while the energy pulse 322 is high, the SEL2/PRE3 signal pulse 326 on select line 212b turns on select transistor 130 in each of the pre-charged firing cells 120 in FG2 202b. The node capacitance 126 is discharged on all pre-charged firing cells 120 in FG2 202b that are not in the address selected row subgroup SG2-K. Data signal set 328 for subgroup SG2-K is stored in the pre-charged firing cells 120 of subgroup SG2-K, indicated at 330, to either turn the drive switches 172 on (conducting) or off (non-conducting). The SEL2/PRE3 signal pulse on pre-charge line 210c pre-charges all pre-charged firing cells 120 in FG3 202c.

Fire line 214b receives energy signal FIRE2, indicated at 331, including energy pulse 332, to energize firing resistors 52 in pre-charged firing cells 120 of FG2 202b that have conducting drive switches 172. The FIRE2 energy pulse 332 goes high while the SEL2/PRE3 signal pulse 326 is high, indicated at 334. The SEL2/PRE3 signal pulse 326 goes low and the FIRE2 energy pulse 332 remains high to heat and eject ink from the corresponding drop generator 60.

After the SEL2/PRE3 signal pulse 326 goes low and while the energy pulse 332 is high, a SEL3/PRE4 signal is provided to select FG3 202c and pre-charge FG4 202d. The process of pre-charging, selecting and providing an energy signal, including an energy pulse, continues up to and including FG6 202f.

The SEL5/PRE6 signal pulse on pre-charge line 210f, pre-charges all firing cells 120 in FG6 202f. The node capacitance 126 for each of the pre-charged firing cells 120 in FG6 202f is charged to a high voltage level. The node capacitances 126 for pre-charged firing cells 120 in one row subgroup SG6-K, indicated at 339, are pre-charged to a high voltage level at 341. The row subgroup address at 306 selects subgroup SG6-K, and data signal set 338 is provided to data transistors 136 in all pre-charged firing cells 120 of all fire groups 202a-202f, including the address selected row subgroup SG6-K.

The select line 212f for FG6 202f and pre-charge line 210a for FG1 202a receive a second SEL6/PRE1 signal pulse at 336. The second SEL6/PRE1 signal pulse 336 on select line 212f turns on the select transistor 130 in each of the pre-charged firing cells 120 in FG6 202f. The node capacitance 126 is discharged in all pre-charged firing cells 120 in FG6 202f that are not in the address selected row subgroup SG6-K. In the address selected row subgroup SG6-K, data 338 are stored at 340 in the node capacitances 126 of each drive switch 172 to either turn the drive switch on or off.

The SEL6/PRE1 signal on pre-charge line 210a, pre-charges node capacitances 126 in all firing cells 120 in FG1 202a, including firing cells 120 in row subgroup SG1-K, indicated at 342, to a high voltage level. The firing cells 120 in FG1 202a are pre-charged while the address signals ~A1, ~A2 . . . ~A7 304 select row subgroups SG1-K, SG2-K and on, up to row subgroup SG6-K.

The fire line 214f receives energy signal FIRE6, indicated at 343, including an energy pulse at 344 to energize fire resistors 52 in pre-charged firing cells 120 that have conductive drive switches 172 in FG6 202f. The energy pulse 344 goes high while the SEL6/PRE1 signal pulse 336 is high and node capacitances 126 on non-conducting drive switches 172 are being actively pulled low, indicated at 346. Switching the energy pulse 344 high while the node capacitances 126 are actively pulled low, prevents the node capacitances 126 from being inadvertently charged through drive switch 172 as the energy pulse 344 goes high. The SEL6/PRE1 signal pulse 336 goes low and the energy pulse 344 is maintained high for a predetermined time to heat ink and eject ink through nozzles 34 corresponding to the conducting pre-charged firing cells 120.

After the SEL6/PRE1 signal pulse 336 goes low and while the energy pulse 344 is high, address signals ~A1, ~A2 . . . ~A7 304 are changed at 308 to select another set of subgroups SG1-K+1, SG2-K+1 and so on, up to SG6-K+1. The select line 212a for FG1 202a and pre-charge line 210b for FG2 202b receive a SEL1/PRE2 signal pulse, indicated at 348. The SEL1/PRE2 signal pulse 348 on select line 212a turns on the select transistor 130 in each of the pre-charged firing cells 120 in FG1 202a. The node capacitance 126 is discharged in all pre-charged firing cells 120 in FG1 202a that are not in the address selected subgroup SG1-K+1. Data signal set 350 for row subgroup SG1-K+1 is stored in the pre-charged firing cells 120 of subgroup SG1-K+1 to either turn drive switches 172 on or off. The SEL1/PRE2 signal pulse 348 on pre-charge line 210b pre-charges all firing cells 120 in FG2 202b.

The fire line 214a receives energy pulse 352 to energize firing resistors 52 and pre-charged firing cells 120 of FG1 202a that have conducting drive switches 172. The energy pulse 352 goes high while the SEL1/PRE2 signal pulse at 348 is high. The SEL1/PRE2 signal pulse 348 goes low and the energy pulse 352 remains high to heat and eject ink from corresponding drop generators 60. The process continues until printing is complete.

Figure 9:
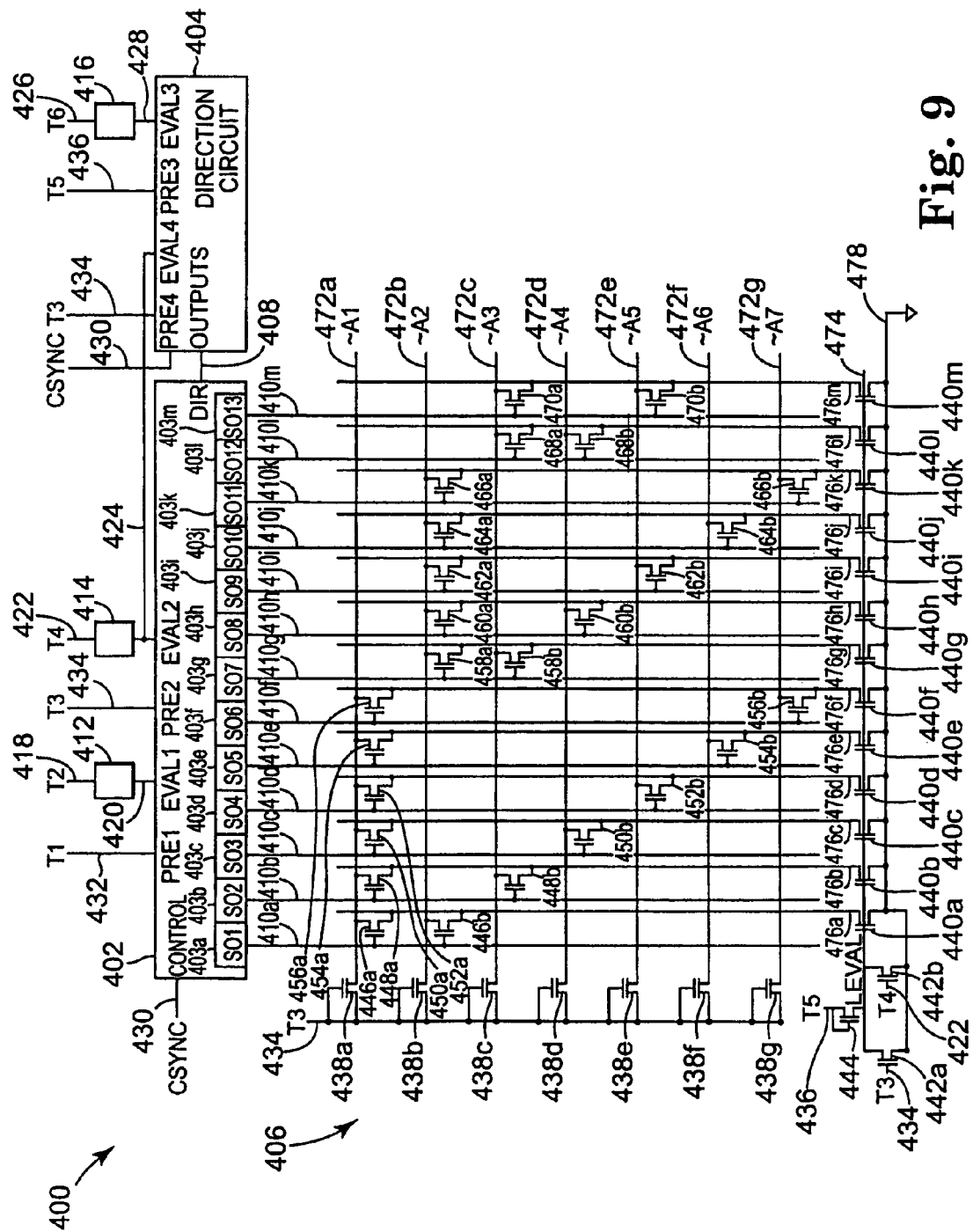
FIG. 9 is a diagram illustrating one embodiment of an address generator in a printhead die.

FIG. 9 is a diagram illustrating one embodiment of an address generator 400 in printhead die 40. The address generator 400 includes a shift register 402, a direction circuit 404 and a logic array 406. The shift register 402 is electrically coupled to direction circuit 404 through direction control lines 408. Also, shift register 402 is electrically coupled to logic array 406 through shift register output lines 410a-410m.

In the embodiments described below, address generator 400 provides address signals to firing cells 120. In one embodiment, the address generator 400 receives external signals, see FIGS. 25A and 25B, including a control signal CSYNC and six timing signals T1-T6, and in response provides seven address signals ~A1, ~A2, ... ~A7. The address signals ~A1, ~A2, ... ~A7 are active when they are in the low voltage level, as indicated by the preceding tilda on each signal name. In one embodiment, timing signals T1-T6 are provided on select lines (e.g., select lines 212a-212f shown in FIG. 7). Address generator 400 is one embodiment of a control circuit configured to respond to a control signal (e.g., CSYNC) to initiate a sequence (e.g., a sequence of addresses ~A1, ~A2 ... ~A7 in forward or reverse order) to enable the firing cells 120 for activation.

The address generator 400 includes resistor divide networks 412, 414 and 416 that receive timing signals T2, T4 and T6. Resistor divide network 412 receives timing signal T2 through timing signal line 418 and divides down the voltage level of timing signal T2 to provide a reduced voltage level T2 timing signal on first evaluation signal line 420. Resistor divide network 414 receives timing signal T4 though timing signal line 422 and divides down the voltage level of timing signal T4 to provide a reduced voltage level T4 timing signal on second evaluation signal line 424. Resistor divide network 416 receives timing signal T6 through timing signal line 426 and divides down the voltage level of timing signal T6 to provide a reduced voltage level T6 timing signal on third evaluation signal line 428.

The shift register 402 receives control signal CSYNC through control signal line 430 and direction signals through direction signal lines 408. Also, shift register 402 receives timing signal T1 through timing signal line 432 as first pre-charge signal PRE1. The reduced voltage level T2 timing signal is received through first evaluation signal line 420 as first evaluation signal EVAL1. Timing signal T3 is received through timing signal line 434 as second pre-charge signal PRE2, and the reduced voltage level T4 timing signal is received through second evaluation signal line 424 as second evaluation signal EVAL2. The shift register 402 provides shift register output signals SO1-SO13 on shift register output lines 410a-410m.

Shift register 402 includes thirteen shift register cells 403a-403m that provide the thirteen shift register output signals SO1-SO13. Each shift register cell 403a-403m provides one of the shift register output signals SO1-SO13. The thirteen shift register cells 403a-403m are electrically coupled in series to provide shifting in the forward direction and the reverse direction. In other embodiments, shift register 402 can include any suitable number of shift register cells 403 to provide any suitable number of shift register output signals, to provide any number of desired address signals.

Shift register cell 403a provides shift register output signal SO1 on shift register output line 410a. Shift register cell 403b provides shift register output signal SO2 on shift register output line 410b. Shift register cell 403c provides shift register output signal SO3 on shift register output line 410c. Shift register cell 403d provides shift register output signal SO4 on shift register output line 410d. Shift register cell 403e provides shift register output signal SO5 on shift register output line 410e. Shift register cell 403f provides shift register output signal SO6 on shift register output line 410f. Shift register cell 403g provides shift register output signal SO7 on shift register output line 410g. Shift register cell 403h provides shift register output signal SO8 on shift register output line 410h. Shift register cell 403i provides shift register output signal SO9 on shift register output line 410i. Shift register cell 403j provides shift register output signal SO10 on shift register output line 410j. Shift register cell 403k provides shift register output signal SO11 on shift register output line 410k. Shift register cell 403l provides shift register output signal SO12 on shift register output line 410l and shift register cell 403m provides shift register output signal SO13 on shift register output line 410m.

The direction circuit 404 receives control signal CSYNC on control signal line 430. Timing signal T3 is received on timing signal line 434 as fourth pre-charge signal PRE4. The reduced voltage level T4 timing signal is received on evaluation signal line 424 as fourth evaluation signal EVAL4. Timing signal T5 is received on timing signal line 436 as third pre-charge signal PRE3, and the reduced voltage level T6 timing signal is received on evaluation signal line 428 as third evaluation signal EVAL3. The direction circuit 404 provides direction signals to shift register 402 through direction signal lines 408.

The logic array 406 includes address line pre-charge transistors 438a-438g, address evaluation transistors 440a-440m, evaluation prevention transistors 442a and 442b, and logic evaluation pre-charge transistor 444. Also, logic array 406 includes address transistor pairs 446, 448, ... 470 that decode shift register output signals SO1-SO13 on shift register output lines 410a-410m to provide address signals ~A1, ~A2, ... ~A7. The logic array 406 includes address one transistors 446a and 446b, address two transistors 448a and 448b, address three transistors 450a and 450b, address four transistors 452a and 452b, address five transistors 454a and 454b, address six transistors 456a and 456b, address seven transistors 458a and 458b, address eight transistors 460a and 460b, address nine transistors 462a and 462b, address ten transistors 464a and 464b, address eleven transistors 466a and 466b, address twelve transistors 468a and 468b and address thirteen transistors 470a and 470b.

The address line pre-charge transistors 438a-438g are electrically coupled to T3 signal line 434 and address lines 472a-472g. The gate and one side of the drain-source path of address line pre-charge transistor 438a are electrically coupled to T3 signal line 434. The other side of the drain-source path of address line pre-charge transistor 438a is electrically coupled to address line 472a. The gate and one side of the drain-source path of address line pre-charge transistor 438b are electrically coupled to T3 signal line 434. The other side of the drain-source path of address line pre-charge transistor 438b is electrically coupled to address line 472b. The gate and one side of the drain-source path of address line pre-charge transistor 438c are electrically coupled to T3 signal line 434. The other side of the drain-source path of address line pre-charge transistor 438c is electrically coupled to address line 472c. The gate and one side of the drain-source path of address line pre-charge transistor 438d are electrically coupled to T3 signal line 434. The other side of the drain-source path of address line pre-charge transistor 438d is electrically coupled to address line 472d. The gate and one side of the drain-source path of address line pre-charge transistor 438e are electrically coupled to T3 signal line 434. The other side of the drain-source path of address line pre-charge transistor 438e is electrically coupled to address line 472e. The gate and one side of the drain-source path of address line pre-charge transistor 438f are electrically coupled to T3 signal line 434. The other side of the drain-source path of address line pre-charge transistor 438f is electrically coupled to address line 472f. The gate and one side of the drain-source path of address line pre-charge transistor 438g are electrically coupled to T3 signal line 434. The other side of the drain-source path of address line pre-charge transistor 438g is electrically coupled to address line 472g. In one embodiment, address line pre-charge transistors 438a-438g are electrically coupled to T4 signal line 422, instead of T3 signal line 434. The T4 signal line 422 is electrically coupled to the gate and one side of the drain-source path of each of the address line pre-charge transistor 438a-438g.

The gate of each of the address evaluation transistors 440a-440m is electrically coupled to logic evaluation signal line 474. One side of the drain-source path of each of the address evaluation transistors 440a-440m is electrically coupled to ground. In addition, the drain-source path of address evaluation transistor 440a is electrically coupled to evaluation line 476a. The drain-source path of address evaluation transistor 440b is electrically coupled to evaluation line 476b. The drain-source path of address evaluation transistor 440c is electrically coupled to evaluation line 476c. The drain-source path of address evaluation transistor 440d is electrically coupled to evaluation line 476d. The drain-source path of address evaluation transistor 440e is electrically coupled to evaluation line 476e. The drain-source path of address evaluation transistor 440f is electrically coupled to evaluation line 476f. The drain-source path of address evaluation transistor 440g is electrically coupled to evaluation line 476g. The drain-source path of address evaluation transistor 440h is electrically coupled to evaluation line 476h. The drain-source path of address evaluation transistor 440i is electrically coupled to evaluation line 476i. The drain-source path of address evaluation transistor 440j is electrically coupled to evaluation line 476j. The drain-source path of address evaluation transistor 440k is electrically coupled to evaluation line 476k. The drain-source path of address evaluation transistor 440l is electrically coupled to evaluation line 476l. The drain-source path of address evaluation transistor 440m is electrically coupled to evaluation line 476m.

The gate and one side of the drain-source path of logic evaluation pre-charge transistor 444 are electrically coupled to T5 signal line 436 and the other side of the drain-source path is electrically coupled to logic evaluation signal line 474. The gate of evaluation prevention transistor 442a is electrically coupled to T3 signal line 434. The drain-source path of evaluation prevention transistor 442a is electrically coupled on one side to logic evaluation signal line 474 and on the other side to the reference at 478. The gate of evaluation prevention transistor 442b is electrically coupled to T4 signal line 422. The drain-source path of evaluation prevention transistor 442b is electrically coupled on one side to logic evaluation signal line 474 and on the other side to the reference at 478.

The drain-source paths of address transistor pairs 446, 448, . . . 470 are electrically coupled between address lines 472a-472g and evaluation lines 476a-476m. The gates of address transistor pairs 446, 448, . . . 470 are driven by shift register output signals SO1-SO13 through shift register output signal lines 410a-410m.

The gates of address one transistors 446a and 446b are electrically coupled to shift register output signal line 410a. The drain-source path of address one transistor 446a is electrically coupled on one side to address line 472a and on the other side to evaluation line 476a. The drain-source path of address one transistor 446b is electrically coupled on one side to address line 472b and on the other side to evaluation line 476a. A high level shift register output signal SO1 on shift register output signal line 410a turns on address one transistors 446a and 446b as address evaluation transistor 440a is turned on by a high voltage level evaluation signal LEVAL on logic evaluation signal line 474. The address one transistor 446a and address evaluation transistor 440a conduct to actively pull address line 472a to a low voltage level. The address one transistor 446b and address evaluation transistor 440a conduct to actively pull address line 472b to a low voltage level.

The gates of address two transistors 448a and 448b are electrically coupled to shift register output line 410b. The drain-source path of address two transistor 448a is electrically coupled on one side to address line 472a and on the other side to evaluation line 476b. The drain-source path of address two transistor 448b is electrically coupled on one side to address line 472c and on the other side to evaluation line 476b. A high level shift register output signal SO2 on shift register output signal line 410b turns on address two transistors 448a and 448b as address evaluation transistor 440b is turned on by a high voltage level evaluation signal LEVAL on logic evaluation signal line 474. The address two transistor 448a and address evaluation transistor 440b conduct to actively pull address line 472a to a low voltage level. The address two transistor 448b and address evaluation transistor 440b conduct to actively pull address line 472c to a low voltage level.

The gates of address three transistors 450a and 450b are electrically coupled to shift register output signal line 410c. The drain-source path of address three transistor 450a is electrically coupled on one side to address line 472a and on the other side to evaluation line 476c. The drain-source path of address three transistor 450b is electrically coupled on one side to address line 472d and on the other side to evaluation line 476c. A high level shift register output signal SO3 on shift register output signal line 410c turns on address three transistors 450a and 450b as address evaluation transistor 440c is turned on by a high voltage level evaluation signal LEVAL on logic evaluation signal line 474. The address three transistor 450a and address evaluation transistor 440c conduct to actively pull address line 472a to a low voltage level. The address three transistor 450b and address evaluation transistor 440c conduct to actively pull address line 472d to a low voltage level.

The gates of address four transistors 452a and 452b are electrically coupled to shift register output signal line 410d. The drain-source path of address four transistor 452a is electrically coupled on one side to address line 472a and on the other side to evaluation line 476d. The drain-source path of address four transistor 452b is electrically coupled on one side to address line 472e and on the other side to evaluation line 476d. A high level shift register output signal SO4 on shift register output signal line 410d turns on address four transistors 452a and 452b as address evaluation transistor 440d is turned on by a high voltage level evaluation signal LEVAL on logic evaluation signal line 474. The address four transistor 452a and address evaluation transistor 440d conduct to actively pull address line 472a to a low voltage level. The address four transistor 452b and address evaluation transistor 440d conduct to actively pull address line 472e to a low voltage level.

The gates of address five transistors 454a and 454b are electrically coupled to shift register output signal line 410e. The drain-source path of address five transistor 454a is electrically coupled on one side to address line 472a and on the other side to evaluation line 476e. The drain-source path of address five transistor 454b is electrically coupled on one side to address line 472f and on the other side to evaluation line 476e. A high level shift register output signal SO5 on shift register output signal line 410e turns on address five transistors 454a and 454b as address evaluation transistor 440e is turned on by a high voltage level evaluation signal LEVAL. The address five transistor 454a and address evaluation transistor 440e conduct to actively pull address line 472a to a low voltage level. The address five transistor 454b and address evaluation transistor 440e conduct to actively pull address line 472f to a low voltage level.

The gates of address six transistors 456a and 456b are electrically coupled to shift register output signal line 410f. The drain-source path of address six transistor 456a is electrically coupled on one side to address line 472a and on the other side to evaluation line 476f. The drain-source path of address six transistor 456b is electrically coupled on one side to address line 472g and on the other side to evaluation line 476f. A high level shift register output signal SO6 on shift register output signal line 410f turns on address six transistors 456a and 456b to conduct as address evaluation transistor 440f is turned on by a high voltage level evaluation signal LEVAL. The address six transistor 456a and address evaluation transistor 440f conduct to actively pull address line 472a to a low voltage level. The address six transistor 456b and address evaluation transistor 440f conduct to actively pull address line 472g to a low voltage level.

The gates of address seven transistors 458a and 458b are electrically coupled to shift register output signal line 410g. The drain-source path of address six transistor 458a is electrically coupled on one side to address line 472b and on the other side to evaluation line 476g. The drain source path of address seven transistor 458b is electrically coupled on one side to address line 472c and on the other side to evaluation line 476g. A high level shift register output signal SO7 on shift register output signal line 410g turns on address seven transistors 458a and 458b as address evaluation transistor 440g is turned on by a high voltage level evaluation signal LEVAL. The address seven transistor 458a and address evaluation transistor 440g conduct to actively pull address line 472b to a low voltage level. The address seven transistor 458b and address evaluation transistor 440g conduct to actively pull address line 472c to a low voltage level.

The gates of address eight transistors 460a and 460b are electrically coupled to shift register output signal line 410h. The drain-source path of address eight transistor 460a is electrically coupled on one side to address line 472b and on the other side to evaluation line 476h. The drain-source path of address eight transistor 460b is electrically coupled on one side to address line 472d and on the other side to evaluation line 476h. A high level shift register output signal SO8 on shift register output signal line 410h turns on address eight transistors 460a and 460b as address evaluation transistor 440h is turned on by a high voltage level evaluation signal LEVAL. The address eight transistor 460a and address evaluation transistor 440h conduct to actively pull address line 472b to a low voltage level. The address eight transistor 460b and address evaluation transistor 440h conduct to actively pull address line 472d to a low voltage level.

The gates of address nine transistors 462a and 462b are electrically coupled to shift register output signal line 410i. The drain-source path of address nine transistor 462a is electrically coupled on one side to address line 472b and on the other side to evaluation line 476i. The drain-source path of address nine transistor 462b is electrically coupled on one side to address line 472e and on the other side to evaluation line 476i. A high level shift register output signal SO9 on shift register output signal line 410i turns on address nine transistors 462a and 462b to conduct as address evaluation transistor 440i is turned on by a high voltage level evaluation signal LEVAL. The address nine transistor 462a and address evaluation transistor 440i conduct to actively pull address line 472b to a low voltage level. The address nine transistor 462b and address evaluation transistor 440i conduct to actively pull address line 472e to a low voltage level.

The gates of address ten transistors 464a and 464b are electrically coupled to shift register output signal line 410j. The drain-source path of address ten transistor 464a is electrically coupled on one side to address line 472b and on the other side to evaluation line 476j. The drain-source path of address ten transistor 464b is electrically coupled on one side to address line 472f and on the other side to evaluation line 476j. A high level shift register output signal SO10 on shift register output signal line 410j turns on address ten transistors 464a and 464b as address evaluation transistor 440j is turned on by a high voltage level evaluation signal LEVAL. The address ten transistor 464a and address evaluation transistor 440j conduct to actively pull address line 472b to a low voltage level. The address ten transistor 464b and address evaluation transistor 440j conduct to actively pull address line 472f to a low voltage level.

The gates of address eleven transistors 466a and 466b are electrically coupled to shift register output signal line 410k. The drain-source path of address eleven transistor 466a is electrically coupled on one side to address line 472b and on the other side to evaluation line 476k. The drain-source path of address eleven transistor 466b is electrically coupled on one side to address line 472g and on the other side to evaluation line 476k. A high level shift register output signal SO11 on shift register output signal line 410k turns on address eleven transistors 466a and 466b as address evaluation transistor 440k is turned on by a high voltage evaluation signal LEVAL. The address eleven transistor 466a and address evaluation transistor 440k conduct to actively pull address line 472b to a low voltage level. The address eleven transistor 466b and address evaluation transistor 440k conduct to actively pull address line 472g to a low voltage level.

The gates of address twelve transistors 468a and 468b are electrically coupled to shift register output signal line 410l. The drain-source path of address twelve transistor 468a is electrically coupled on one side to address line 472c and on the other side to evaluation line 476l. The drain-source path of address twelve transistor 468b is electrically coupled on one side to address line 472d and on the other side to evaluation line 476l. A high level shift register output signal SO12 on shift register output signal line 410l turns on address twelve transistors 468a and 468b as address evaluation transistor 440l is turned on by a high voltage level evaluation signal LEVAL. The address twelve transistor 468a and address evaluation transistor 440l conduct to actively pull address line 472c to a low voltage level. The address twelve transistor 468b and address evaluation transistor 440l conduct to actively pull address line 472d to a low voltage level.

The gates of address thirteen transistors 470a and 470b are electrically coupled to shift register output signal line 410m. The drain-source path of address thirteen transistor 470a is electrically coupled on one side to address line 472c and on the other side to evaluation line 476m. The drain-source path of address thirteen transistor 470b is electrically coupled on one side to address line 472e and on the other side to evaluation line 476m. A high level shift register output signal SO13 on shift register output signal line 410m turns on address thirteen transistors 470a and 470b as address evaluation transistor 440m is turned on by a high voltage level evaluation signal LEVAL. The address thirteen transistor 470a and address evaluation transistor 440m conduct to actively pull address line 472c to a low voltage level. The address thirteen transistor 470*b* and address evaluation transistor 440*m* conduct to actively pull address line 472*e* to a low voltage level.

The shift register 402 shifts a single high voltage level output signal from one shift register output signal line 410*a*-410*m* to the next shift register output signal line 410*a*-410*m*. Shift register 402 receives a control pulse in control signal CSYNC on control line 430 and a series of timing pulses from timing signals T1-T4 to shift the received control pulse into shift register 402. In response, shift register 402 provides a single high voltage level shift register output signal SO1 or SO13. All of the other shift register output signals SO1-SO13 are provided at low voltage levels. Shift register 402 receives another series of timing pulses from timing signals T1-T4 and shifts the single high voltage level output signal from one shift register output signal SO1-SO13 to the next shift register output signal SO1-SO13, with all other shift register output signals SO1-SO13 provided at low voltage levels. Shift register 402 receives a repeating series of timing pulses and in response to each series of timing pulses, shift register 402 shifts the single high voltage level output signal to provide a series of up to thirteen high voltage level shift register output signals SO1-SO13. Each high voltage level shift register output signal SO1-SO13 turns on two address transistor pairs 446, 448, . . . 470 to provide address signals ~A1, ~A2, . . . ~A7 to firing cells 120. The address signals ~A1, ~A2, . . . ~A7 are provided in thirteen address time slots that correspond to the thirteen shift register output signals SO1-SO13. In another embodiment, shift register 402 can include any suitable number of shift register output signals, such as fourteen, to provide address signals ~A1, ~A2, . . . ~A7 in any suitable number of address time slots, such as fourteen address time slots.

The shift register 402 receives direction signals from direction circuit 404 through direction signal lines 408. The direction signals set up the direction of shifting in shift register 402. The shift register 402 can be set to shift the high voltage level output signal in a forward direction, from shift register output signal SO1 to shift register output signal SO13, or in a reverse direction, from shift register output signal SO13 to shift register output signal SO1.

In the forward direction, shift register 402 receives the control pulse in control signal CSYNC and provides a high voltage level shift register output signal SO1. All other shift register output signals SO2-SO13 are provided at low voltage levels. Shift register 402 receives the next series of timing pulses and provides a high voltage level shift register output signal SO2, with all other shift register output signals SO1 and SO3-SO13 provided at low voltage levels. Shift register 402 receives the next series of timing pulses and provides a high voltage level shift register output signal SO3, with all other shift register output signals SO1, SO2, and SO4-SO13 provided at low voltage levels. Shift register 402 continues to shift the high level output signal in response to each series of timing pulses up to and including providing a high voltage level shift register output signal SO13, with all other shift register output signals SO1-SO12 provided at low voltage levels. After providing the high voltage level shift register output signal SO13, shift register 402 receives the next series of timing pulses and provides low voltage level signals for all shift register output signals SO1-SO13. Another control pulse in control signal CSYNC is provided to start or initiate shift register 402 shifting in the forward direction series of high voltage level output signals from shift register output signal SO1 to shift register output signal SO13.

In the reverse direction, shift register 402 receives a control pulse in control signal CSYNC and provides a high level shift register output signal SO13. All other shift register output signals SO1-SO12 are provided at low voltage levels. Shift register 402 receives the next series of timing pulses and provides a high voltage level shift register output signal SO12, with all other shift register output signals SO1-SO11 and SO13 provided at low voltage levels. Shift register 402 receives the next series of timing pulses and provides a high voltage level shift register output signal SO11, with all other shift register output signals SO1-SO10, SO12 and SO13 provided at low voltage levels. Shift register 402 continues to shift the high voltage level output signal in response to each series of timing pulses, up to and including providing a high voltage level shift register output signal SO1, with all other shift register output signals SO2-SO13 provided at low voltage levels. After providing the high voltage level shift register output signal SO1, shift register 402 receives the next series of timing pulses and provides low voltage level signals for all shift register output signals SO1-SO13. Another control pulse in control signal CSYNC is provided to start or initiate shift register 402 shifting in the reverse direction series of high voltage output signals from shift register output signal SO13 to shift register output signal SO1.

The direction circuit 404 provides two direction signals through direction signal lines 408. The direction signals set the forward/reverse shifting direction in shift register 402. Also, the direction signals can be used to clear the high voltage level output signal from shift register 402.

The direction circuit 404 receives a repeating series of timing pulses from timing signals T3-T6. In addition, direction circuit 404 receives control pulses in control signal CSYNC on control line 430. The direction circuit 404 provides forward direction signals in response to receiving a control pulse coincident with a timing pulse from timing signal T4. The forward direction signals set shift register 402 for shifting in the forward direction from shift register output signal SO1 to shift register output signal SO13. The direction circuit 404 provides reverse direction signals in response to receiving a control pulse coincident with a timing pulse from timing signal T6. The reverse direction signals set shift register 402 for shifting in the reverse direction, from shift register output signal SO13 to shift register output signal SO1. Direction circuit 404 provides direction signals that clear shift register 402 in response to direction circuit 404 receiving control pulses coincident with both a timing pulse from timing signal T4 and a timing pulse from timing signal T6.

The logic array 406 receives shift register output signals SO1-SO13 on shift register output signal lines 410*a*-410*m* and timing pulses from timing signals T3-T5 on timing signal lines 434, 422 and 436. In response to a single high voltage level output signal in the shift register output signals SO1-SO13 and the timing pulses from timing signals T3-T5, logic array 406 provides two low voltage level address signals out of the seven address signals ~A1, ~A2, . . . ~A7.

The logic array 406 receives a timing pulse from timing signal T3 that turns on evaluation prevention transistor 442*a* to pull the evaluation signal line 474 to a low voltage level and turn off address evaluation transistors 440. Also, the timing pulse from timing signal T3 charges address lines 472*a*-472*g* to high voltage levels through address line pre-charge transistors 438. In one embodiment, the timing pulse from timing signal T3 is replaced by the timing pulse from timing signal T4 to charge address lines 472*a*-472*g* to high voltage levels through address line pre-charge transistors 438.

The timing pulse from timing signal T4 turns on evaluation prevention transistor 442*b* to pull evaluation signal line 474 to a low voltage level and turn off address evaluation transistors 440. The shift register output signals SO1-SO13 settle to valid output signals during the timing pulse from timing signal T4.

A single high voltage level output signal in the shift register output signals SO1-SO13 is provided to the gates of an address transistor pair 446, 448, . . . 470 in logic array 406. A timing pulse from timing signal T5 charges the evaluation signal line 474 to a high voltage level to turn on address evaluation transistors 440. As address evaluation transistors 440 are turned on, an address transistor pair 446, 448, . . . or 470 in logic array 406 that receive the high voltage level shift register output signal SO1-SO13 conduct to discharge the corresponding address lines 472. The corresponding address lines 472 are actively pulled low through conducting address transistor pairs 446, 448, . . . 470 and a conducting address evaluation transistor 440. The other address lines 472 remain charged to a high voltage level.

The logic array 406 provides two low voltage level address signals out of the seven address signals ~A1, ~A2, . . . ~A7 in each address time slot. If shift register output signal SO1 is at a high voltage level, address one transistors 446a and 446b conduct to pull address lines 472a and 472b to low voltage levels and provide active low address signals ~A1 and ~A2. If shift register output signal SO2 is at a high voltage level, address two transistors 448a and 448b conduct to pull address lines 472a and 472c to low voltage levels and provide active low address signals ~A1 and ~A3. If shift register output signal SO3 is at a high voltage level, address three transistors 450a and 450b conduct to pull address lines 472a and 472d to low voltage levels and provide active low address signals ~A1 and ~A4, and so on for each shift register output signal SO4-SO13. The address signals ~A1, ~A2, . . . ~A7 for each of the thirteen address time slots, which correlate to the shift register output signals SO1-SO13, are set out in the following table:

| Address Time Slot | Active address signals |
| --- | --- |
| 1 | ~A1 and ~A2 |
| 2 | ~A1 and ~A3 |
| 3 | ~A1 and ~A4 |
| 4 | ~A1 and ~A5 |
| 5 | ~A1 and ~A6 |
| 6 | ~A1 and ~A7 |
| 7 | ~A2 and ~A3 |
| 8 | ~A2 and ~A4 |
| 9 | ~A2 and ~A5 |
| 10 | ~A2 and ~A6 |
| 11 | ~A2 and ~A7 |
| 12 | ~A3 and ~A4 |
| 13 | ~A3 and ~A5 |

In another embodiment, logic array 406 can provide active address signals ~A1, ~A2, . . . ~A7 for each of thirteen address time slots as set out in the following table:

| Address Time Slot | Active address signals |
| --- | --- |
| 1 | ~A1 and ~A3 |
| 2 | ~A1 and ~A4 |
| 3 | ~A1 and ~A5 |
| 4 | ~A1 and ~A6 |
| 5 | ~A2 and ~A4 |
| 6 | ~A2 and ~A5 |
| 7 | ~A2 and ~A6 |
| 8 | ~A2 and ~A7 |
| 9 | ~A3 and ~A5 |
| 10 | ~A3 and ~A6 |
| 11 | ~A3 and ~A7 |
| 12 | ~A4 and ~A6 |
| 13 | ~A4 and ~A7 |

Also, in other embodiments, the logic array 406 can include address transistors that provide any suitable number of low voltage level address signals ~A1, ~A2, . . . ~A7 for each high voltage level output signal SO1-SO13 and in any suitable sequence of low voltage level address signals ~A1, ~A2, . . . ~A7. This can be done by, for example, appropriately locating each transistor pair 446, 448, . . . 470 to discharge any two desired address lines 672a-g.

In addition, in other embodiments, logic array 406 can include any suitable number of address lines to provide any suitable number of address signals in any suitable number of address timeslots.

In operation, a repeating series of six timing pulses is provided from timing signals T1-T6. Each of the timing signals T1-T6 provides one timing pulse in each series of six timing pulses. The timing pulse from timing signal T1 is followed by the timing pulse from timing signal T2, followed by the timing pulse from timing signal T3, followed by the timing pulse from timing signal T4, followed by the timing pulse from timing signal T5, which is followed by the timing pulse from timing signal T6. The series of six timing pulses is repeated in the repeating series of six timing pulses.

In one series of the six timing pulses, direction circuit 404 receives a timing pulse from timing signal T3 in fourth pre-charge signal PRE4. The timing pulse in fourth pre-charge signal PRE4 charges a first one of the direction lines 408 to a high voltage level. The direction circuit 404 receives a reduced voltage level timing pulse from timing signal T4 in fourth evaluation signal EVAL4. If direction circuit 404 receives a control pulse in control signal CSYNC coincident with (at the same time as) the fourth evaluation signal EVAL4, direction circuit 404 discharges the first direction line 408. If direction 404 receives a low voltage level control signal CSYNC coincident with the timing pulse in the fourth evaluation signal EVAL4, the first direction line 408 remains charged to a high voltage level.

Next, direction circuit 404 receives a timing pulse from timing signal T5 in third pre-charge signal PRE3. The timing pulse in third pre-charge signal PRE3 charges a second one of the direction lines 408. The direction circuit 404 receives a reduced voltage level timing pulse from timing signal T6 in third evaluation signal EVAL3. If the direction circuit 404 receives a control pulse in control signal CSYNC coincident with a timing pulse in third evaluation signal EVAL3, direction circuit 404 discharges the second direction line 408 to a low voltage level. If direction circuit 404 receives a low voltage level control signal CSYNC coincident with the timing pulse in third evaluation signal EVAL3, the second direction line 408 remains charged to a high voltage level.

If the first direction line 408 is discharged to a low voltage level and the second direction line 408 remains at a high voltage level, the signal levels on the first and second direction lines 408 set up shift register 402 to shift in the forward direction. If the first direction line 408 remains at a high voltage level and the second direction line 408 is discharged to a low voltage level, the signal levels on direction lines 408 set up shift register 402 to shift in the reverse direction. If both the first and second direction lines 408 are discharged to low voltage levels, shift register 402 is prevented from providing a high voltage level shift register output signal SO1-SO13. The direction signals on direction lines 408 are set during each series of six timing pulses.

To begin, the direction is set in one series of six timing pulses and shift register 402 is initiated in the next series of six timing pulses. To initiate shift register 402, shift register 402 receives a timing pulse from timing signal T1 in first pre-charge signal PRE1. The timing pulse in first pre-charge signal PRE1 pre-charges an internal node in each of the thirteen shift register cells, indicated at 403a-403m. The shift register 402 receives a reduced voltage level timing pulse from timing signal T2 in first evaluation signal EVAL1. If a control pulse in control signal CSYNC is received by shift register 402 coincident with the timing pulse in first evaluation signal EVAL1, shift register 402 discharges the internal node of one of the thirteen shift register cells to provide a low voltage level at the discharged internal node. If the control signal CSYNC remains at a low voltage level coincident with the timing pulse in first evaluation signal EVAL1, the internal node in each of the thirteen shift register cells remains at a high voltage level.

Shift register 402 receives a timing pulse from timing signal T3 in second pre-charge signal PRE2. The timing pulse in second pre-charge signal PRE2 pre-charges each of the thirteen shift register output lines 410a-410m to provide high voltage level shift register output signals SO1-SO13. Shift register 402 receives a reduced voltage level timing pulse from timing signal T4 in second evaluation signal EVAL2. If the internal node in a shift register cell 403 is at a low voltage level, such as after receiving the control pulse from control signal CSYNC coincident with the timing pulse in first evaluation signal EVAL1, shift register 402 maintains the shift register output signal SO1-SO13 at the high voltage level. If the internal node in a shift register cell 403 is at a high voltage level, such as in all other shift register cells 403, shift register 402 discharges the shift register output line 410a-410m to provide low voltage level shift register output signals SO1-SO13. The shift register 402 is initiated in one series of the six timing pulses. The shift register output signals SO1-SO13 become valid during the timing pulse from timing signal T4 in second evaluation signal EVAL2 and remain valid until the timing pulse from timing signal T3 in the next series of six timing pulses. In each subsequent series of the six timing pulses, shift register 402 shifts the high voltage level shift register output signal SO1-SO13 from one shift register cell 403 to the next shift register cell 403.

The logic array 406 receives the shift register output signals SO1-SO13. In one embodiment, logic array 406 receives the timing pulse from timing signal T3 to pre-charge address lines 472 and turn off address evaluation transistors 440. In one embodiment, logic array 406 receives the timing pulse from timing signal T3 to turn off address evaluation transistors 440 and a timing pulse from timing signal T4 to pre-charge address lines 472.

Logic array 406 receives the timing pulse from timing signal T4 to turn off address evaluation transistors 440 as shift register output signals SO1-SO13 settle to valid shift register output signals SO1-SO13. If shift register 402 is initiated, one shift register output signal SO1-SO13 remains at a high voltage level after the timing pulse from timing signal T4. Logic array 406 receives the timing pulse from timing signal T5 to charge evaluation signal line 474 and turn on address evaluation transistor 440. The address transistor pair 446, 448, ... 470 that receives the high voltage level shift register output signal SO1-SO13 are turned on to pull two of the seven address lines 472a-472g to low voltage levels. The two low voltage level address signals in address signals ~A1, ~A2, ... ~A7 are used to enable firing cells 120 and firing cell subgroups for activation. The address signals ~A1, ~A2, ... ~A7 become valid during the timing pulse from timing signal T5 and remain valid until the timing pulse from timing signal T3 in the next series of six timing pulses.

If shift register 402 is not initiated, all shift register output lines 410 are discharged to provide low voltage level shift register output signals SO1-SO13. The low voltage level shift register output signals SO1-SO13 turns off address transistor pairs 446, 448, ... 470 and address lines 472 remain charged to provide high voltage level address signals ~A1, ~A2, ... ~A7. The high voltage level address signals ~A1, ~A2, ... ~A7 prevent firing cells 120 and firing cell subgroups from being enabled for activation.

While FIG. 9 describes one embodiment of an address circuit, other embodiments employing different logic elements and components may be utilized. For example, a controller that receives the above described input signals, e.g. signal T1-T6 and that provides address signals ~A1, ~A2, ... ~A7 may be utilized.

Figure 10A:
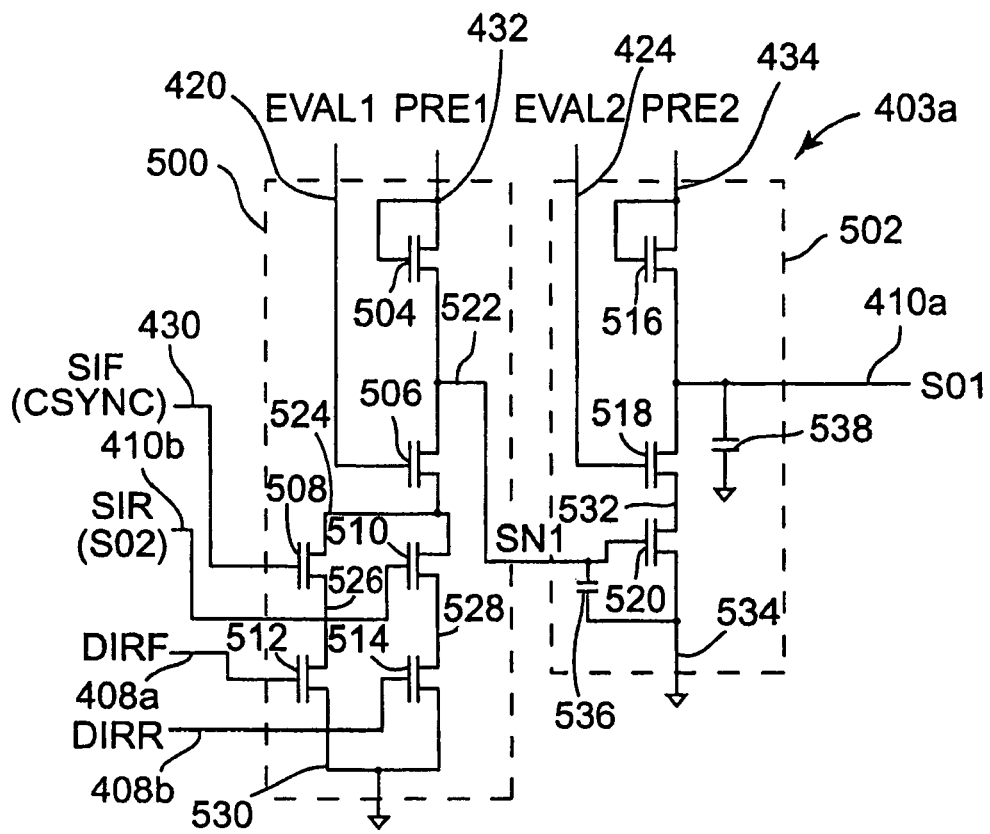
FIG. 10A is a diagram illustrating one shift register cell in a shift register.

FIG. 10A is a diagram illustrating one shift register cell 403a in shift register 402. Shift register 402 includes thirteen shift register cells 403a-403m that provide the thirteen shift register output signals SO1-SO13. Each shift register cell 403a-403m provides one of the shift register output signals SO1-SO13 and each shift register cell 403a-403m is similar to shift register cell 403a. The thirteen shift register cells 403 are electrically coupled in series to provide shifting in the forward and reverse directions. In other embodiments, shift register 402 can include any suitable number of shift register cells 403 to provide any suitable number of shift register output signals.

The shift register cell 403a includes a first stage that is an input stage, indicated with dashed lines at 500, and a second stage that is an output stage, indicated with dashed lines at 502. The first stage 500 includes a first pre-charge transistor 504, a first evaluation transistor 506, a forward input transistor 508, a reverse input transistor 510, a forward direction transistor 512 and a reverse direction transistor 514. The second stage 502 includes a second pre-charge transistor 516, a second evaluation transistor 518 and an internal node transistor 520.

In the first stage 500, the gate and one side of the drain-source path of first pre-charge transistor 504 is electrically coupled to timing signal line 432. The timing signal line 432 provides timing signal T1 to shift register 402 as first pre-charge signal PRE1. The other side of the drain-source path of first pre-charge transistor 504 is electrically coupled to one side of the drain-source path of first evaluation transistor 506 and the gate of internal node transistor 520 through internal node 522. The internal node 522 provides shift register internal node signal SN1 between stages 500 and 502 to the gate of internal node transistor 520.

The gate of first evaluation transistor 506 is electrically coupled to first evaluation signal line 420. The first evaluation signal line 420 provides the reduced voltage level T2 timing signal to shift register 402 as first evaluation signal EVAL1. The other side of the drain-source path of first evaluation transistor 506 is electrically coupled to one side of the drain-source path of forward input transistor 508 and one side of the drain-source path of reverse input transistor 510 through internal path 524.

The other side of the drain-source path of forward input transistor 508 is electrically coupled to one side of the drain-source path of forward direction transistor 512 at 526, and the other side of the drain-source path of reverse input transistor 510 is electrically coupled to one side of the drain-source path of reverse direction transistor 514 at 528. The drain-source paths of forward direction transistor 512 and reverse direction transistor 514 are electrically coupled to a reference, such as ground, at 530.

The gate of the forward direction transistor 512 is electrically coupled to direction line 408a that receives the forward direction signal DIRF from direction circuit 404. The gate of the reverse direction transistor 514 is electrically coupled to direction line 408b that receives the reverse direction signal DIRR from direction circuit 404.

In the second stage 502, the gate and one side of the drain-source path of second pre-charge transistor 516 are electrically coupled to timing signal line 434. The timing signal line 434 provides timing signal T3 to shift register 402 as second pre-charge signal PRE2. The other side of the drain-source path of second pre-charge transistor 516 is electrically coupled to one side of the drain-source path of second evaluation transistor 518 and to shift register output line 410a. The other side of the drain-source path of second evaluation transistor 518 is electrically coupled to one side of the drain-source path of internal node transistor 520 at 532. The gate of second evaluation transistor 518 is electrically coupled to second evaluation signal line 424 to provide the reduced voltage level T4 timing signal to shift register 402 as second evaluation signal EVAL2. The gate of internal node transistor 520 is electrically coupled to internal node 522 and the other side of the drain-source path of internal node transistor 520 is electrically coupled to a reference, such as ground, at 534. The gate of the internal node transistor 520 includes a capacitance at 536 for storing the shift register cell internal node signal SN1. The shift register output signal line 410a includes a capacitance at 538 for storing the shift register output signal SO1.

Each shift register cell 403a-403m in the series of thirteen shift register cells 403 is similar to shift register cell 403a. The gate of the forward direction transistor 508 in each shift register cell 403a-403m is electrically coupled to the control line 430 or one of the shift register output lines 410a-410l to shift in the forward direction. The gate of the reverse direction transistor 510 in each shift register cell 403a-403m is electrically coupled to the control line 430 or one of the shift register output lines 410b-410m to shift in the reverse direction. The shift register output signal lines 410 are electrically coupled to one forward transistor 508 and one reverse transistor 510, except for shift register output signal lines 410a and 410m. Shift register output signal line 410a is electrically coupled to a forward direction transistor 508 in shift register cell 403b, but not a reverse direction transistor 510. Shift register output signal line 410m is electrically coupled to a reverse direction transistor 510 in shift register cell 403l, but not a forward direction transistor 508.

The shift register cell 403a is the first shift register 403 in the series of thirteen shift registers 403 as shift register 402 shifts in the forward direction. The gate of forward input transistor 508 in shift register cell 403a is electrically coupled to control signal line 430 to receive control signal CSYNC. The second shift register cell 403b includes the gate of the forward input transistor electrically coupled to shift register output line 410a to receive shift register output signal SO1. The third shift register cell 403c includes the gate of the forward input transistor electrically coupled to shift register output line 410b to receive shift register output signal SO2. The fourth shift register cell 403d includes the gate of the forward input transistor electrically coupled to shift register output line 410c to receive shift register output signal SO3. The fifth shift register cell 403e includes the gate of the forward input transistor electrically coupled to shift register output line 410d to receive shift register output signal SO4. The sixth shift register cell 403f includes the gate of the forward input transistor electrically coupled to shift register output line 410e to receive shift register output signal SO5. The seventh shift register cell 403g includes the gate of the forward input transistor electrically coupled to shift register output line 410f to receive shift register output signal SO6. The eighth shift register cell 403h includes the gate of the forward input transistor electrically coupled to shift register output line 410g to receive shift register output signal SO7. The ninth shift register cell 403i includes the gate of the forward input transistor electrically coupled to shift register output line 410h to receive shift register output signal SO8. The tenth shift register cell 403j includes the gate of the forward input transistor electrically coupled to shift register output line 410i to receive shift register output signal SO9. The eleventh shift register cell 403k includes the gate of the forward input transistor electrically coupled to shift register output line 410j to receive shift register output signal SO10. The twelfth shift register cell 403l includes the gate of the forward input transistor electrically coupled to shift register output line 410k to receive shift register output signal SO11. The thirteenth shift register cell 403m includes the gate of the forward input transistor electrically coupled to shift register output line 410l to receive shift register output signal SO12.

The shift register cell 403a is the last shift register cell 403 in the series of thirteen shift register cells 403 as shift register 402 shifts in the reverse direction. The gate of reverse input transistor 510 in shift register cell 403a is electrically coupled to the preceding shift register output line 410b to receive shift register output signal SO2. The shift register cell 403b includes the gate of the reverse input transistor electrically coupled to shift register output line 410c to receive shift register output signal SO3. The shift register cell 403c includes the gate of the reverse input transistor electrically coupled to shift register output line 410d to receive shift register output signal SO4. The shift register cell 403d includes the gate of the reverse input transistor electrically coupled to shift register output line 410e to receive shift register output signal SO5. The shift register cell 403e includes the gate of the reverse input transistor electrically coupled to shift register output line 410f to receive shift register output signal SO6. The shift register cell 403f includes the gate of the reverse input transistor electrically coupled to shift register output line 410g to receive shift register output signal SO7. The shift register cell 403g includes the gate of the reverse input transistor electrically coupled to shift register output line 410h to receive shift register output signal SO8. The shift register cell 403h includes the gate of the reverse input transistor electrically coupled to shift register output line 410i to receive shift register output signal SO9. The shift register cell 403i includes the gate of the reverse input transistor electrically coupled to shift register output line 410j to receive shift register output signal SO10. The shift register cell 403j includes the gate of the reverse input transistor electrically coupled to shift register output line 410k to receive shift register output signal SO11. The shift register cell 403k includes the gate of the reverse input transistor electrically coupled to shift register output line 410l to receive shift register output signal SO12. The shift register cell 403l includes the gate of the reverse input transistor electrically coupled to shift register output line 410m to receive shift register output signal SO13. The shift register cell 403m includes the gate of the reverse input transistor electrically coupled to control signal line 430 to receive control signal CSYNC. Shift register output lines 410a-410m are also electrically coupled to logic array 406.

Shift register 402 receives a control pulse in control signal CSYNC and provides a single high voltage level output signal. As described above and described in detail below, the shifting direction of shift register 402 is set in response to direction signals DIRF and DIRR, which are generated during timing pulses in timing signals T3-T6 based on the control signal CSYNC on control signal line 430. If shift register 402 is shifting in the forward direction, shift register 402 sets shift register output line 410*a* and shift register output signal SO1 to a high voltage level in response to the control pulse and timing pulses on timing signals T1-T4. If shift register 402 is shifting in the reverse direction, shift register 402 sets shift register output line 410*m* and shift register output signal SO13 to a high voltage level in response to the control pulse and timing pulses in timing signal T1-T4. The high voltage level output signal SO1 or SO13 is shifted through shift register 402 from one shift register cell 403 to the next shift register cell 403 in response to timing pulses in timing signals T1-T4.

The shift register 402 shifts in the control pulse and shifts the single high level output signal from one shift register cell 403 to the next shift register cell 403 using two pre-charge operations and two evaluate operations. The first stage 500 of each shift register cell 403 receives forward direction signal DIRF and reverse direction signal DIRR. Also, the first stage 500 of each shift register 403 receives a forward shift register input signal SIF and a reverse shift register input signal SIR. All shift register cells 403 in shift register 402 are set to shift in the same direction and at the same time as timing pulses are received in timing signals T1-T4.

The first stage 500 of each shift register cell 403 shifts in either the forward shift register input signal SIF or the reverse shift register input signal SIR. The high or low voltage level of the selected shift register input signal SIF or SIR is provided as the shift register output signal SO1-SO13. The first stage 500 of each shift register cell 403 pre-charges internal node 522 during a timing pulse from timing signal T1 and evaluates the selected shift register input signal SIF or SIR during a timing pulse from timing signal T2. The second stage 502 in each shift register cell 403 pre-charges shift register output lines 410*a*-410*m* during a timing pulse from timing signal T3 and evaluates the internal node signal SN (e.g., SN1) during a timing pulse from timing signal T4.

The direction signals DIRF and DIRR set the forward/reverse direction of shifting in shift register cell 403*a* and all other shift register cells 403 in shift register 402. Shift register 402 shifts in the forward direction if forward direction signal DIRF is at a high voltage level and reverse direction signal DIRR is at a low voltage level. Shift register 402 shifts in the reverse direction if reverse direction signal DIRR is at a high voltage level and forward direction signal DIRF is at a low voltage level. If both direction signals DIRF and DIRR are at low voltage levels, shift register 402 does not shift in either direction and all shift register output signals SO1-SO13 are cleared to inactive low voltage levels.

In operation of shifting shift register cell 403*a* in the forward direction, forward direction signal DIRF is set to a high voltage level and reverse direction signal DIRR is set to a low voltage level. The high voltage level forward direction signal DIRF turns on forward direction transistor 512 and the low voltage level reverse direction signal DIRR turns off reverse direction transistor 514. A timing pulse from timing signal T1 is provided to shift register 402 in first pre-charge signal PRE1 to charge internal node 522 to a high voltage level through first pre-charge transistor 504. Next, a timing pulse from timing signal T2 is provided to resistor divide network 412 and a reduced voltage level T2 timing pulse is provided to shift register 402 in first evaluation signal EVAL1. The timing pulse in first evaluation signal EVAL1 turns on first evaluation transistor 506. If the forward shift register input signal SIF is at a high voltage level, forward input transistor 508 is turned on and with forward direction transistor 512 already turned on, internal node 522 is discharged to provide a low voltage level internal node signal SN1. The internal node 522 is discharged through first evaluation transistor 506, forward input transistor 508 and forward direction transistor 512. If the forward shift register input signal SIF is at a low voltage level, forward input transistor 508 is turned off and internal node 522 remains charged to provide a high voltage level internal node signal SN1. Reverse shift register input signal SIR controls reverse input transistor 510. However, reverse direction transistor 514 is turned off such that internal node 522 cannot be discharged through reverse input transistor 510.

The internal node signal SN1 on internal node 522 controls internal node transistor 520. A low voltage level internal node signal SN1 turns off internal node transistor 520 and a high voltage level internal node signal SN1 turns on internal node transistor 520.

A timing pulse from timing signal T3 is provided to shift register 402 as second pre-charge signal PRE2. The timing pulse in second pre-charge signal PRE2 charges shift register output line 410*a* to a high voltage level through second pre-charge transistor 516. Next, a timing pulse from timing signal T4 is provided to a resistor divide network 414 and a reduced voltage level T4 timing pulse is provided to shift register 402 as second evaluation signal EVAL2. The timing pulse in second evaluation signal EVAL2 turns on second evaluation transistor 518. If internal node transistor 520 is off, shift register output line 410*a* remains charged to a high voltage level. If internal node transistor 520 is on, shift register output line 410*a* is discharged to a low voltage level. The shift register output signal SO1 is the high/low inverse of the internal node signal SN1, which was the high/low inverse of the forward shift register input signal SIF. The level of the forward shift register input signal SIF was shifted to the shift register output signal SO1.

In shift register cell 403*a*, the forward shift register input signal SIF is control signal CSYNC on control line 430. To discharge internal node 522 to a low voltage level, a control pulse in control signal CSYNC is provided at the same time as a timing pulse in first evaluation signal EVAL1. The control pulse in control signal CSYNC that is coincident with the timing pulse from timing signal T2 initiates shift register 402 for shifting in the forward direction.

In operation of shifting shift register cell 403*a* in the reverse direction, forward direction signal DIRF is set to a low voltage level and reverse direction signal DIRR is set to a high voltage level. The low voltage level forward direction signal DIRF turns off forward direction transistor 512 and the high voltage level reverse direction signal DIRR turns on reverse direction transistor 514. A timing pulse from timing signal T1 is provided in first pre-charge signal PRE1 to charge internal node 522 to a high voltage level through first pre-charge transistor 504. Next, a timing pulse from timing signal T2 is provided to resistor divide network 412 and a reduced voltage level T2 timing pulse is provided in first evaluation signal EVAL1. The timing pulse in first evaluation signal EVAL1 turns on first evaluation transistor 506. If the reverse shift register input signal SIR is at a high voltage level, reverse input transistor 510 is turned on, and with reverse direction transistor 514 already turned on, internal node 522 is discharged to provide a low voltage level internal node signal SN1. The internal node 522 is discharged through first evaluation transistor 506, reverse input transistor 510 and reverse direction transistor 514. If the reverse shift register input signal SIR is at a low voltage level, reverse input transistor 510 is turned off and internal node 522 remains charged to provide a high voltage level internal node signal SN1. Forward shift register input signal SIF controls forward input transistor 508. However, forward direction transistor 512 is turned off such that internal node 522 cannot be discharged through forward input transistor 508.

A timing pulse from timing signal T3 is provided in second pre-charge signal PRE2. The timing pulse in second pre-charge signal PRE2 charges shift register output line 410*a* to a high voltage level through second pre-charge resistor 516. Next a timing pulse from timing signal T4 is provided to resistor divide network 414 and a reduced voltage level T4 timing pulse is provided in second evaluation signal EVAL2. The timing pulse in second evaluation signal EVAL2 turns on second evaluation transistor 518. If internal node transistor 520 is off, shift register output line 410*a* remains charged to a high voltage level. If internal node transistor 520 is on, shift register output line 410*a* is discharged to a low voltage level. The shift register output signal SO1 is the high/low inverse of the internal node signal SN1, which was the high/low inverse of the reverse shift register input signal SIR. The level of the reverse shift register input signal SIR was shifted to the shift register output signal SO1.

In shift register cell 403*a*, the reverse shift register input signal SIR is shift register output signal SO2 on shift register output line 410*b*. In shift register cell 403*m*, the reverse shift register input signal SIR is control signal CSYNC on control line 430. To discharge internal node 522 in shift register cell 403*m* to a low voltage level, a control pulse in control signal CSYNC is provided at the same time as a timing pulse in the first evaluation signal EVAL1. The control pulse in control signal CSYNC that is coincident with the timing pulse from timing signal T2 initiates shift register 402 for shifting in the reverse direction from shift register cell 403*m* toward shift register cell 403*a*.

In operation of clearing shift register cell 403*a* and all shift register cells 403 in shift register 402, direction signals DIRF and DIRR are set to low voltage levels. A low voltage forward direction signal DIRF turns off forward direction transistor 512 and a low voltage level reverse direction signal DIRR turns off reverse direction transistor 514. A timing pulse from timing signal T1 is provided in first pre-charge signal PRE1 to charge internal node 522 and provide a high voltage level internal node signal SN1. A timing pulse from timing signal T2 is provided as a reduced voltage level T2 timing pulse in first evaluation signal EVAL1 to turn on first evaluation transistor 506. Both forward direction transistor 512 and reverse direction transistor 514 are turned off such that internal node 522 is not discharged through either forward input transistor 508 or reverse input transistor 510.

The high voltage level internal node signal SN1 turns on internal node transistor 520. A timing pulse from timing signal T3 is provided in second pre-charge signal PRE2 to charge shift register output signal line 410*a* and all shift register output signal lines 410. Next, a timing pulse from timing signal T4 is provided as a reduced voltage level T4 timing pulse in second evaluation signal EVAL2 to turn on second evaluation transistor 518. The shift register output line 410*a* is discharged through second evaluation transistor 518 and internal node transistor 520 to provide a low voltage level shift register output signal SO1. Also, all other shift register output lines 410 are discharged to provide inactive low voltage level shift register output signals SO2-SO13.

Figure 10B:
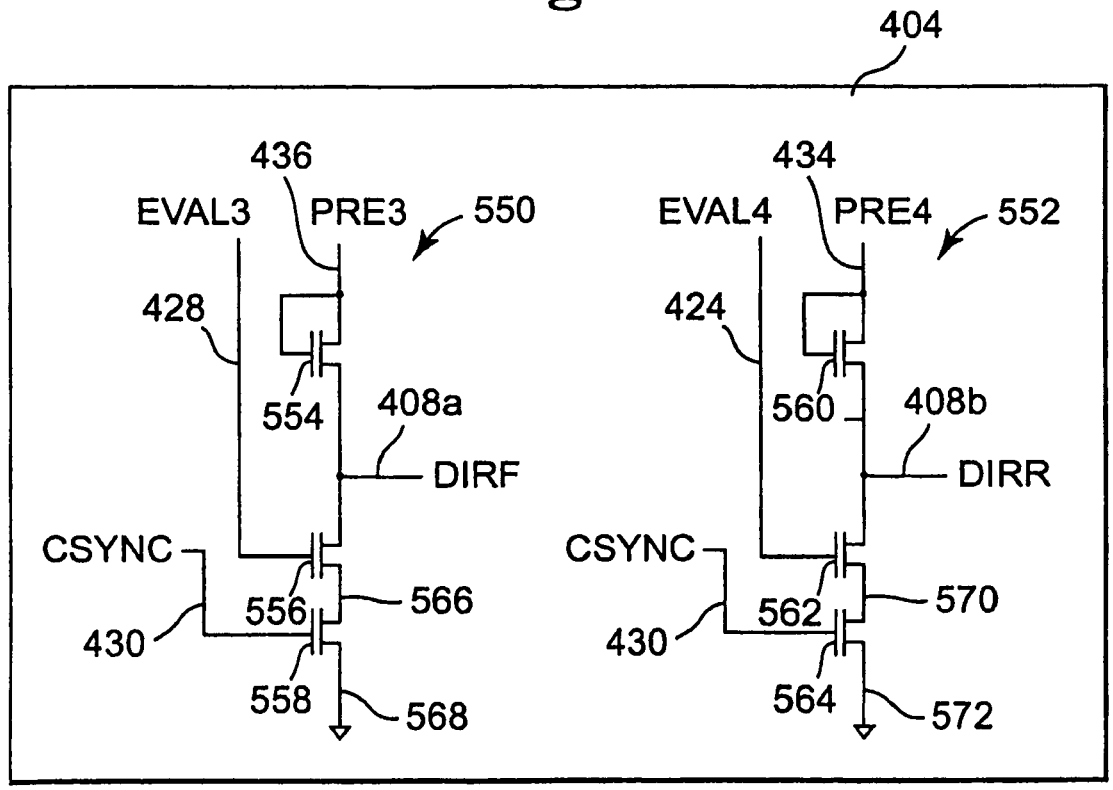
FIG. 10B is a diagram illustrating a direction circuit.

FIG. 10B is a diagram illustrating direction circuit 404. The direction circuit 404 includes a forward direction signal circuit 550 and a reverse direction signal circuit 552. The forward direction signal circuit 550 includes a third pre-charge transistor 554, a third evaluation transistor 556 and a first control transistor 558. The reverse direction signal circuit 552 includes a fourth pre-charge transistor 560, a fourth evaluation transistor 562 and a second control transistor 564.

The gate and one side of the drain-source path of third pre-charge transistor 554 are electrically coupled to timing signal line 436. The timing signal line 436 provides timing signal T5 to direction circuit 404 as third pre-charge signal PRE3. The other side of the drain-source path of third pre-charge transistor 554 is electrically coupled to one side of the drain-source path of third evaluation transistor 556 through direction signal line 408*a*. The direction signal line 408*a* provides the forward direction signal DIRF to the gate of the forward direction transistor in each shift register cell 403 in shift register 402, such as the gate of forward direction transistor 512 in shift register cell 403*a*. The gate of third evaluation transistor 556 is electrically coupled to the third evaluation signal line 428 that provides the reduced voltage level T6 timing signal to direction circuit 404. The other side of the drain-source path of third evaluation transistor 556 is electrically coupled to the drain-source path of control transistor 558 at 566. The drain-source path of control transistor 558 is also electrically coupled to a reference, such as ground, at 568. The gate of control transistor 558 is electrically coupled to control line 430 to receive control signal CSYNC.

The gate and one side of the drain-source path of fourth pre-charge transistor 560 are electrically coupled to timing signal line 434. The timing signal line 434 provides timing signal T3 to direction circuit 404 as fourth pre-charge signal PRE4. The other side of the drain-source path of fourth pre-charge transistor 560 is electrically coupled to one side of the drain-source path of fourth evaluation transistor 562 through direction signal line 408*b*. The direction signal line 408*b* provides the reverse direction signal DIRR to the gate of the reverse direction transistor in each shift register cell 403 in shift register 402, such as the gate of reverse direction transistor 514 in shift register cell 403*a*. The gate of fourth evaluation transistor 562 is electrically coupled to the fourth evaluation signal line 424 that provides the reduced voltage level T4 timing signal to direction circuit 404. The other side of the drain-source path of fourth evaluation transistor 562 is electrically coupled to the drain-source path of control transistor 564 at 570. The drain-source path of control transistor 564 is also electrically coupled to a reference, such as ground, at 572. The gate of control transistor 564 is electrically coupled to control line 430 to receive control signal CSYNC.

The direction signals DIRF and DIRR set the direction of shifting in shift register 402. If forward direction signal DIRF is set to a high voltage level and reverse direction signal DIRR is set to a low voltage level, forward direction transistors, such as forward direction transistor 512, are turned on and reverse direction transistors, such as reverse direction transistor 514, are turned off. Shift register 402 shifts in the forward direction. If forward direction signal DIRF is set to a low voltage level and reverse direction signal DIRR is set to a high voltage level, forward direction transistors, such as forward direction transistor 512, are turned off and reverse direction transistors, such as reverse direction transistor 514 are turned on. Shift register 402 shifts in the reverse direction. The direction signals DIRF and DIRR are set during each series of timing pulses from timing signal T3-T6 as shift register 402 actively shifts in either the forward or reverse direction. To terminate shifting or prevent shifting of shift register 402, direction signals DIRF and DIRR are set to low voltage levels. This clears the single high voltage level signal from the shift register output signals SO1-SO13, such that all shift register output signals SO1-SO13 are at low voltage levels. The low voltage level shift register output signals SO1-SO13 turn off all address transistor pairs 446, 448, . . . 470 and address signals ~A1, ~A2, . . . ~A7 remain at high voltage levels that do not enable firing cells 120.

In operation, timing signal line 434 provides a timing pulse from timing signal T3 to direction circuit 404 in fourth precharge signal PRE4. The timing pulse in fourth pre-charge signal PRE4 charges the reverse direction signal line 408b to a high voltage level. A timing pulse from timing signal T4 is provided to the resistor divide network 414 that provides a reduced voltage level T4 timing pulse to direction circuit 404 in fourth evaluation signal EVAL4. The timing pulse in fourth evaluation signal EVAL4 turns on fourth evaluation transistor 562. If a control pulse from control signal CSYNC is provided to the gate of control transistor 564 at the same time as the timing pulse in fourth evaluation signal EVAL4 is provided to fourth evaluation transistor 562, the reverse direction signal line 408b discharges to a low voltage level. If the control signal CSYNC remains at a low voltage level as the timing pulse in the fourth evaluation signal EVAL4 is provided to fourth evaluation transistor 562, the reverse direction signal line 408b remains charged to a high voltage level.

Timing signal line 436 provides a timing pulse from timing signal T5 to direction circuit 404 in third pre-charge signal PRE3. The timing pulse in third pre-charge signal PRE3 charges the forward direction signal line 408a to a high voltage level. A timing pulse from timing signal T6 is provided to resistor divide network 416 that provides a reduced voltage level T6 timing pulse to direction circuit 404 in third evaluation circuit EVAL3. The timing pulse in third evaluation signal EVAL3 turns on third evaluation transistor 556. If a control pulse from control signal CSYNC is provided to the gate of control transistor 558 at the same time as the timing pulse in third evaluation signal EVAL3 is provided to third evaluation transistor 556, the forward direction signal line 408a discharges to a low voltage level. If the control signal CSYNC remains at a low voltage level as the timing pulse in the third evaluation signal EVAL3 is provided to third evaluation transistor 556, the forward direction signal line 408a remains charged to a high voltage level.

Figure 11:
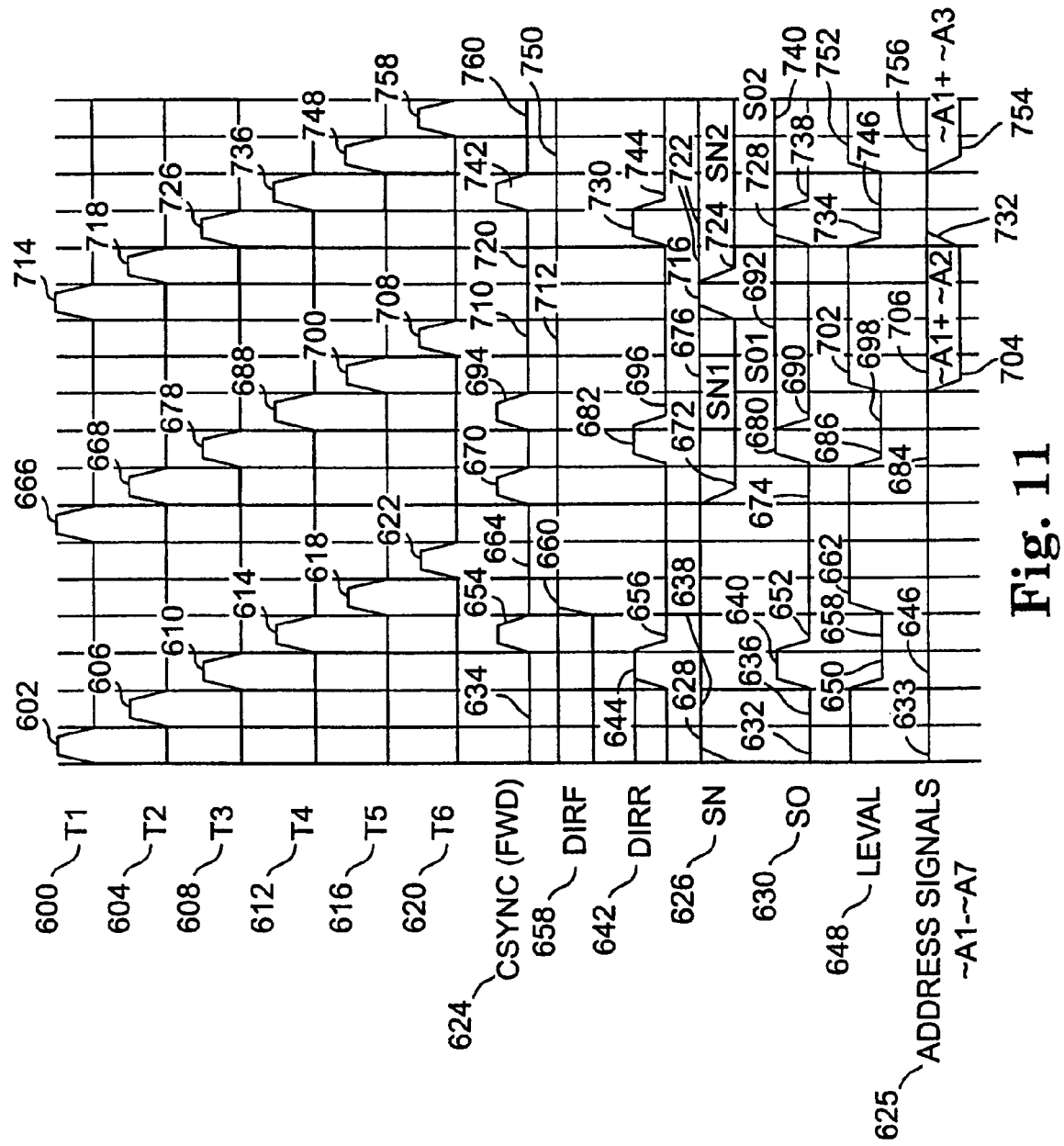
FIG. 11 is a timing diagram illustrating operation of an address generator in the forward direction.

FIG. 11 is a timing diagram illustrating operation of address generator 400 in the forward direction. The timing signals T1-T6 provide a series of six repeating pulses. Each of the timing signals T1-T6 provides one pulse in the series of six pulses.

In one series of six pulses, timing signal T1 at 600 includes timing pulse 602, timing signal T2 at 604 includes timing pulse 606, timing signal T3 at 608 includes timing pulse 610, timing signal T4 at 612 includes timing pulse 614, timing signal T5 at 616 includes timing pulse 618 and timing signal T6 at 620 includes timing pulse 622. The control signal CSYNC at 624 includes control pulses that set the direction of shifting in shift register 402 and initiate shift register 402 for generating address signals ~A1, ~A2, . . . ~A7, indicated at 625.

The timing pulse 602 of timing signal T1 at 600 is provided to shift register 402 in first pre-charge signal PRE1. During timing pulse 602, internal node 522, in each of the shift register cells 403a-403m, charges to provide high voltage level internal node signals SN1-SN13. All shift register internal node signals SN, indicated at 626, are set to high voltage levels at 628. The high voltage level internal node signals SN 626 turn on the internal node transistor 520 in each of the shift register cells 403a-403m. In this example, the series of six timing pulses has been provided prior to timing pulse 602 and shift register 402 has not been initiated, such that all shift register output signals SO, indicated at 630, are discharged to low voltage levels, indicated at 632, and all address signals ~A1, ~A2, . . . ~A7 at 625 remain at high voltage levels, indicated at 633.

The timing pulse 606 of timing signal T2 at 604 is provided to shift register 402 in first evaluation signal EVAL1. Timing pulse 606 turns on the first evaluation transistor 506 in each of the shift register cells 403a-403m. While control signal CSYNC 624 remains at a low voltage level at 634 and all shift register output signals SO 630 remain at low voltage levels at 636, forward input transistor 508 and reverse input transistor 510 in each of the shift register cells 403a-403m are off. The non-conducting forward input transistors 508 and non-conducting reverse input transistors 510 prevent the internal node 522 in each of the shift register cells 403a-403m from discharging to a low voltage level. All shift register internal node signals SN 626 remain at high voltage levels at 638.

The timing pulse 610 of timing signal T3 at 608 is provided to shift register 402 in second pre-charge signal PRE2, to direction circuit 404 in fourth pre-charge signal PRE4 and to address line pre-charge transistors 438 and evaluation prevention transistor 442a in logic array 406. During timing pulse 610 in second pre-charge signal PRE2, all shift register output signals SO 630 charge to high voltage levels at 640. Also, during timing pulse 610 in fourth pre-charge signal PRE4, reverse direction signal DIRR 642 charges to a high voltage level at 644. In addition, timing pulse 610 charges all address signals 625 to high voltage levels at 646 and turns on evaluation prevention transistor 442a to pull logic evaluation signal LEVAL 648 to a low voltage level at 650.

Timing pulse 614 of timing signal T4 at 612 is provided to shift register 402 in second evaluation signal EVAL2, to direction circuit 404 in fourth evaluation signal EVAL4 and to evaluation prevention transistor 442b in logic array 406. The timing pulse 614 in second evaluation signal EVAL2 turns on second evaluation transistor 518 in each of the shift register cells 403a-403m. With the internal node signals SN 626 at high voltage levels having turned on internal node transistor 520 in each of the shift register cells 403a-403m, all shift register output signals SO 630 discharge to low voltage levels at 652. Also, timing pulse 614 in fourth evaluation signal EVAL4 turns on fourth evaluation transistor 562. A control pulse at 654 of control signal CSYNC 624 turns on control transistor 564. With fourth evaluation transistor 562 and control transistor 564 turned on, direction signal DIRR 642 is discharged to a low voltage level at 656. In addition, timing pulse 614 turns on evaluation prevention transistor 442b to hold logic evaluation signal LEVAL 648 at a low voltage level at 658. The low voltage level logic evaluation signal LEVAL 648 turns off address evaluation transistors 440.

Timing pulse 618 of timing signal T5 at 616 is provided to direction circuit 404 in third pre-charge signal PRE3 and to logic evaluation pre-charge transistor 444 in logic array 406. During timing pulse 618 in third pre-charge signal PRE3, forward direction signal DIRF 658 charges to a high voltage level at 660. The high voltage level forward direction signal DIRF 658 turns on forward direction transistor 512 in each of the shift register cells 403a-403m to set up shift register 402 for shifting in the forward direction. Also, during timing pulse 618, logic evaluation signal LEVAL 648 charges to a high voltage level at 662, which turns on all logic evaluation transistors 440. With all shift register output signals SO 630 at low voltage levels, all address transistor pairs 446, 448, . . . 470 are turned off and all address signals ~A1, ~A2, . . . ~A7 at 625 remain at high voltage levels.

Timing pulse 622 from timing signal T6 at 620 is provided to direction circuit 404 as third evaluation signal EVAL3. The timing pulse 622 turns on third evaluation transistor 556. Since control signal CSYNC 624 remains at a low voltage level at 664, control transistor 558 turns off and forward direction signal DIRF 658 remains at a high voltage level. The high voltage level forward direction signal DIRF 658 and low voltage level reverse direction signal DIRR 642 set up each of the shift register cells 403a-403m for shifting in the forward direction.

In the next series of six timing pulses, timing pulse 666 charges all internal node signals SN 626 to high voltage levels. Timing pulse 668 turns on the first evaluation transistor 506 in each of the shift register cells 403a-403m. Control signal CSYNC 624 provides a control pulse at 670 to forward input transistor 508 in shift register cell 403a. With forward direction transistor 512 already turned on, internal node signal SN1 in shift register cell 403a discharges to a low voltage level, indicated at 672. The shift register output signals SO 630 are at low voltage levels at 674, which turns off the forward input transistor in shift register cells 403b-403m. With the forward input transistors off, each of the other internal node signals SN2-SN13 in shift register cells 403b-403m remain at high voltage levels, indicated at 676.

During timing pulse 678, all shift register output signals SO 630 are charged to high voltage levels at 680 and reverse direction signal DIRR 642 is charged to a high voltage level at 682. In addition, during timing pulse 678 all address signals ~A1, ~A2, . . . ~A7 625 are charged to high voltage levels at 684 and logic evaluation signal LEVAL 648 is discharged to a low voltage level at 686. The low voltage level logic evaluation signal LEVAL 648 turns off address evaluation transistors 440, which prevents address transistor pairs 446, 448, 470 from pulling address signals ~A1, ~A2, . . . ~A7 625 to low voltage levels.

During timing pulse 688, shift register output signals SO2-SO13 discharge to low voltage levels at 690. Shift register output signal SO1 remains at a high voltage level, indicated at 692, due to internal node signal SN1 at 672 turning off internal node transistor 520 of shift register cell 403a. Also, timing pulse 688 turns on second evaluation transistor 562 and control pulse 694 turns on control transistor 564 to discharge reverse direction signal DIRR 642 to a low voltage level at 696. In addition, timing pulse 688 turns on evaluation prevention transistor 442b to pull logic evaluation signal LEVAL 648 to a low, voltage level at 698 and keep evaluation transistors 440 turned off.

During timing pulse 700 forward direction signal DIRF 658 is maintained at a high voltage level and logic evaluation signal LEVAL 648 to is charged to a high voltage level at 702. The high voltage level logic evaluation signal LEVAL 648 at 702 turns on evaluation transistors 440. The high level shift register output signal SO1 at 692 turns on address transistor pairs 446a and 446b and address signals ~A1 and ~A2 at 625 are actively pulled to low voltage levels at 704. The other shift register output signals SO2-SO13 are pulled to low voltage levels at 690, such that address transistors 448, 450, . . . 470 are turned off and address signals ~A3-~A7 remain at high voltage levels, indicated at 706. The address signals ~A1, ~A2, . . . ~A7 at 625 become valid during timing pulse 700 in timing signal T5 at 616. Timing pulse 708 turns on third evaluation transistor 556. However, control signal CSYNC 624 is at a low voltage level at 710 and forward direction signal DIRF 658 remains at a high voltage level at 712.

In the next series of six timing pulses, timing pulse 714 charges all internal node signals SN 626 to high voltage levels at 716. Timing pulse 718 turns on first evaluation transistor 506 in each of the shift register cells 403a-403m to allow discharge of node 522, if the forward input signal SIF at each of the shift register cells 403a-403m is in a high voltage level. The forward input signal SIF at shift register cell 403a is the control signal CSYNC 624, which is at a low voltage level at 720. The forward input signal SIF at each of the other shift register cells 403b-403m is the shift register output signal SO 630 of the preceding shift register cell 403. The shift register output signal SO1 is in a high voltage level at 692 and is the forward input signal SIF of second shift register cell 403b. The shift register output signals SO2-SO13 are all at low voltage levels at 690.

Shift register cells 403a and 403c-403m receive low voltage level forward input signals SIF that turn off forward input transistor 508 in each of the shift register cells 403a and 403c-403m, such that internal node signals SN1 and SN3-SN13 remain high at 722. Shift register cell 403b receives the high voltage level shift register output signal SO1 as a forward input signal SIF that turns on the forward input transistor to discharge internal node signal SN2 at 724.

During timing pulse 726 all shift register output signals SO 630 are charged to high voltage levels at 728 and reverse direction signal DIRR 642 to a high voltage level at 730. Also, timing pulse 726 charges all address signals ~A1, ~A2 . . . ~A7 625 toward a high voltage level at 732 and turns on evaluation prevention transistor 442a to pull LEVAL 648 to a low voltage level at 734.

The address signals ~A1, ~A2, . . . ~A7 625 were valid from the time address signals ~A1 and ~A2 were pulled low at 704, until all address signals ~A1, ~A2, . . . ~A7 625 are pulled high at 732. The address signals ~A1, ~A2, . . . ~A7 625 are valid during the timing pulse 708 from timing signal T6 at 620 of the preceding series of six timing pulses and the timing pulses 714 and 718 from timing signals T1 at 600 and T2 at 604 of the present series of six timing pulses.

Timing pulse 736 turns on second evaluation transistor 518 in each of the shift register cells 403a-403m to evaluate internal node signals SN 626. Internal node signals SN1 and SN3-SN13 are at high voltage levels at 722 and discharge shift register output signals SO1 and SO3-SO13 to low voltage levels at 738. Internal node signal SN2 is at a low voltage level at 724 that turns off the internal node transistor of shift register cell 403b and maintains shift register output signal SO2 at a high voltage level at 740.

When fourth evaluation transistor 562 is turned on, by timing pulse 736, and control pulse 742 in CSYNC 624 turns on control transistor 564, reverse direction signal DIRR 642 discharges to a low voltage level at 744. The direction signals DIRR 642 and DIRF 658 are set during each series of six timing pulses. In addition, timing pulse 736 turns on evaluation prevention transistor 442b to maintain LEVAL 648 at a low voltage level at 746.

During timing pulse 748 forward direction signal DIRF 658 is maintained at a high voltage level at 750 and LEVAL 648 charges to a high voltage level at 752. The high voltage level logic evaluation signal LEVAL 678 at 752 turns on evaluation transistors 440. The high voltage level shift register output signal SO2 at 740 turns on address transistors 448a and 448b to pull address signals ~A1 and ~A3 to low voltage levels at 754. The other address signals ~A2 and ~A4-~A7 are maintained at high voltage levels at 756.

Timing pulse 758 turns on third evaluation transistor 556. Control signal CSYNC 624 remains at a low voltage level at 760 to turn off control transistor 558 and maintain forward direction signal DIRF 642 at a high voltage level.

The next series of six timing pulses shifts the high voltage level shift register output signal SO2 to the next shift register cell 403c that provides a high voltage level shift register output signal SO3. Shifting continues with each series of six timing pulses until each shift register output signal SO1-SO13 has been high once. After shift register output signal SO13 has been high, the series of high voltage level shift register output signals SO 630 stops. The shift register 402 can be initiated again by providing a control pulse in control signal CSYNC, such as control pulse 670, coincident with a timing pulse from timing signal T2 at 604.

In forward direction operation, a control pulse in control signal CSYNC 624 is provided coincident with a timing pulse from timing signal T4 at 612 to set the direction of shifting to the forward direction. Also, a control pulse from control signal CSYNC 624 is provided coincident with a timing pulse from timing signal T2 at 604 to start or initiate the shift register 402 shifting a high voltage signal through the shift register output signals SO1-SO13.

Figure 12:
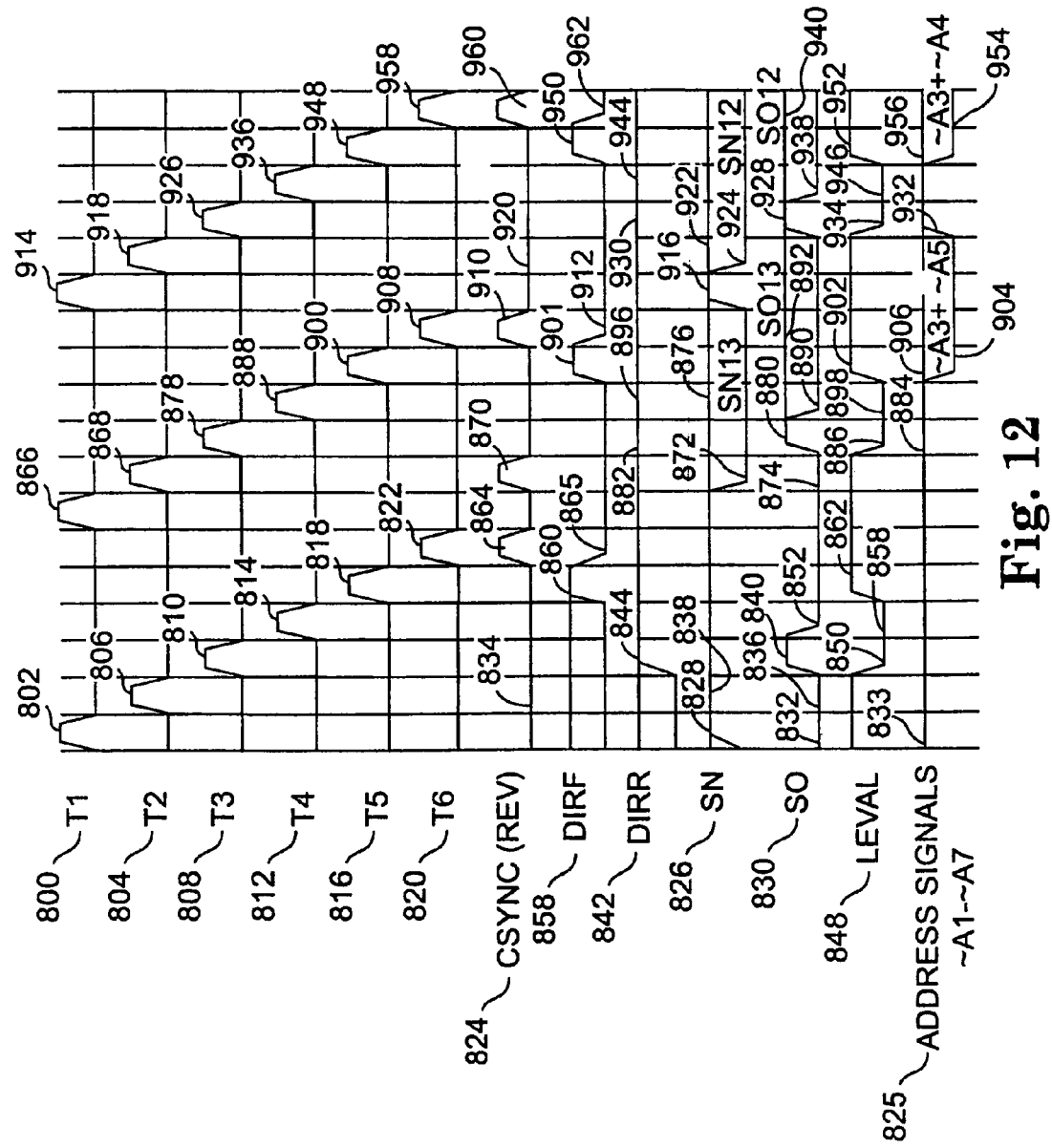
FIG. 12 is a timing diagram illustrating operation of an address generator in the reverse direction.

FIG. 12 is a timing diagram illustrating operation of address generator 400 in the reverse direction. The timing signals T1-T6 provide the repeating series of six pulses. Each of the timing signals T1-T6 provides one pulse in a series of six pulses. In one series of six pulses, timing signal T1 at 800 includes timing pulse 802, timing signal T2 at 804 includes timing pulse 806, timing signal T3 at 808 includes timing pulse 810, timing signal T4 at 812 includes timing pulse 814, timing signal T5 at 816 includes timing pulse 818 and timing signal T6 at 820 includes timing pulse 822. The control signal CSYNC at 824 includes control pulses that set the direction of shifting in shift register 402 and initiate shift register 402 for generating address signals ~A1, ~A2, ... ~A7, indicated at 825.

The timing pulse 802 is provided to shift register 402 in first pre-charge signal PRE1. During timing pulse 802, internal node 522 in each of the shift register cells 403a-403m charges to provide corresponding high voltage level internal node signals SN1-SN13. Shift register internal node signals SN 826 are set to high voltage levels at 828. The high voltage level internal node signals SN 826 turn on the internal node transistors 520 in shift register cells 403. In this example, a series of six timing pulses has been provided prior to timing pulse 802 and without initiating shift register 402, such that all shift register output signals SO 830 are discharged to low voltage levels, indicated at 832 and all address signals ~A1, ~A2, ... ~A7 at 825 remain at high voltage levels, indicated at 833.

The timing pulse 806 is provided to shift register 402 in first evaluation signal EVAL1. Timing pulse 806 turns on the first evaluation transistor 506 in each of the shift register cells 403a-403m. The control signal CSYNC 824 remains at a low voltage level at 834 and all shift register output signals SO 830 remain at low voltage levels at 836 to turn off the forward input transistor 508 and reverse input transistor 510 in each of the shift register cells 403a-403m. The non-conducting forward and reverse input transistors 508 and 510 prevent the internal node 522 in each of the shift register cells 403a-403m from discharging to a low voltage level. All shift register internal node signals SN 826 remain at high voltage levels at 838.

The timing pulse 810 is provided to shift register 402 in second pre-charge signal PRE2, to direction circuit 404 in fourth pre-charge signal PRE4 and to address line pre-charge transistors 438 and evaluation prevention transistor 442a in logic array 406. During timing pulse 810, all shift register output signals SO 830 are charged to high voltage levels at 840. Also, during timing pulse 810, reverse direction signal DIRR 842 charges to a high voltage level at 844. In addition, timing pulse 810 maintains all address signals 825 at high voltage levels and turns on evaluation prevention transistor 442a to pull logic evaluation signal LEVAL 848 to a low voltage level at 850.

Timing pulse 814 is provided to shift register 402 in second evaluation signal EVAL2, to direction circuit 404 in fourth evaluation signal EVAL4 and to evaluation prevention transistor 442b in logic array 406. Timing pulse 814 turns on the second evaluation transistor 518 in each of the shift register cells 403a-403m. With internal node signals SN 826 at high voltage levels that turn on internal node transistor 520 in each of the shift register cells 403a-403m, all shift register output signals SO 830 discharge to low voltage levels at 852. Also, timing pulse 814 turns on fourth evaluation transistor 562 and control signal CSYNC 824 provides a low voltage to turn off control transistor 564. With control transistor 564 turned off, reverse direction signal DIRR 842 remains charged to a high voltage level. In addition, timing pulse 814 turns on evaluation prevention transistor 442b to hold logic evaluation signal LEVAL 848 at a low voltage level at 858. The low voltage level logic evaluation signal LEVAL 848 turns off address evaluation transistors 440.

Timing pulse 818 is provided to direction circuit 404 in third pre-charge signal PRE3 and to logic evaluation pre-charge transistor 444 in logic array 406. During timing pulse 818, forward direction signal DIRF 858 charges to a high voltage level at 860. Also, during timing pulse 818 logic evaluation signal LEVAL 848 charges to a high voltage level at 862 to turn on all logic evaluation transistors 440. With all shift register output signals SO 830 at low voltage levels, all address transistor pairs 446, 448, ... 470 are turned off and all address signals ~A1, ~A2, ... ~A7 at 825 remain at high voltage levels.

Timing pulse 822 is provided to direction circuit 404 as third evaluation signal EVAL3. The timing pulse 822 turns on third evaluation transistor 556. The control signal CSYNC 824 provides a control pulse 864 to turn on control transistor 558 and forward direction signal DIRF 858 is discharged to a low voltage level at 865. The low voltage level forward direction signal DIRF 858 and high voltage level reverse direction signal DIRR 842 set each of the shift register cells 403a-403m for shifting in the reverse direction.

In the next series of six timing pulses, during timing pulse 866, all internal node signals SN 826 are charged to high voltage levels. Timing pulse 868 turns on the first evaluation transistor 506 in each of the shift register cells 403a-403m. A control pulse 870, which may be in control signal CSYNC, is provided to turn on the reverse input transistor in shift register cell 403m and with the reverse direction transistor turned on, internal node signal SN13 discharges to a low voltage level, indicated at 872. The shift register output signals SO 830 are at low voltage levels at 874, which turns off the reverse input transistor in shift register cells 403a-403l. With the reverse input transistors off, each of the other internal node signals SN1-SN12 remain at high voltage levels, indicated at 876.

During timing pulse 878, all shift register output signals SO 830 are charged to high voltage levels at 880 and reverse direction signal DIRR 842 is maintained at a high voltage level at 882. In addition, timing pulse 878 maintains all address signals ~A1, ~A2, ... ~A7 825 at high voltage levels at 884 and pulls logic evaluation signal LEVAL 848 to a low voltage level at 886. The low voltage level logic evaluation signal LEVAL 848 turns off evaluation transistors 440, which prevents address transistor pairs 446, 448, ... 470 from pulling address signals ~A1, ~A2, ... ~A7 825 to low voltage levels.

During timing pulse 888, shift register output signals SO1-SO12 are discharged to low voltage levels at 890. Shift register output signal SO13 remains at a high voltage level, indicated at 892, based on the low voltage level internal node signal SN13 at 872 that turns off internal node transistor 520 of shift register cell 403m. Also, timing pulse 888 turns on second evaluation transistor and control signal CSYNC 824 turns off control transistor 564 to maintain reverse direction signal DIRR 842 at a high voltage level at 896. In addition, timing pulse 888 turns on evaluation prevention transistor 442b to hold logic evaluation signal LEVAL 848 at a low voltage level at 898 and keep evaluation transistors 440 turned off. Shift register output signals SO 830 settle during timing pulse 888, such that one shift register output signal SO13 is at a high voltage level and all other shift register output signals SO1-SO12 are at low voltage levels.

During timing pulse 900, forward direction signal DIRF 858 charges to a high voltage level at 901 and logic evaluation signal LEVAL 848 charges to a high voltage level at 902. The high voltage level logic evaluation signal LEVAL 848 at 902 turns on evaluation transistors 440. The high voltage level shift register output signal SO13 at 892 turns on address transistors 470a and 470b and address signals ~A3 and ~A5 are actively pulled to low voltage levels, indicated at 904. The other shift register output signals SO1-SO12 are pulled to low voltage levels at 890, such that address transistor pairs 446, 448, ... 468 are turned off and address signals ~A1, ~A2, ~A4, ~A6 and ~A7 remain at high voltage levels, indicated at 906. The address signals ~A1, ~A2, ... ~A7 825 become valid during timing pulse 900. Timing pulse 908 turns on third evaluation transistor 556 and a control pulse 910 in control signal CSYNC 824 turns on control transistor 558 to discharge the forward direction signal DIRF 858 to a low voltage at 912.

In the next series of six timing pulses, during timing pulse 914 all internal node signals SN 826 are charged to high voltage levels at 916. Timing pulse 918 turns on first evaluation transistor 506 in each of the shift register cells 403a-403m to discharge node 522 if the reverse input signal SIR at each of the shift register cells 403a-403m is at a high voltage level. The reverse input signal SIR at shift register cell 403m is the control signal CSYNC 824, which is at a low voltage level at 920. The reverse input signal SIR at each of the other shift register cells 403a-403l is the shift register output signal SO 830 of the following shift register cell 403. The shift register output signal SO13 is at a high voltage level at 892 and is the reverse input signal SIR of shift register cell 403l. The shift register output signals SO1-SO12 are all at low voltage levels at 890. Shift register cells 403a-403k and 403m have low voltage level reverse input signals SIR that turn off reverse input transistor 510, such that internal node signals SN1-SN11 and SN13 remain at high voltage levels at 922. Shift register cell 403l receives the high voltage level shift register output signal SO13 as the reverse input signal SIR that turns on the reverse input transistor to discharge internal node signal SN12 at 924.

During timing pulse 926, all shift register output signals SO 830 are charged to high voltage levels at 928 and reverse direction signal DIRR 842 is maintained at a high voltage level at 930. Also, during timing pulse 926 all address signals ~A1, ~A2, ... ~A7 825 are charged to a high voltage level at 932 and evaluation prevention transistor 442a is turned on to pull LEVAL 848 to a low voltage level at 934. The address signals ~A1, ~A2, ... ~A7 825 were valid from the time address signals ~A3 and ~A5 were pulled low at 904 until all address signals ~A1, ~A2, ... ~A7 825 are pulled high at 932. The address signals ~A1, ~A2, ... ~A7 825 are valid during the timing pulses 908, 914 and 918.

Timing pulse 936 turns on second evaluation transistor 518 in each of the shift register cells 403a-403m to evaluate the internal node signals SN 826. Internal node signals SN1-SN11 and SN13 are at high voltage levels at 922 to discharge shift register output signals SO1-SO11 and SO13 to low voltage levels at 938. Internal node signal SN12 is at a low voltage level at 924 that turns off the internal node transistor of shift register cell 403l and maintains shift register output signal SO12 at a high voltage level at 940.

Also, timing pulse 936 turns on fourth evaluation transistor 562 and control signal CSYNC 824 is at a low voltage level to turn off control transistor 564 to maintain reverse direction signal DIRR 842 at a high voltage level at 944. In addition, timing pulse 936 turns on evaluation prevention transistor 442b to maintain LEVAL 848 at a low voltage level at 946.

During timing pulse 948, forward direction signal DIRF 858 is charged to a high voltage level at 950 and LEVAL 848 is charged to a high voltage level at 952. The high voltage level logic evaluation signal LEVAL 848 at 952 turns on evaluation transistors 440. The high voltage level shift register output signal SO12 at 940 turns on address transistors 468a and 468b to pull address signals ~A3 and ~A4 to low voltage levels at 954. The other address signals ~A1, ~A2 and ~A5-~A7 are maintained at high voltage levels at 956.

Timing pulse 958 turns on third evaluation transistor 556. A control pulse 960 in control signal CSYNC 824 turns on control transistor 558 and forward direction signal DIRF 858 discharges to a low voltage level at 962.

The next series of six timing pulses shifts the high voltage level shift register output signal SO12 to the next shift register cell 403k that provides a high voltage level shift register output signal SO11. Shifting continues with each series of six timing pulses until each shift register output signal SO1-SO13 has been high once. After shift register output signal SO1 is high, the series of high voltage level shift register output signals SO 830 stops. The shift register 402 can be initiated again by providing a control pulse, such as control pulse 870, coincident with a timing pulse from timing signal T2 804.

In reverse direction operation, a control pulse from CSYNC 824 is provided coincident with a timing pulse from timing signal T6 at 820 to set the direction of shifting to the reverse direction. Also, a control pulse from CSYNC 824 is provided coincident with a timing pulse from timing signal T2 804 to start or initiate the shift register 402 shifting a high voltage level signal through the shift register output signals SO1-SO13.

Figure 13:
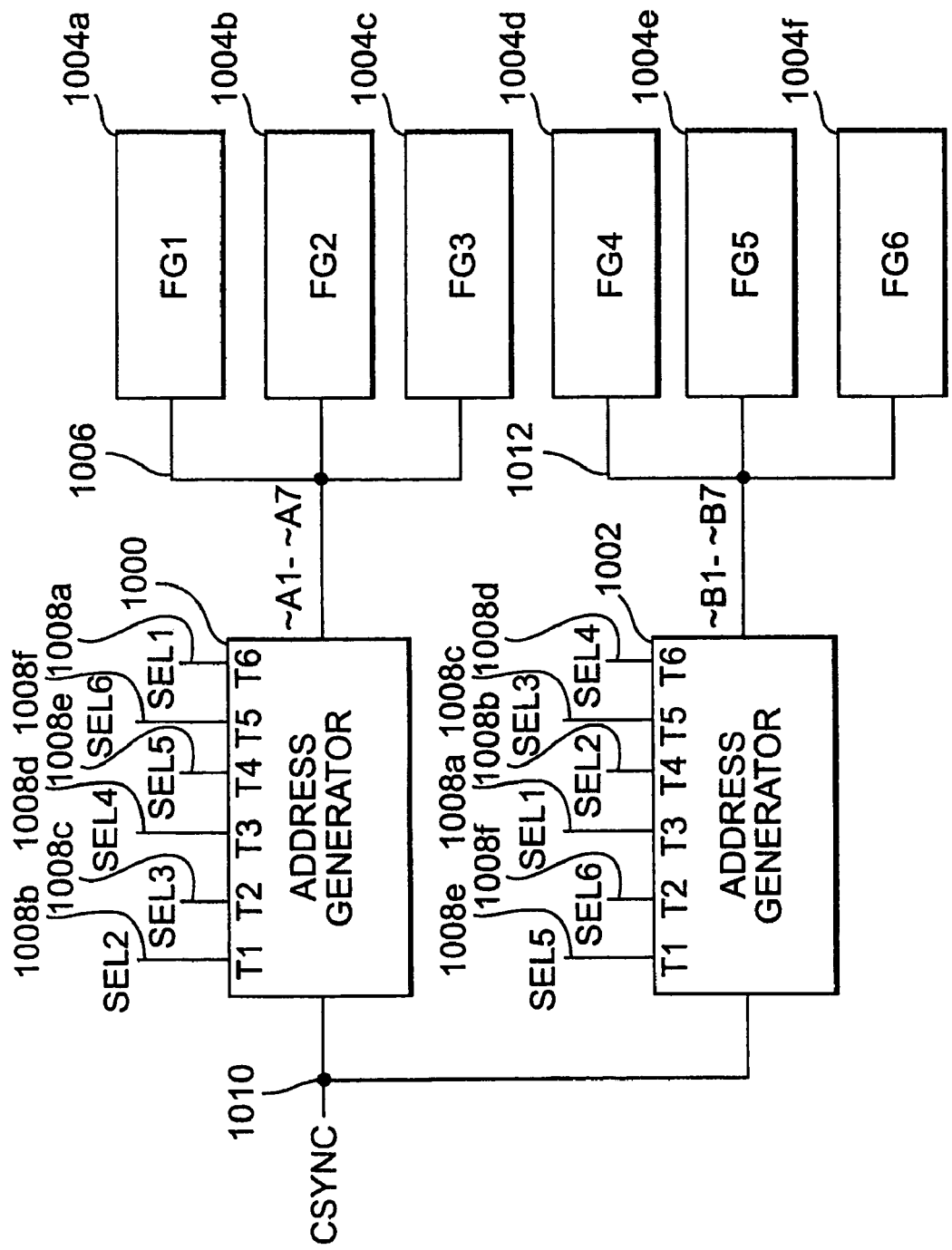
FIG. 13 is a block diagram illustrating one embodiment of two address generators and six fire groups in a printhead die.

FIG. 13 is a block diagram illustrating one embodiment of two address generators 1000 and 1002 and six fire groups 1004a-1004f. Each of the address generators 1000 and 1002 is similar to address generator 400 of FIG. 9 and fire groups 1004a-1004f are similar to fire groups 202a-202f illustrated in FIG. 7. The address generator 1000 is electrically coupled to fire groups 1004a-1004c through first address lines 1006. The address lines 1006 provide address signals ~A1, ~A2, ... ~A7 from address generator 1000 to each of the fire groups 1004a-1004c. Also, address generator 1000 is electrically coupled to control line 1010. Control line 1010 receives conducts control signal CSYNC to address generator 1000. In one embodiment, the CSYNC signal is provided by an external controller to a printhead die on which two address generators 1000 and 1002 and six fire groups 1004a-1004f are fabricated. In addition, address generator 1000 is electrically coupled to select lines 1008a-1008f. The select lines 1008a-1008f are similar to select lines 212a-212f illustrated in FIG. 7. The select lines 1008a-1008f conduct select signals SEL1, SEL2, SEL6 to address generator 1000, as well as to the corresponding fire groups 1004a-1004f (not shown).

The select line 1008a conducts select signal SEL1 to address generator 1000, in one embodiment is timing signal T3 timing signal T6. The select line 1008b conducts select signal SEL2 to address generator 1000, in one embodiment is timing signal T4 timing signal T1. The select line 1008c conducts select signal SEL3 to address generator 1000 in one embodiment is timing signal T5 timing signal T2. The select line 1008d conducts select signal SEL4 to address generator 1000, in one embodiment is timing signal T6 timing signal T3. The select line 1008e conducts select signal SEL5 to address generator 1000, in one embodiment is timing signal T1 timing signal T4, and the select line 1008f conducts select signal SEL6 to address generator 1000, in one embodiment is timing signal T2 timing signal T5.

The address generator 1002 is electrically coupled to fire groups 1004d-1004f through second address lines 1012. The address lines 1012 provide address signals ~B1, ~B2, ... ~B7 from address generator 1002 to each of the fire groups 1004d-1004f. Also, address generator 1002 is electrically coupled to control line 1010 that conducts control signal CSYNC to address generator 1002. In addition, address generator 1002 is electrically coupled to select lines 1008a-1008f. The select lines 1008a-1008f conduct select signals SEL1, SEL2, ... SEL6 to address generator 1002, as well as to the corresponding fire groups 1004a-1004f (not shown).

The select line 1008a conducts select signal SEL1 to address generator 1002, which in one embodiment is timing signal T3. The select line 1008b conducts select signal SEL2 to address generator 1002, which in one embodiment is timing signal T4. The select line 1008c conducts select signal SEL3 to address generator 1002, which in one embodiment is timing signal T5. The select line 1008d conducts select signal SEL4 to address generator 1002, which in one embodiment is timing signal T6. The select line 1008e conducts select signal SEL5 to address generator 1002, which in one embodiment is timing signal T1, and the select line 1008f conducts select signal SEL6 to address generator 1002, which in one embodiment is timing signal T2.

The select signals SEL1, SEL2, ... SEL 6 include a series of six pulses that repeats in a repeating series of six pulses. Each of the select signals SEL1, SEL2, ... SEL6 includes one pulse in the series of six pulses. In one embodiment, a pulse in select signal SEL1 is followed by a pulse in select signal SEL2, that is followed by a pulse in select signal SEL3, that is followed by a pulse in select signal SEL4, that is followed by a pulse in select signal SEL5, that is followed by a pulse in select signal SEL6. After the pulse in select signal SEL6, the series repeats beginning with a pulse in select signal SEL1. The control signal CSYNC includes pulses coincident with pulses in select signals SEL1, SEL2, ... SEL6 to initiate address generators 1000 and 1002 and to set up the direction of shifting or address generation in address generators 1000 and 1002, for example as discussed with respect to FIGS. 11 and 12. To initiate address generation from address generator 1000, control signal CSYNC includes a control pulse coincident with a timing pulse in timing signal T2 that corresponds to the timing pulse in select signal SEL3.

The address generator 1000 generates address signals ~A1, ~A2, ... ~A7 in response to select signals SEL1, SEL2, ... SEL6 and control signal CSYNC. The address signals ~A1, ~A2, ... ~A7 are provided through first address lines 1006 to fire groups 1004a-1004c.

In address generator 1000, address signals ~A1, ~A2, ... ~A7 are valid during timing pulses in timing signals T6, T1 and T2 that correspond to timing pulses in select signals SEL1, SEL2 and SEL3. The control signal CSYNC includes a control pulse coincident with a timing pulse in timing signal T4 that corresponds to the timing pulse in select signal SEL5 to set up address generator 1000 for shifting in the forward direction. The control signal CSYNC includes a control pulse coincident with a timing pulse in timing signal T6 that corresponds to the timing pulse in select signal SEL1 to set up address generator 1000 for shifting in the reverse direction.

The fire groups 1004a-1004c receive valid address signals ~A1, ~A2, ... , ~A7 during the pulses in select signals SEL1, SEL2 and SEL3. When fire group one (FG1) at 1004a receives the address signals ~A1, ~A2, ... ~A7 and the pulse in select signal SEL1, firing cells 120 in selected row subgroups SG1 are enabled for activation by fire signal FIRE1. When fire group two (FG2) at 1004b receives the address signals ~A1, ~A2, ... ~A7 and the pulse in select signal SEL2, firing cells 120 in selected row subgroups SG2 are enabled for activation by fire signal FIRE2. When fire group three (FG3) at 1004c receives the address signals ~A1, ~A2, ... ~A7 and the pulse in select signal SEL3, firing cells 120 in selected row subgroups SG3 are enabled for activation by fire signal FIRE3.

The address generator 1002 generates address signals ~B1, ~B2, ... ~B7 in response to the select signals SEL1, SEL2, ... SEL6 and control signal CSYNC. The address signals ~B1, ~B2, ... ~B7 are provided through second address lines 1012 to fire groups 1004d-1004f. In address generator 1002, the address signals ~B1, ~B2, ... ~B7 are valid during timing pulses in timing signals T6, T1 and T2 that correspond to timing pulses in select signals SEL4, SEL5 and SEL6. The control signal CSYNC includes a control pulse coincident with a timing pulse in timing signal T4 that corresponds to the timing pulse in select signal SEL2 to set up address generator 1002 for shifting in the forward direction. The control signal CSYNC includes a control pulse coincident with a timing pulse in timing signal T6 that corresponds to the timing pulse in select signal SEL4 to set up address generator 1002 for shifting in the reverse direction. To initiate address generation from address generator 1002, control signal CSYNC includes a control pulse coincident with a timing pulse in timing signal T2 that corresponds to the timing pulse in select signal SEL6.

The fire groups 1004d-1004f receive valid address signals ~B1, ~B2, ... , ~B7 during the pulses in select signals SEL4, SEL5 and SEL6. When fire group four (FG4) at 1004d receives the address signals ~B1, ~B2, ... ~B7 and the pulse in select signal SEL4, firing cells 120 in selected row subgroups SG4 are enabled for activation by fire signal FIRE4. When fire group five (FG5) at 1004e receives the address signals ~B1, ~B2, ... ~B7 and the pulse in select signal SEL5, firing cells 120 in selected row subgroups SG5 are enabled for activation by fire signal FIRE5. When fire group six (FG6) at 1004f receives the address signals ~B1, ~B2, ... ~B7 and the pulse in select signal SEL6, firing cells 120 in selected row subgroups SG6 are enabled for activation by fire signal FIRE6.

In one example operation, during one series of six pulses, control signal CSYNC includes control pulses coincident with the timing pulses in select signals SEL2 and SEL5 to set up address generators 1000 and 1002 for shifting in the forward direction. The control pulse coincident with the timing pulse in select signal SEL2 sets up address generator 1002 for shifting in the forward direction. The control pulse coincident with the timing pulse in select signal SEL5 sets up address generator 1000 for shifting in the forward direction.

In the next series of six pulses, control signal CSYNC includes control pulses coincident with timing pulses in select signals SEL2, SEL3, SEL5 and SEL6. The control pulses coincident with timing pulses in select signals SEL2 and SEL5 set the direction of shifting to the forward direction in address generators 1000 and 1002. The control pulses coincident with timing pulses in select signals SEL3 and SEL6 initiate the address generators 1000 and 1002 for generating address signals ~A1, ~A2, ... ~A7 and ~B1, ~B2, ... ~B7. The control pulse coincident with the timing pulse in select signal SEL3 initiates the address generator 1000 and the control pulse coincident with the timing pulse in select signal SEL6 initiates the address generator 1002.

During the third series of timing pulses, address generator 1000 generates address signals ~A1, ~A2, ... ~A7 that are valid during timing pulses in select signals SEL1, SEL2 and SEL3. The valid address signals ~A1, ~A2, ..., ~A7 are used for enabling firing cells 120 in row subgroups SG1, SG2 and SG3 in fire groups FG1, FG2 and FG3 at 1004a-1004c for activation. During the third series of timing pulses, address generator 1002 generates address signals ~B1, ~B2, ... ~B7 that are valid during timing pulses in select signals SEL4, SEL5 and SEL6. The valid address signals ~B1, ~B2, ... ~B7 are used for enabling firing cells 120 in row subgroups SG4, SG5 and SG6 in fire groups FG4, FG5 and FG6 at 1004d-1004f for activation.

During the third series of timing pulses in select signals SEL1, SEL2, SEL6, address signals ~A1, ~A2, ... ~A7 include low voltage level signals that correspond to one of thirteen addresses and address signals ~B1, ~B2, ... ~B7 include low voltage level signals that correspond to the same one of thirteen addresses. During each subsequent series of timing pulses from select signals SEL1, SEL2, ... SEL6, address signals ~A1, ~A2, ... ~A7 and address signals ~B1, ~B2, ... ~B7 include low voltage level signals that correspond to the same one of thirteen addresses. Each series of timing pulses is an address time slot, such that one of the thirteen addresses is provided during each series of timing pulses.

In forward direction operation, address one is provided first by address generators 1000 and 1002, followed by address two and so on through address thirteen. After address thirteen, address generators 1000 and 1002 provide all high voltage level address signals ~A1, ~A2, ... ~A7 and ~B1, ~B2, ... ~B7. Also, during each series of timing pulses from select signals SEL1, SEL2, SEL6, control pulses are provided coincident with timing pulses in select signals SEL2 and SEL5 to continue shifting in the forward direction.

In another example operation, during one series of six pulses, control signal CSYNC includes control pulses coincident with timing pulses in select signals SEL1 and SEL4 to set up address generators 1000 and 1002 for shifting in the reverse direction. The control pulse coincident with the timing pulse in select signal SEL1 sets up address generator 1000 for shifting in the reverse direction. The control pulse coincident with the timing pulse in select signal SEL4 sets up address generator 1002 for shifting in the reverse direction.

In the next series of six pulses, control signal CSYNC includes control pulses coincident with the timing pulses in select signals SEL1, SEL3, SEL4 and SEL6. The control pulses coincident with timing pulses in select signals SEL1 and SEL4 set the direction of shifting to the reverse direction in address generators 1000 and 1002. The control pulses coincident with timing pulses in select signals SEL3 and SEL6 initiate the address generators 1000 and 1002 for generating address signals ~A1, ~A2, ... ~A7 and ~B1, ~B2, ... ~B7. The control pulses coincident with the timing pulse in select signal SEL3 initiates address generator 1000 and the control pulse coincident with the timing pulse in select signal SEL6 initiates address generator 1002.

During the third series of timing pulses, address generator 1000 generates address signals ~A1, ~A2, ... ~A7 that are valid during timing pulses in select signals SEL1, SEL2 and SEL3. The valid address signals ~A1, ~A2, ..., ~A7 are used for enabling firing cells 120 in row subgroups SG1, SG2 and SG3 in fire groups FG1, FG2 and FG3 at 1004a-1004c for activation. Address generator 1002 generates address signals ~B1, ~B2, ... ~B7 that are valid during timing pulses in select signals SEL4, SEL5 and SEL6 during the third series of timing pulses. The valid address signals ~B1, ~B2, ... ~B7 are used for enabling firing cells 120 in row subgroups SG4, SG5 and SG6 in fire groups FG4, FG5 and FG6 at 1004d-1004f for activation.

During the third series of timing pulses in select signals SEL1, SEL2, SEL6 in reverse direction operation, address signals ~A1, ~A2, ... ~A7 include low voltage level signals that correspond to one of thirteen addresses and address signals ~B1, ~B2, ... ~B7 include low voltage level signals that correspond to the same one of thirteen addresses. During each subsequent series of timing pulses from select signals SEL1, SEL2, ... SEL6, address signals ~A1, ~A2, ... ~A7 and ~B1, ~B2, ... ~B7 include low voltage level signals that correspond to the same one of thirteen addresses. Each series of timing pulses is an address time slot, such that one of the thirteen addresses is provided during each series of timing pulses.

In reverse direction operation, address thirteen is provided first by address generator 1000 and 1002, followed by address twelve and so on through address one. After address one, address generators 1000 and 1002 provide all high voltage level address signals ~A1, ~A2, ... ~A7 and ~B1, ~B2, ... ~B7. Also, during each series of timing pulses from select signals SEL1, SEL2 ... SEL6 control pulses are provided coincident with timing pulses in select signals SEL1 and SEL4 to continue shifting in the reverse direction.

To terminate or prevent address generation, control signal CSYNC includes control pulses coincident with timing pulses in select signals SEL1, SEL2, SEL4 and SEL5. This clears the shift registers, such as shift register 402, in address generators 1000 and 1002. A constant high voltage level, or a series of high voltage pulses, in control signal CSYNC also terminates or prevents address generation and a constant low voltage level in control signal CSYNC will not initiate address generators 1000 and 1002.

Figure 14:
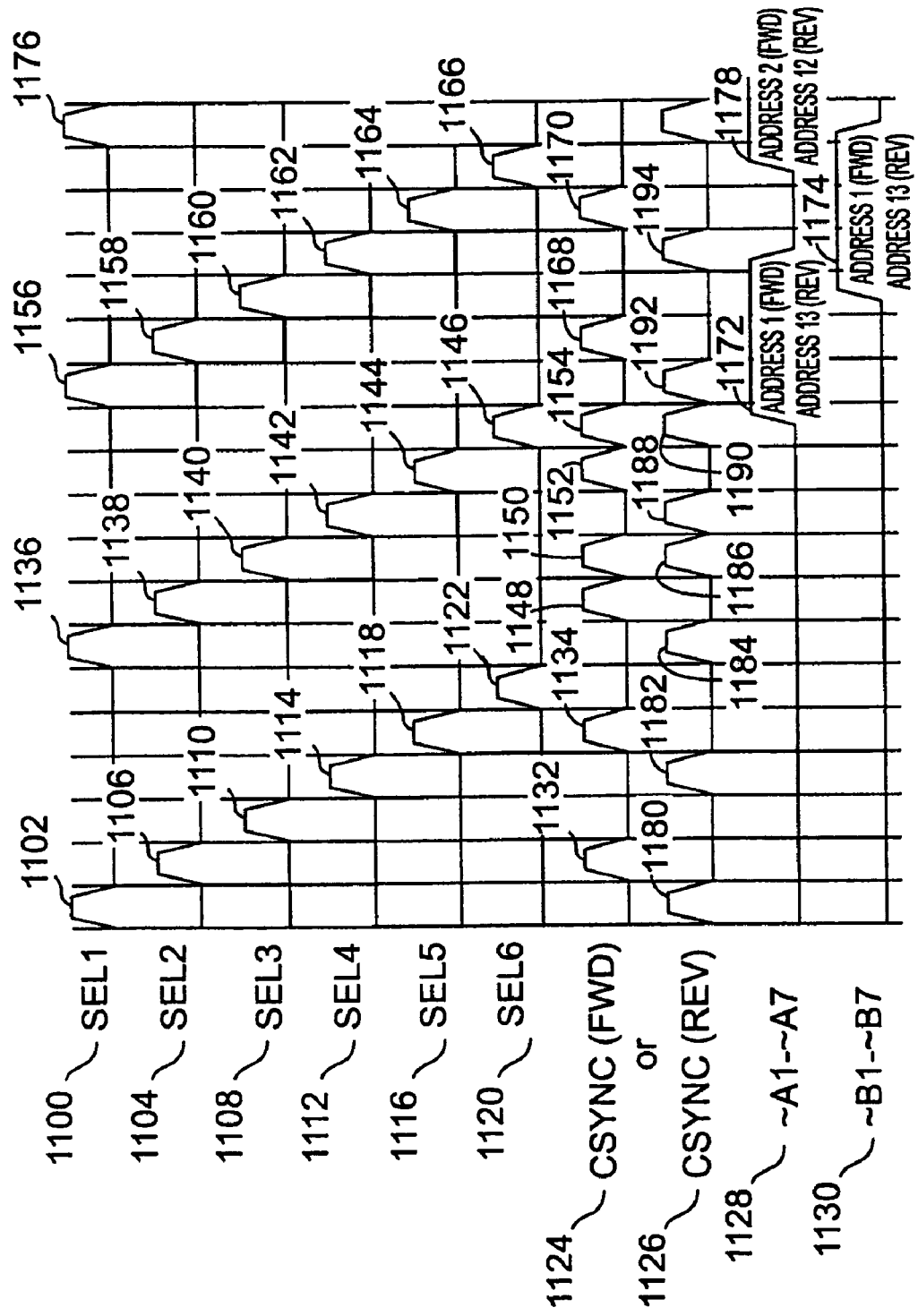
FIG. 14 is a timing diagram illustrating forward and reverse operation of address generators in a printhead die.

FIG. 14 is a timing diagram illustrating forward and reverse operation of address generators 1000 and 1002. The control signal used for shifting in the forward direction is CSYNC (FWD) at 1124 and the control signal used for shifting in the reverse direction is CSYNC(REV) at 1126. The address signals ~A1, ~A2, ... ~A7 at 1128 are provided by address generator 1000 and include both forward and reverse operation address references. The address signals ~B1, ~B2, ... ~B7 at 1130 are provided by address generator 1002 and include both forward and reverse operation address references.

The select signals SEL1, SEL2, ... SEL6 provide a repeating series of six pulses. Each of the select signals SEL1, SEL2, SEL6 includes one pulse in the series of six pulses. In one series of the repeating series of six pulses, select signal SEL1 at 1100 includes timing pulse 1102, select signal SEL2 at 1104 includes timing pulse 1106, select signal SEL3 at 1108 includes timing pulse 1110, select signal SEL4 at 1112 includes timing pulse 1114, select signal SEL5 at 1116 includes timing pulse 1118 and select signal SEL6 at 1120 includes timing pulse 1122.

In forward direction operation, control signal CSYNC (FWD) 1124 includes control pulse 1132 coincident with timing pulse 1106 in select signal SEL2 at 1104. The control pulse 1132 sets up address generator 1002 for shifting in the forward direction. Also, control signal CSYNC(FWD) 1124 includes control pulse 1134 coincident with timing pulse 1118 in select signal SEL5 at 1116. The control pulse 1134 sets up address generator 1000 for shifting in the forward direction.

In the next repeating series of six pulses, the select signal SEL1 at 1100 includes timing pulse 1136, select signal SEL2 at 1104 includes timing pulse 1138, select signal SEL3 at 1108 includes timing pulse 1140, select signal SEL4 at 1112 includes timing pulse 1142, select signal SEL5 at 1116 includes timing pulse 1144 and select signal SEL6 at 1120 includes timing pulse 1146.

Control signal CSYNC(FWD) 1124 includes control pulse 1148 coincident with timing pulse 1138 to continue setting address generator 1002 for shifting in the forward direction and control pulse 1152 coincident with timing pulse 1144 to continue setting address generator 1000 for shifting in the forward direction. Also, control signal CSYNC(FWD) 1124 includes control pulse 1150 coincident with timing pulse 1140 in select signal SEL3 at 1108. The control pulse 1150 initiates address generator 1000 for generating address signals ~A1, ~A2, . . . ~A7 at 1128. In addition, control signal CSYNC(FWD) 1124 includes control pulse 1154 coincident with timing pulse 1146 in select signal SEL6 at 1120. The control pulse 1154 initiates address generator 1002 for generating address signals ~B1, ~B2, . . . ~B7 at 1130.

In the next or third series of six pulses, select signal SEL1 at 1100 includes timing pulse 1156, select signal SEL2 at 1104 includes timing pulse 1158, select signal SEL3 at 1108 includes timing pulse 1160, select signal SEL4 at 1112 includes timing pulse 1162, select signal SEL5 at 1116 includes timing pulse 1164 and select signal SEL6 at 1120 includes timing pulse 1166. The control signal CSYNC (FWD) 1124 includes control pulse 1168 coincident with timing pulse 1158 to continue setting address generator 1002 for shifting in the forward direction and control pulse 1170 coincident with timing pulse 1164 to continue setting address generator 1000 for shifting in the forward direction.

The address generator 1000 provides address signals ~A1, ~A2, . . . ~A7 at 1128. After being initiated in forward direction operation, address generator 1000 and address signals ~A1, ~A2, . . . ~A7 at 1128 provide address one at 1172. Address one at 1172 becomes valid during timing pulse 1146 in select signal SEL6 at 1120 and remains valid until timing pulse 1162 in select signal SEL4 at 1112. Address one at 1172 is valid during timing pulses 1156, 1158 and 1160 in select signals SEL1, SEL2 and SEL3 at 1100, 1104 and 1108.

The address generator 1002 provides address signals ~B1, ~B2, . . . ~B7 at 1130. After being initiated in forward direction operation, address generator 1002 and address signals ~B1, ~B2, . . . ~B7 at 1130 provide address one at 1174. Address one at 1174 becomes valid during timing pulse 1160 in select signal SEL3 at 1108 and remains valid until timing pulse 1176 in select signal SEL1 at 1100. Address one at 1174 is valid during timing pulses 1162, 1164 and 1166 in select signals SEL4, SEL5 and SEL6 at 1112, 1116 and 1120.

The address signals ~A1, ~A2, . . . ~A7 at 1128 and ~B1, ~B2, . . . ~B7 at 1130 provide the same address, address one at 1172 and 1174. Address one is provided during the series of six timing pulses beginning with timing pulse 1156 and ending with timing pulse 1166, which is the address time slot for address one. During the next series of six pulses, beginning with timing pulse 1176, address signals ~A1, ~A2, . . . ~A7 at 1128 provide address two at 1178 and address signals ~B1, ~B2, . . . ~B7 at 1130 provide address two also. In this way, address generators 1000 and 1002 provide addresses from address one through address thirteen in the forward direction. After address thirteen, address generators 1000 and 1002 are reinitiated to cycle through the valid addresses again in the same way.

In reverse direction operation, control signal CSYNC (REV) 1126 includes control pulse 1180 coincident with timing pulse 1102 in select signal SEL1 at 1100. The control pulse 1180 sets up address generator 1000 for shifting in the reverse direction. Also, control signal CSYNC(REV) 1126 includes control pulse 1182 coincident with timing pulse 1114 in select signal SEL4 at 1112. The control pulse 1182 sets up address generator 1002 for shifting in the reverse direction.

Control signal CSYNC(REV) 1126 includes control pulse 1184 coincident with timing pulse 1136 to continue setting address generator 1000 for shifting in the reverse direction and control pulse 1188 coincident with timing pulse 1142 to continue setting address generator 1002 for shifting in the reverse direction. Also, control signal CSYNC(REV) 1126 includes control pulse 1186 coincident with timing pulse 1140 in select signal SEL3 at 1108. The control pulse 1186 initiates address generator 1000 for generating address signals ~A1, ~A2, . . . ~A7 at 1128. In addition, control signal CSYNC(REV) 1126 includes control pulse 1190 coincident with timing pulse 1146 in select signal SEL6 at 1120. The control pulse 1190 initiates address generator 1002 for generating address signals ~B1, ~B2, . . . ~B7 at 1130.

The control signal CSYNC(REV) 1126 includes control pulse 1192 coincident with timing pulse 1156 to continue setting address generator 1000 for shifting in the reverse direction and control pulse 1194 coincident with timing pulse 1162 to continue setting address generator 1002 for shifting in the reverse direction.

The address generator 1000 provides address signals ~A1~A7 at 1128. After being initiated in reverse direction operation, address generator 1000 and address signals ~A1, ~A2, . . . ~A7 at 1128 provide address thirteen at 1172. Address thirteen at 1172 becomes valid during timing pulse 1146 and remains valid until timing pulse 1162. Address thirteen at 1172 is valid during timing pulses 1156, 1158 and 1160 in select signals SEL1, SEL2 and SEL3 at 1100, 1104 and 1108.

The address generator 1002 provides address signals ~B1, ~B2, . . . ~B7 at 1130. After being initiated in reverse direction operation, address generator 1002 and address signals ~B1, ~B2, . . . ~B7 at 1130 provide address thirteen at 1174. Address thirteen at 1174 becomes valid during timing pulse 1160 and remains valid until timing pulse 1176. Address thirteen at 1174 is valid during timing pulses 1162, 1164 and 1166 in select signals SEL4, SEL5 and SEL6 at 1112, 1116 and 1120.

The address signals ~A1, ~A2, . . . ~A7 at 1128 and ~B1, ~B2, . . . ~B7 at 1130 provide the same address, address thirteen at 1172 and 1174. Address thirteen is provided during the series of six timing pulses beginning with timing pulse 1156 and ending with timing pulse 1166, which is the address time slot for address thirteen. During the next series of six pulses, beginning with timing pulse 1176, address signals ~A1, ~A2, . . . ~A7 at 1128 provide address twelve at 1178 and address signals ~B1, ~B2, . . . ~B7 at 1130 provide address twelve also. Address generators 1000 and 1002 provide addresses from address thirteen through address one in the reverse direction. After address one, address generators 1000 and 1002 are reinitiated to provide valid addresses again.

Figure 15:
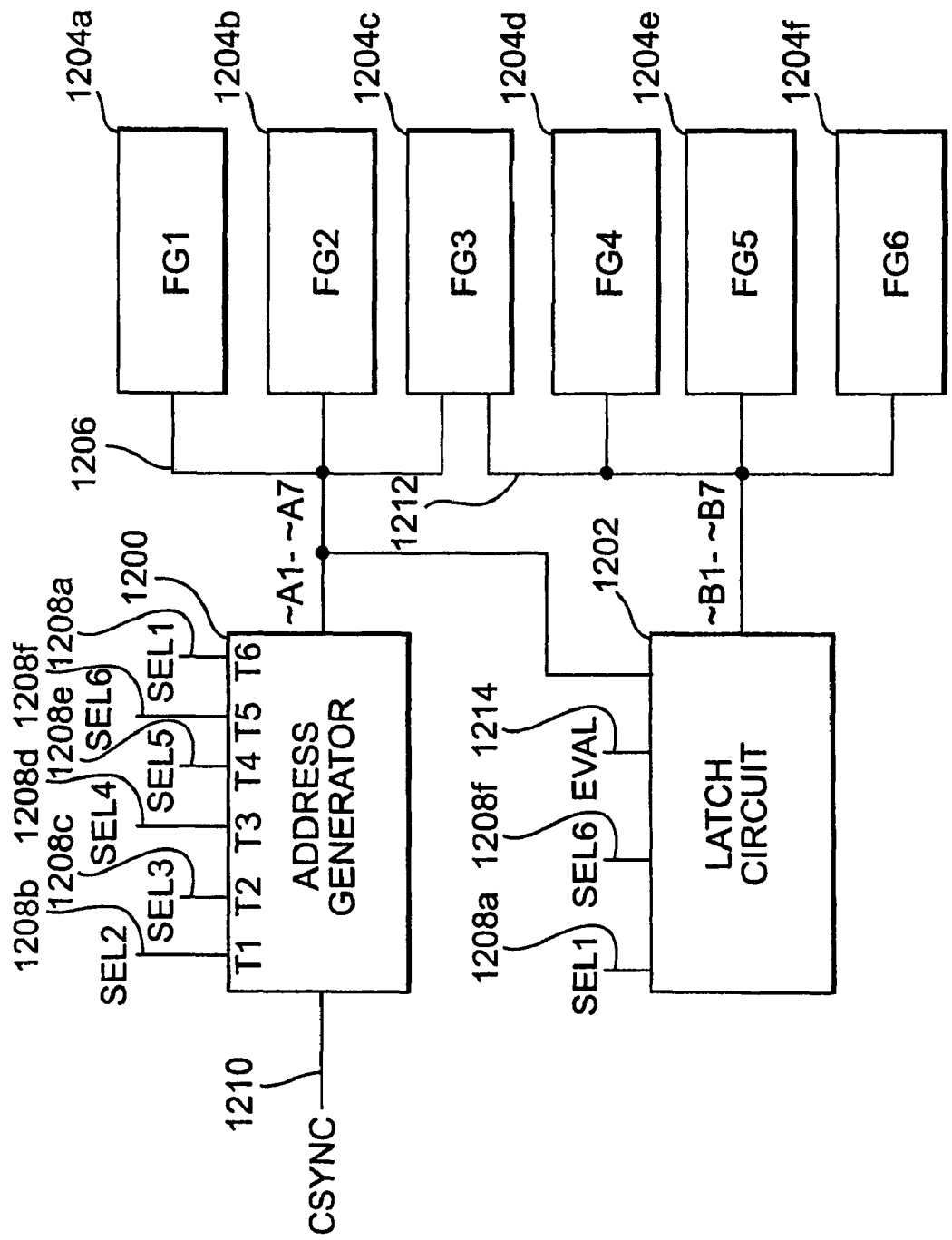
FIG. 15 is a block diagram illustrating one embodiment of an address generator, a latch circuit and six fire groups in a printhead die.

FIG. 15 is a block diagram illustrating one embodiment of an address generator 1200, a latch circuit 1202 and six fire groups 1204a-1204f in a printhead die 40. The address generator 1200 is similar to address generator 400 of FIG. 9 and fire groups 1204a-1204f are similar to fire groups 202a-202f illustrated in FIG. 7.

The address generator 1200 is electrically coupled to fire groups 1204a-1204c and to latch circuit 1202 through address lines 1206. Also, address generator 1200 is electrically coupled to control line 1210 that conducts control signal CSYNC to address generator 1200. In addition, address generator 1200 is electrically coupled to select lines 1208a-1208f. The select lines 1208a-1208f are similar to select lines 212a-212f illustrated in FIG. 7. The select lines 1208a-1208f conduct select signals SEL1, SEL2, . . . SEL6 to address generator 1200, as well as to the corresponding fire groups 1204a-1204f (not shown).

The select line 1208a conducts select signal SEL1 to address generator 1200, which in one embodiment is timing signal T6. The select line 1208b conducts select signal SEL2 to address generator 1200, which in one embodiment timing signal T1. The select line 1208c conducts select signal SEL3 to address generator 1200, which in one embodiment is timing signal T2. The select line 1208d conducts select signal SEL4 to address generator 1200, which in one embodiment is timing signal T3. The select line 1208e conducts select signal SEL5 to address generator 1200, which in one embodiment is timing signal T4, and the select line 1208f conducts select signal SEL6 to address generator 1200, which in one embodiment is timing signal T5.

The latch circuit 1202 is electrically coupled to fire groups 1204c-1204f through address lines 1212. Also, latch circuit 1202 is electrically coupled to select lines 1208a and 1208f and evaluation signal line 1214. The select lines 1208a and 1208f receive select signals SEL1 and SEL6 and provide the received select signals SEL1 and SEL6 to latch circuit 1202. The evaluation line 1214 conducts evaluation signal EVAL, which is similar to the inverse of select signal SEL1, to latch circuit 1202. In addition, latch circuit 1202 is electrically coupled to address lines 1206 that conducts the address signals ~A1, ~A2, . . . ~A7 to latch circuit 1202. In one embodiment, evaluation signal EVAL is generated on printhead die 40 from select signals SEL1, SEL2, SEL6.

The select signals SEL1, SEL2, . . . SEL6 provide a series of six pulses that repeats in a repeating series of six pulses, as described with respect to FIGS. 13 and 14. The control signal CSYNC includes pulses coincident with pulses in select signals SEL1, SEL2, . . . SEL6 to initiate address generator 1200 and to set up the direction of shifting and address generation in address generator 1200.

The address generator 1200 generates address signals ~A1, ~A2, . . . ~A7 in response to the select signals SEL1, SEL2, . . . SEL6 and control signal CSYNC. The address signals ~A1, ~A2, . . . ~A7 are provided through address lines 1206 to fire groups 1204a-1204c. In address generator 1200, address signals ~A1, ~A2, . . . ~A7 are valid during timing pulses in timing signals T6, T1 and T2 that correspond to timing pulses in select signals SEL1, SEL2 and SEL3. The control signal CSYNC includes a control pulse coincident with a timing pulse in timing signal T4 that corresponds to the timing pulse in select signal SEL5 to set up address generator 1200 for shifting in the forward direction. The control signal CSYNC includes a control pulse coincident with a timing pulse in timing signal T6 that corresponds to the timing pulse in select signal SEL1 to set up address generator 1200 for shifting in the reverse direction. To initiate address generation from address generator 1200, control signal CSYNC includes a control pulse coincident with a timing pulse in timing signal T2 that corresponds with the timing pulse in select signal SEL3.

The latch circuit 1202 provides address signals ~B1, ~B2, . . . ~B7 in response to receiving address signals ~A1, ~A2, . . . ~A7, select signals SEL1 and SEL6 and evaluation signal EVAL. The address latch 1202 receives valid address signals ~A1, ~A2, . . . ~A7 during the timing pulse in select signal SEL1 and latches in the valid address signals ~A1, ~A2, . . . ~A7 to provide address signals ~B1, ~B2, . . . ~B7. The address signals ~A1, ~A2, . . . ~A7 and ~B1, ~B2, . . . ~B7 provide the same address to fire groups 1204a-1204f during one address time slot. The address signals ~B1, ~B2, . . . ~B7 are provided through address lines 1212 to fire groups 1204c-1204f. The address signals ~B1, ~B2, . . . ~B7 are valid during timing pulses in select signals SEL3, SEL4, SEL5 and SEL6.

In one example operation, during one series of six pulses, control signal CSYNC includes a control pulse coincident with a timing pulse in select signal SEL5 to set up address generator 1200 for shifting in the forward direction or coincident with a timing pulse in select signal SEL1 for shifting in the reverse direction. Address generator 1200 is not initiated during this series of six pulses and, in this example, provides all high voltage level address signals ~A1, ~A2, . . . ~A7. The latch circuit 1202 latches in the high voltage level address signals ~A1, ~A2, . . . ~A7 to provide high voltage level address signals ~B1, ~B2, . . . ~B7.

In the next series of six timing pulses, control signal CSYNC includes a control pulse coincident with the timing pulse in select signal SEL5 or select signal SEL1 to set up the selected direction of shifting in address generator 1200. Also, control signal CSYNC includes a control pulse coincident with the timing pulse in select signal SEL3 to initiate address generator 1200 for generating valid address signals ~A1, ~A2, . . . ~A7. During this second series of six pulses, address generator 1200 provides all high voltage level address signals ~A1, ~A2, . . . ~A7 and latch 1202 latches in address signals ~A1, ~A2, . . . ~A7 to provide all high voltage level address signals ~B1, ~B2, . . . ~B7.

In the next series of six timing pulses, control signal CSYNC includes a control pulse coincident with the timing pulse in select signal SEL5 or SEL1 to set up the selected direction of shifting in address generator 1200. During this third series of six pulses, address generator 1200 provides valid address signals ~A1, ~A2, . . . ~A7 including low voltage level signals during the timing pulses from select signals SEL1, SEL2 and SEL3. The valid address signals ~A1, ~A2, . . . ~A7 are used for enabling firing cells 120 in row subgroups SG1, SG2 and SG3 in firing groups FG1, FG2 and FG3 at 1204a-1204c for activation. Latch circuit 1202 latches in the valid address signals ~A1, ~A2, . . . ~A7 and provides valid address signals ~B1, ~B2, . . . ~B7. The latch circuit 1202 provides the valid address signals ~B1, ~B2, . . . ~B7 during the timing pulses from select signals SEL3, SEL4, SEL5 and SEL6. The valid address signals ~B1, ~B2, . . . ~B7 are used for enabling firing cells 120 in row subgroups SG3, SG4, SG5 and SG6 in fire groups FG3, FG4, FG5 and FG6 at 1204c-1204f for activation.

During the third series of timing pulses from select signals SEL1, SEL2, . . . SEL6, address signals ~A1, ~A2, . . . ~A7 include low voltage level signals that correspond to one of thirteen addresses and address signals ~B1, ~B2, . . . ~B7 include low voltage level signals that correspond to the same one of the thirteen addresses. During each subsequent series of six pulses from select signals SEL1, SEL2, . . . SEL6, address signals ~A1, ~A2, . . . ~A7 and ~B1, ~B2, . . . ~B7 include low voltage level signals that correspond to the same one of thirteen addresses. Each series of timing pulses is an address time slot, such that one of the thirteen addresses is provided during each series of six pulses.

In forward direction operation, address one is provided first by address generator 1200 and latch circuit 1202, followed by address two and so on through address thirteen. After address thirteen, the address generator 1200 and latch circuit 1202 provide all high voltage level address signals ~A1, ~A2, ... ~A7 and ~B1, ~B2, ... ~B7.

In reverse direction operation, address thirteen is provided first by address generator 1200 and latch circuit 1202, followed by address twelve and so on through address one. After address one, address generator 1200 and latch circuit 1202 provide all high voltage level address signals ~A1, ~A2, ... ~A7 and ~B1, ~B2, ... ~B7. Also, during each series of six pulses from select signals SEL1, SEL2, ... SEL6, a control pulse is provided coincident with a timing pulse in select signal SEL5 or SEL1 to continue shifting in the selected direction.

Figure 16:
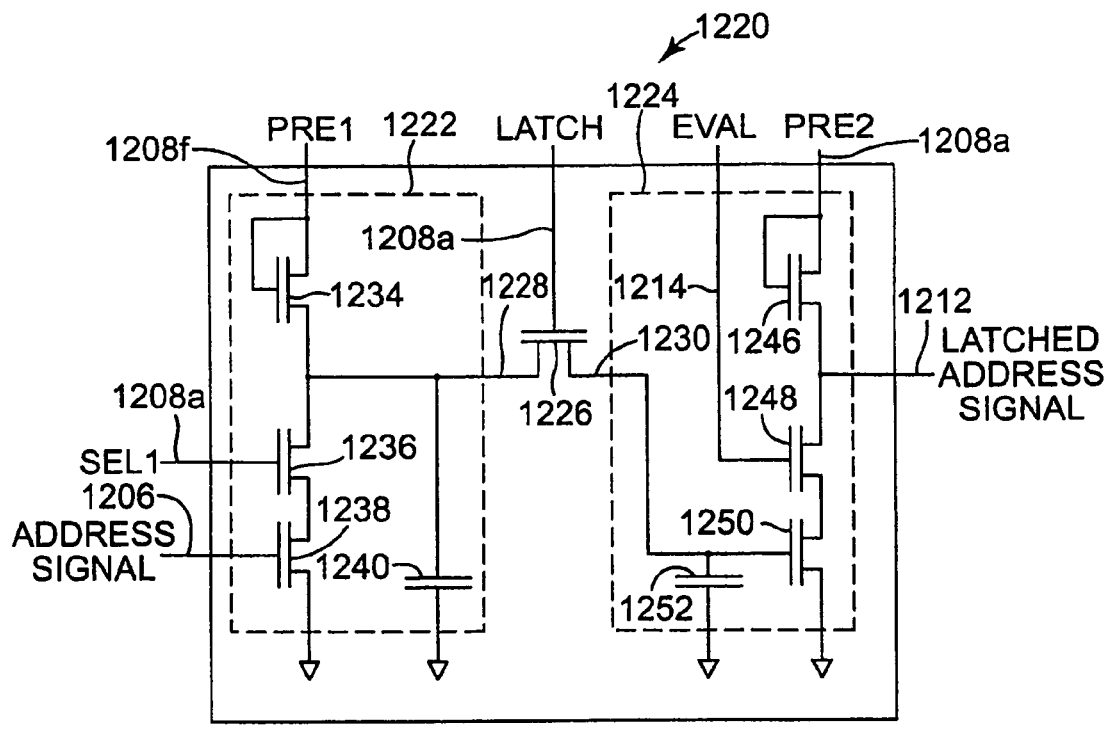
FIG. 16 is a diagram illustrating one embodiment of a latch register.

FIG. 16 is a diagram illustrating one embodiment of a latch register 1220. The latch circuit 1202 includes seven latch registers, such as latch register 1220. Each latch register 1220 latches in one of the seven address signals ~A1, ~A2, ... ~A7 and provides the corresponding latched address signals ~B1, ~B2, ... ~B7. The latch register 1220 includes a first latch stage 1222, a second latch stage 1224 and a latch transistor 1226. The first latch stage 1222 is electrically coupled at 1228 to one side of the drain-source path of latch transistor 1226 and the second latch stage 1224 is electrically coupled at 1230 to the other side of the drain-source path of latch transistor 1226. The gate of latch transistor 1226 is electrically coupled to signal line 1208a that conducts select signal SEL1 to latch transistor 1226 as latch signal LATCH.

The first latch stage 1222 includes a first pre-charge transistor 1234, a select transistor 1236, an address transistor 1238 and an address node capacitor 1240. The gate of the first pre-charge transistor 1234 is electrically coupled to the drain of first pre-charge transistor 1234 and to a signal line 1208f that conducts select signal SEL6 to first pre-charge transistor 1234 as first pre-charge signal PRE1. The source of first pre-charge transistor 1234 is electrically coupled at 1228 to one side of the drain-source path of latch transistor 1226 and to one side of address node capacitor 1240. The other side of address node capacitor 1240 is electrically coupled to a reference voltage, such as ground. In addition, the source of first pre-charge transistor 1234 is electrically coupled to one side of the drain-source path of select transistor 1236. The gate of select transistor 1236 is electrically coupled to select line 1208a that conducts select signal SEL1 to select transistor 1236. The other side of the drain-source path of select transistor 1236 is electrically coupled to one side of the drain-source path of address transistor 1238. The other side of the drain-source path of address transistor 1238 is electrically coupled to a reference voltage, such as ground. The gate of address transistor 1238 is electrically coupled to one of the address lines 1206.

The second latch stage 1224 includes a second pre-charge transistor 1246, an evaluation transistor 1248, a latched address transistor 1250 and a latched address node capacitor 1252. The gate of the second pre-charge transistor 1246 is electrically coupled to the drain of second pre-charge transistor 1246 and to signal line 1208a that conducts select signal SEL1 to the second pre-charge transistor 1246 as second pre-charge signal PRE2. The source of second pre-charge transistor 1246 is electrically coupled to one side of the drain-source path of evaluation transistor 1248 and to one of the latched address lines 1212. The gate of evaluation transistor 1248 is electrically coupled to evaluation signal line 1214. The other side of the drain-source path of evaluation transistor 1248 is electrically coupled to the drain-source path of latched address transistor 1250. The other side of the drain-source path of latched address transistor 1250 is electrically coupled to a reference voltage, such as ground. The gate of latched address transistor 1250 is electrically coupled at 1230 to the drain-source path of latch transistor 1226. In addition, the gate of latched address transistor 1250 is electrically coupled at 1230 to one side of latched address node capacitor 1252. The other side of latched address node capacitor 1252 is electrically coupled to a reference voltage, such as ground.

The first pre-charge transistor 1234 receives pre-charge signal PRE1 through signal line 1208f, and select transistor 1236 receives select signal SEL1 through signal line 1208a. If select signal SEL1 is set to a low voltage level and pre-charge signal PRE1 is set to a high voltage level, select transistor 1236 is turned off (non-conducting) and address node capacitor 1240 charges to a high voltage level through pre-charge transistor 1234.

The address transistor 1238 receives one of the address signals ~A1, ~A2, ... ~A7 through address line 1206. If the received address signal ~A1, ~A2, ... ~A7 is set to a high voltage level, address transistor 1238 is turned on (conducting) and if the received address signal ~A1, ~A2, ... ~A7 is set to a low voltage level, address transistor 1238 is turned off (non-conducting). Select transistor 1236 is turned on as select signal SEL1 transitions to a high voltage level. If address transistor 1238 is on, address node capacitor 1240 is discharged to a low voltage level. If address transistor 1238 is off and address node capacitor 1240 is charged to a high voltage level, address node capacitor 1240 is not discharged and remains at the high voltage level.

The latch transistor 1226 receives latch signal LATCH through signal line 1208a. If latch signal LATCH is set to a high voltage level, latch transistor 1226 is turned on and if latch signal LATCH is set to a low voltage level, latch transistor 1226 is turned off. The latch transistor 1226 is turned on to pass the voltage level on address node capacitor 1240 to latched address node capacitor 1252. The capacitance of the address node capacitor 1240 is about three times larger than the capacitance of the latched address node capacitor 1252 such that when charge is moved between address node capacitor 1240 and latched address node capacitor 1252, adequate high or low voltage levels remain on capacitors 1240 and 1252.

If latch transistor 1226 is off as address node capacitor 1240 charges to a high voltage level through first pre-charge transistor 1234, the voltage level on latched address node capacitor 1252 remains unchanged. The address node capacitor 1240 is pre-charged without affecting the second latch stage 1224 of latch register 1220, including the latched address signal on latched address line 1212. If the latch transistor 1226 is on as address node capacitor 1240 charges to a high voltage level through first pre-charge transistor 1234, latched address node capacitor 1252 is charged to a high voltage level and latched address transistor 1250 is turned on. The second latch stage 1224, including the latched address signal on latched address line 1212, is affected as the address node capacitor 1240 and latched address node capacitor 1252 are charged to a high voltage level through first pre-charge transistor 1234. In one embodiment, latch transistor 1226 is removed from between first latch stage 1222 and second latch stage 1224. In addition, latched address node capacitor 1252 can be removed and the capacitance value of address node capacitor 1240 can be reduced as the address node capacitor 1240 no longer needs to charge or discharge latched address node capacitor 1252. In this embodiment, address node capacitor 1240 is pre-charged through first pre-charge transistor 1234 to turn on latched address transistor 1250 in the second latch stage 1224 and pre-charging of address node capacitor 1240 is not isolated from second latch stage 1224.

The second pre-charge transistor 1246 receives pre-charge signal PRE2 through signal line 1208a, and evaluation transistor 1248 receives an evaluation signal EVAL through evaluation signal line 1214. If evaluation signal EVAL is set to a low voltage level and pre-charge signal PRE2 is set to a high voltage level, evaluation transistor 1248 is turned off and latched address line 1212 charges to a high voltage level through pre-charge transistor 1246.

The latch transistor 1226 is turned on to pass the voltage level on address node capacitor 1240 to latched address node capacitor 1252. A high voltage level turns on latched address transistor 1250 and a low voltage level turns off latched address transistor 1250. The evaluation signal EVAL is set to a high voltage level to turn on evaluation transistor 1248 and discharge the latched address signal to a low voltage level if latched address transistor 1250 is turned on. If the latched address transistor 1250 is off as evaluation transistor 1248 is turned on, the latched address line 1212 remains at a high voltage level. The latch transistor 1226 is turned off to latch in the voltage level on latched address node capacitor 1252 and the state of latched address transistor 1250.

In an example operation of one embodiment of latch register 1220, first pre-charge signal PRE1, select signal SEL1 and latch signal LATCH are set to a low voltage level. In addition, second pre-charge signal PRE2 is set to a low voltage level and evaluation signal EVAL is set to a high voltage level. With latch signal LATCH at a low voltage level, latch transistor 1226 is turned off to latch in the voltage level on latched address node capacitor 1252 that sets the on/off state of latched address transistor 1250. With evaluation signal EVAL set to a high voltage level, evaluation transistor 1248 is turned on to discharge the latched address signal if latched address transistor 1250 is turned on. With pre-charge signal PRE2 set to a low voltage level, the voltage level on latched address line 1212 corresponds to the state of latched address transistor 1250. If latched address transistor 1250 is on, latched address signal ~B1, ~B2, . . . ~B7 on latched address line 1212 is actively driven to a low voltage level. If latched address transistor 1250 is off, latched address signal ~B1, ~B2, . . . ~B7 on latched address line 1212 remains at a pre-charged high voltage level.

The first pre-charge signal PRE1 is set to a high voltage level to pre-charge address node capacitor 1240 to a high voltage level. As address node capacitor 1240 is charged to a high voltage level, a valid address signal ~A1, ~A2, . . . ~A7 is provided on address line 1206 to address transistor 1238. The valid address signal ~A1, ~A2, . . . ~A7 sets the on/off state of address transistor 1238 and pre-charge signal PRE1 transitions to a low voltage level at the end of the first pre-charge time period.

Next, select signal SEL1, latch signal LATCH and pre-charge signal PRE2 are set to a high voltage level and evaluation signal EVAL is set to a low voltage level. The select signal SEL1 turns on select transistor 1236 and latch signal LATCH turns on latch transistor 1226. If the valid address signal ~A1, ~A2, . . . ~A7 on signal line 1206 is at a high voltage level, address transistor 1238 is turned on and address node capacitor 1240 and latched address node capacitor 1252 are discharged to a low voltage level. If the valid address signal ~A1, ~A2, . . . ~A7 on signal line 1206 is at a low voltage level, address transistor 1238 is turned off and address node capacitor 1240 charges latched address node capacitor 1252 to a high voltage level. The inverse of the valid address signal ~A1, ~A2, . . . ~A7 received on signal line 1206 is stored on capacitors 1240 and 1252.

The voltage level on latched address capacitor 1252 sets the on/off state of latched address transistor 1250. With evaluation signal EVAL set to a low voltage level and pre-charge signal PRE2 set to a high voltage level, evaluation transistor 1248 is turned off and latched address line 1212 is charged to a high voltage level. The select signal SEL1, latch signal LATCH and pre-charge signal PRE2 are set to a low voltage level at the end of the select time period. With latch signal LATCH at a low voltage level, latch transistor 1226 is turned off to latch in the state of latched address transistor 1250.

Next, evaluation signal EVAL is set to a high voltage level to turn on evaluation transistor 1248. If the latched address node capacitor 1252 is charged to a high voltage level to turn on latch address transistor 1250, the latched address line 1212 is discharged to a low voltage level. If the latched address node capacitor 1252 is at a low voltage level to turn off latched address transistor 1250, latched address line 1212 remains charged to a high voltage level. Thus, the inverse of the address signal ~A1, ~A2, . . . ~A7 is present on the latched address node capacitor 1252 and the inverse of the voltage level on the latched address node capacitor 1252 is present on the latched address line 1212 as latched address signal ~B1, ~B2, . . . ~B7. The address signal ~A1, ~A2, . . . ~A7 is latched into latch register 1220 and provided as latched address signal ~B1, ~B2, . . . ~B7 on latched address line 1212. The latched address signal ~B1, ~B2, . . . ~B7 remains valid as pre-charge signal PRE1 is toggled high to charge address node capacitor 1240 with latch transistor 1226 turned off. The latched address signal ~B1, ~B2, . . . ~B7 becomes invalid as select signal SEL1, latch signal LATCH and pre-charge signal PRE2 are set to a high voltage level and evaluation signal EVAL is set to a low voltage level.

Figure 17:
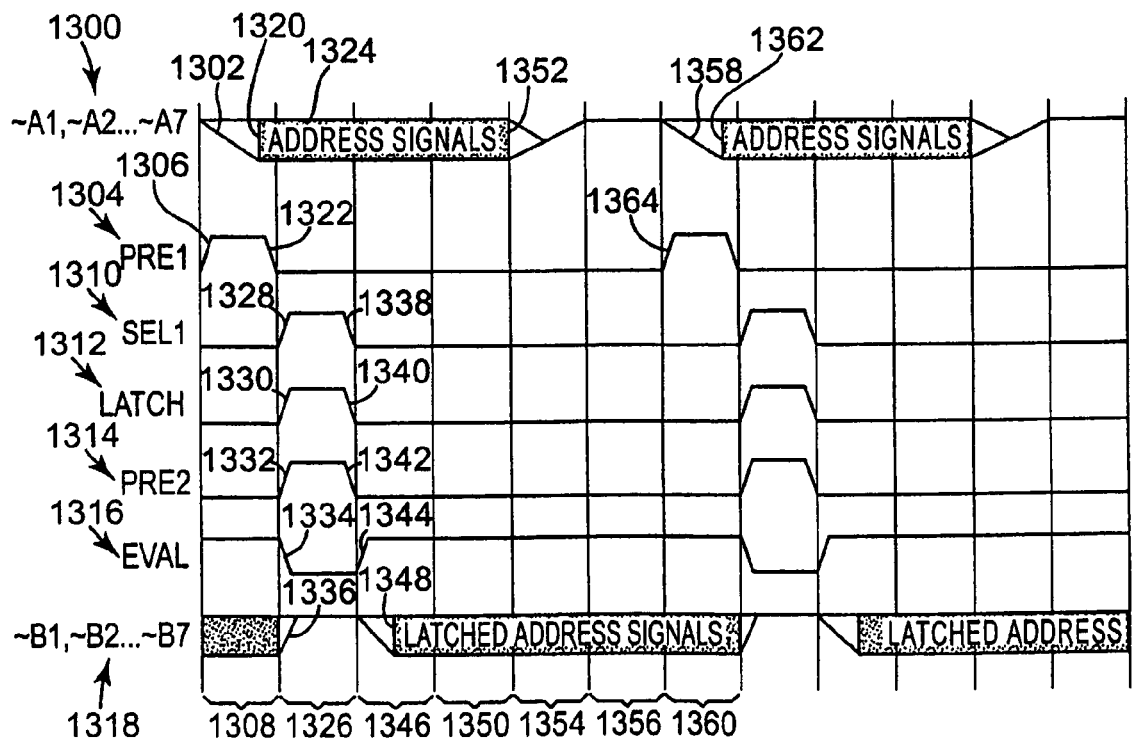
FIG. 17 is a timing diagram illustrating an example operation of one embodiment of a latch register.

FIG. 17 is a timing diagram illustrating an example operation of one embodiment of latch register 1220. Address signals ~A1, ~A2, . . . ~A7 at 1300 are in transition at 1302. Pre-charge signal PRE1 at 1304 is set to a high voltage level at 1306 for one time period, indicated at 1308. During time period 1308, select signal SEL1 at 1310 and latch signal LATCH at 1312 are set to a low voltage level to turn off select transistor 1236 and latch transistor 1226, respectively. The high voltage level of pre-charge signal PRE1 at 1306, charges address node capacitor 1240 through pre-charge transistor 1234. With latch transistor 1226 turned off, the voltage level on latched address node capacitor 1252 remains unchanged. In addition, during time period 1308, pre-charge signal PRE2 at 1314 is at a low voltage level and evaluation signal EVAL at 1316 is at a high voltage level to turn on evaluation transistor 1248. The latched address signal ~B1, ~B2, . . . ~B7 at 1318 remains unchanged.

The address signals ~A1, ~A2, . . . ~A7 at 1300 are provided by address generator 1200 and become valid address signals ~A1, ~A2, . . . ~A7 at 1320. One of the valid address signals ~A1, ~A2, . . . ~A7 at 1320 is provided on signal line 1206 to set the on/off state of address transistor 1238. The pre-charge signal PRE1 at 1304 transitions low at 1322 at the end of time period 1308.

The address signals ~A1, ~A2, . . . ~A7 at 1300 remain valid at 1324 during the next time period, indicated at 1326. During the time period at 1326, pre-charge signal PRE1 at 1304 remains at a low voltage level while select signal SEL1 at 1310 transitions to a high voltage level at 1328, latch signal LATCH at 1312 transitions to a high voltage level at 1330, pre-charge signal PRE2 at 1314 transitions to a high voltage level at 1332 and evaluation signal EVAL at 1316 transitions to a low voltage level at 1334. The valid address signal ~A1, ~A2, . . . ~A7 at 1324 sets the on/off state of address transistor 1238. With select signal SEL1 at 1310 set to a high voltage level and latch signal LATCH at 1312 set to a high voltage level, the voltage level on address node capacitor 1240 and latched address node capacitor 1252 is based on the state of address transistor 1238. If address transistor 1238 is turned on by the valid address signal ~A1, ~A2, . . . ~A7 at 1324, address node capacitor 1240 and latched address node capacitor 1252 are discharged to a low voltage level. If address transistor 1238 is turned off by the valid address signal ~A1, ~A2, . . . ~A7 at 1324, address node capacitor 1240 and latched address node capacitor 1252 remain at a high voltage level.

With pre-charge signal PRE2 at 1314 set to a high voltage level at 1332 and evaluation signal EVAL at 1316 set to a low voltage level at 1334, evaluation transistor 1248 is turned off and the latched address line 1212 is charged to a high voltage level through second pre-charge transistor 1246. As the evaluation signal EVAL at 1316 transitions to a low voltage level at 1334 and pre-charge signal PRE2 at 1314 transitions to a high voltage level at 1332, latched address signals ~B1, ~B2, . . . ~B7 at 1318 transition to invalid latched address signals at 1336. At the end of time period 1326, select signal SEL1 at 1310 transitions to a low voltage level at 1338 to turn off select transistor 1236, latch signal LATCH at 1312 transitions to a low voltage level at 1340 to turn off latch transistor 1226 and pre-charge signal PRE2 at 1314 transitions to a low voltage level at 1342 to stop charging latched address line 1212 through pre-charge transistor 1246. Turning off latch transistor 1226, latches in the voltage level on latched address node capacitor 1252 to turn on or off latched address transistor 1250.

The evaluation signal EVAL at 1316 transitions to a high voltage level at 1344, during the next time period, indicated at 1346. As the evaluation signal EVAL at 1316 transitions to a high voltage level at 1344, the latched address signals ~B1, ~B2, . . . ~B7 at 1318, including the signal on latched address line 1212, become valid at 1348. The address signals ~A1, ~A2, . . . ~A7 at 1300 provided by address generator 1200 remain valid during time period 1346. In addition, both the address signals ~A1, ~A2, . . . ~A7 at 1300 and the latched address signals ~B1, ~B2, . . . ~B7 at 1318 remain valid for the following time period, indicated at 1350.

The address signals ~A1, ~A2, . . . ~A7 at 1300 become invalid address signals at 1352, at the beginning of the time period indicated at 1354. In addition, address signals ~A1, ~A2, . . . ~A7 at 1300 remain invalid during the time period indicated at 1356. The latched address signals ~B1, ~B2, . . . ~B7 remain valid during time periods 1354 and 1356.

Address signals ~A1, ~A2, . . . ~A7 at 1300 are in transition at 1358, during the time period indicated at 1360, and become valid address signals ~A1, ~A2, . . . ~A7 at 1362. Pre-charge signal PRE1 at 1304 transitions to a high voltage level at 1364 and latched address signals ~B1, ~B2, . . . ~B7 are valid during time period 1360. Time period 1360 is similar to time period 1308 and the cycle repeats itself through time periods 1326, 1346, 1350, 1354 and 1356.

In this embodiment, the cycle includes six time periods, such as time periods 1326, 1346, 1350, 1354, 1356 and 1360. The address signals ~A1, ~A2, . . . ~A7 at 1300 are valid for three time periods 1326, 1346 and 1350 and the latched address signals ~B1, ~B2, . . . ~B7 at 1318 are valid for four time periods 1350, 1354, 1356 and 1360. Address signals ~A1, ~A2, . . . ~A7 at 1300 and latched address signals ~B1, ~B2, . . . ~B7 at 1318 are both valid during time period 1350. The latch register 1220 latches in address signals ~A1, ~A2, . . . ~A7 at 1300 while the latched address signals ~B1, ~B2, . . . ~B7 at 1318 are invalid for two time periods, such as time periods 1326 and 1346. In other embodiments, the number of time periods in a cycle can be set to any suitable number of time periods and the latch circuit 1202 can latch in address signals ~A1, ~A2, . . . ~A7 at 1300 in two or more time periods.

Figure 18:
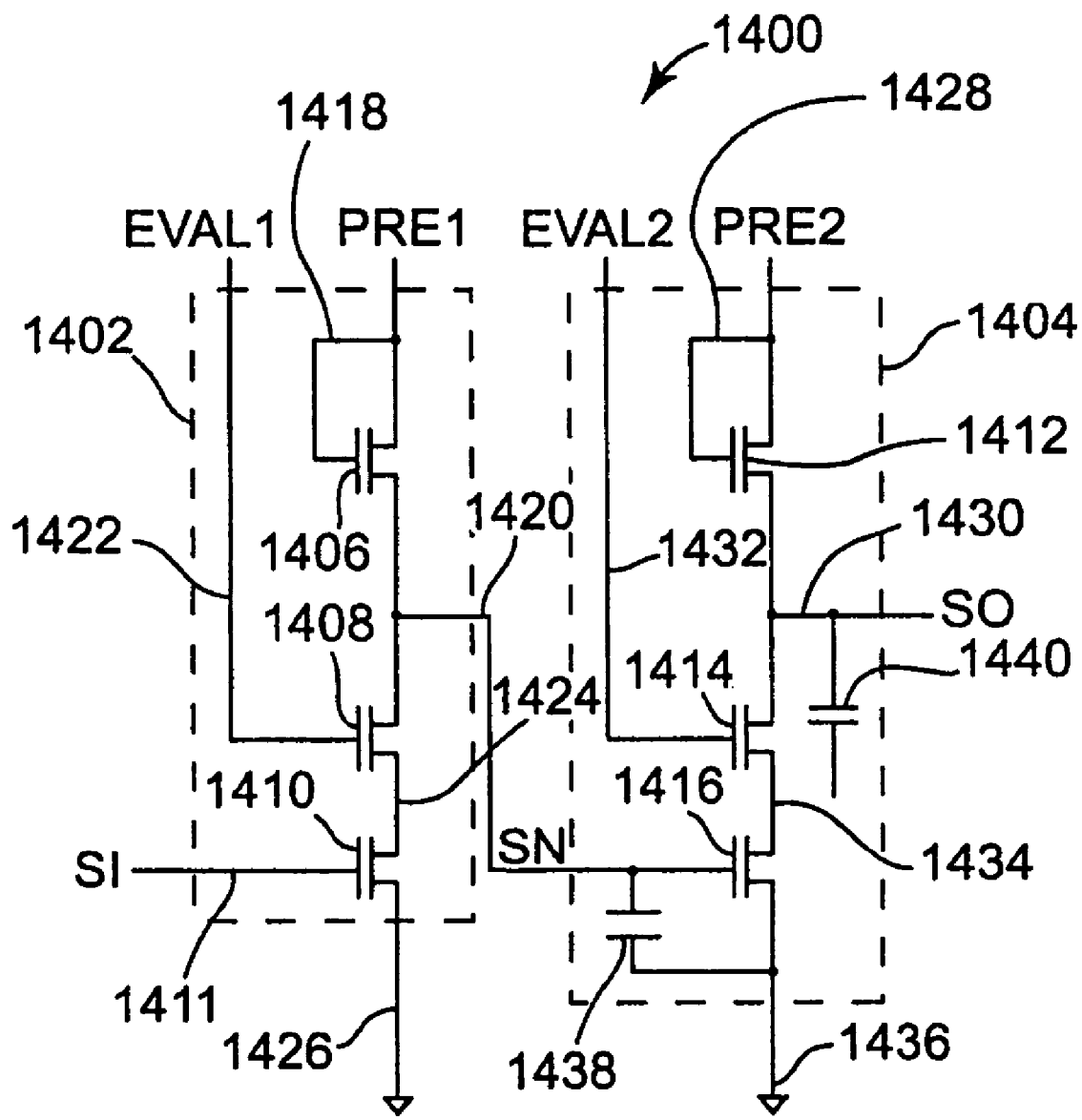
FIG. 18 is a diagram illustrating one embodiment of a single direction shift register cell.

FIG. 18 is a diagram illustrating one embodiment of a single direction shift register cell 1400 for use in other address generator embodiments that provide addresses in forward and reverse directions. The shift register cell 1400 includes a first stage that is an input stage, indicated with dashed lines at 1402, and a second stage that is an output stage, indicated with dashed lines at 1404. The first stage 1402 includes a first pre-charge transistor 1406, a first evaluation transistor 1408 and an input transistor 1410. The second stage 1404 includes a second pre-charge transistor 1412, a second evaluation transistor 1414 and an internal node transistor 1416.

In the first stage 1402, the gate and one side of the drain-source path of first pre-charge transistor 1406 is electrically coupled to first pre-charge line 1418. The first pre-charge line 1418 conducts timing pulses in first pre-charge signal PRE1 to shift register cell 1400. The other side of the drain-source path of first pre-charge transistor 1406 is electrically coupled to one side of the drain-source path of first evaluation transistor 1408 and the gate of internal node transistor 1416 through internal node 1420. The internal node 1420 provides internal node signal SN between stages 1402 and 1404 to the gate of internal node transistor 1416.

The gate of first evaluation transistor 1408 is electrically coupled to first evaluation signal line 1422 that conducts timing pulses in first evaluation signal EVAL1 to shift register cell 1400. The other side of the drain-source path of first evaluation transistor 1408 is electrically coupled to one side of the drain-source path of input transistor 1410 at 1424. The gate of input transistor 1410 is electrically coupled to the input line 1411. The other side of the drain-source path of input transistor 1410 is electrically coupled to a reference, such as ground, at 1426.

In the second stage 1404, the gate and one side of the drain-source path of second pre-charge transistor 1412 are electrically coupled to second pre-charge line 1428. The second pre-charge line 1428 conducts timing pulses in a second pre-charge signal PRE2 to shift register cell 1400. The other side of the drain-source path of second pre-charge transistor 1412 is electrically coupled to one side of the drain-source path of second evaluation transistor 1414 and shift register output line 1430. The gate of second evaluation transistor 1414 is electrically coupled to the second evaluation signal line 1432 that conducts second evaluation signal EVAL2 to shift register cell 1400. The other side of the drain-source path of second evaluation transistor 1414 is electrically coupled to one side of the drain-source path of internal node transistor 1416 at 1434. The other side of the drain-source path of internal node transistor 1416 is electrically coupled to a reference, such as ground, at 1436. The gate of the internal node transistor 1416 includes a capacitance 1438 for storing internal node signal SN. The shift register cell output line at 1430 includes a capacitance 1440 that stores the shift register cell output signal SO.

Shift register cell 1400 receives an input signal SI and through a series of pre-charge and evaluate operations, stores the value of input signal SI as output signal SO. The first stage 1402 receives input signal SI and stores the inverse of input signal SI as internal node signal SN. The second stage 1404 receives internal node signal SN and stores the inverse of internal node signal SN as output signal SO.

In operation, shift register cell 1400 receives a timing pulse in first pre-charge signal PRE1 that pre-charges internal node 1420 and internal node signal SN to a high voltage level through first pre-charge transistor 1406. Next, shift register cell 1400 receives a timing pulse in first evaluation signal EVAL1 that turns on first evaluation transistor 1408. If input signal SI is at a low voltage level that turns off input transistor 1410, internal node 1420 and internal node signal SN remain charged to a high voltage level. If input signal SI is at a high voltage level that turns on input transistor 1410, internal node 1420 and internal node signal SN discharge to a low voltage level.

Shift register cell 1400 receives a timing pulse in second pre-charge signal PRE2 that pre-charges output signal line 1430 and output signal SO to a high voltage level. Previous to the timing pulse in second pre-charge signal PRE2 the output line 1430 can store a valid output signal SO. Next, shift register cell 1400 receives a timing pulse in second evaluation signal EVAL2 that turns on second evaluation transistor 1414. If internal node signal SN is at a low voltage level that turns off internal node transistor 1416, output line 1430 and output signal SO remain charged to a high voltage level. If internal node signal SN is at a high voltage level that turns on internal node transistor 1416, output line 1430 and output signal SO are discharged to a low voltage level.

Figure 19:
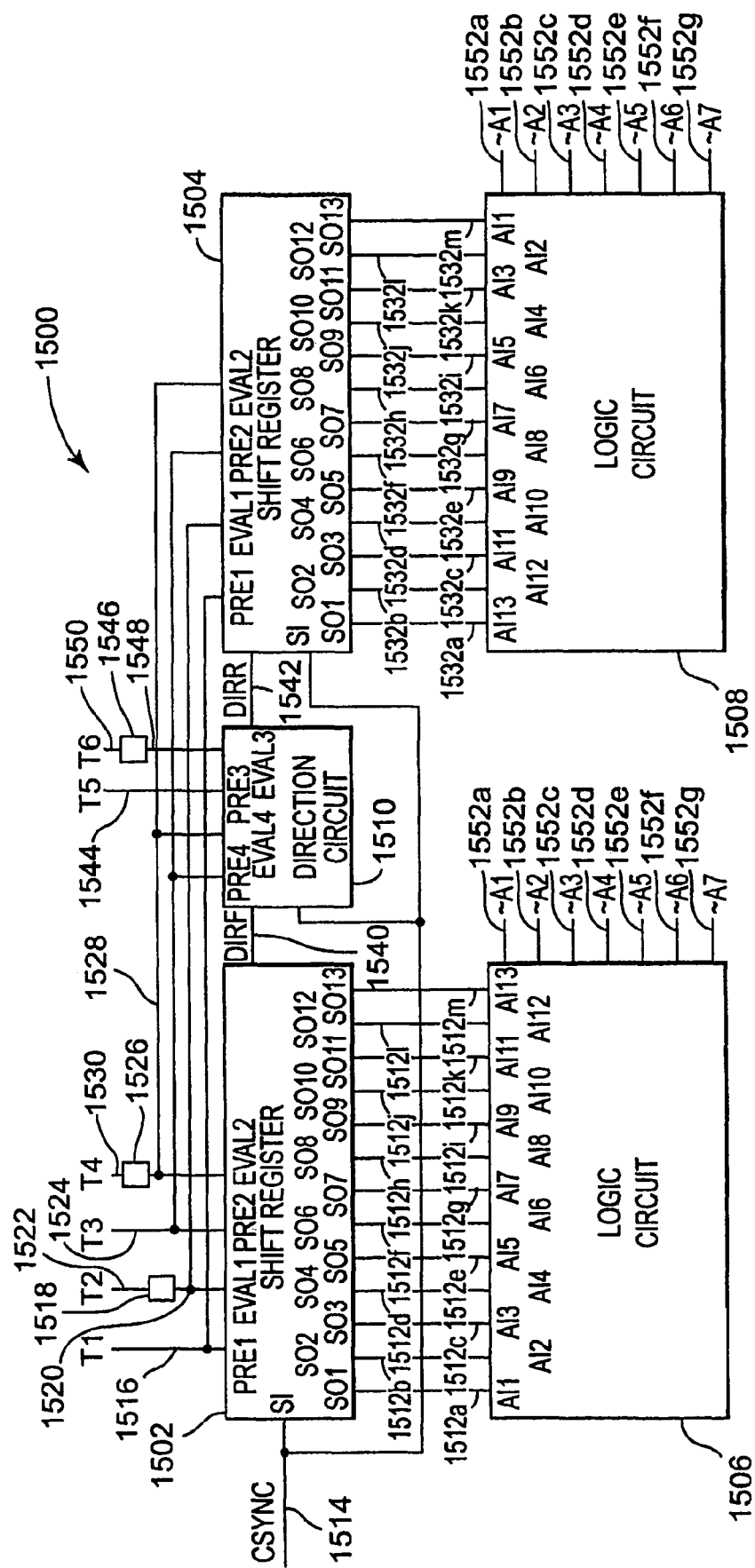
FIG. 19 is a diagram illustrating an address generator that uses the single direction shift register cell to provide addresses in forward and reverse directions.

FIG. 19 is a diagram illustrating an address generator 1500 that uses shift register cell 1400 to provide addresses in forward and reverse directions. The address generator 1500 includes a first shift register 1502, a second shift register 1504, a first logic circuit 1506, a second logic circuit 1508 and a direction circuit 1510.

The first shift register 1502 is electrically coupled to first logic circuit 1506 through shift register output lines 1512a-1512m. The shift register output lines 1512a-1512m provide shift register output signals SO1-SO13 to logic circuit 1506 as logic circuit input signals AI1-AI13, respectively. Also, first shift register 1502 is electrically coupled to control signal line 1514 that conducts control signal CSYNC to first shift register 1502. In addition, first shift register 1502 receives timing pulses from timing signals T1-T4.

First shift register 1502 is electrically coupled to first timing signal line 1516 that conducts timing signal T1 to first shift register 1502 as first pre-charge signal PRE1. First shift register 1502 is electrically coupled to first resistor divide network 1518 through first evaluation signal line 1520. The first resistor divide network 1518 is electrically coupled to second timing signal line 1522 that conducts timing signal T2 to first resistor divide network 1518. The first resistor divide network 1518 provides a reduced voltage level T2 timing signal to first shift register 1502 through first evaluation signal line 1520 as first evaluation signal EVAL1. First shift register 1502 is electrically coupled to third signal line 1524 that conducts timing signal T3 to first shift register 1502 as second pre-charge signal PRE2. First shift register 1502 is electrically coupled to second resistor divide network 1526 through second evaluation signal line 1528. The second resistor divide network 1526 is electrically coupled to fourth timing signal line 1530 that provides timing signal T4 to second resistor divide network 1526. The second resistor divide network 1526 provides a reduced voltage level T4 timing signal to first shift register 1502 through second evaluation signal line 1528 as second evaluation signal EVAL2.

The second shift register 1504 is electrically coupled to second logic circuit 1508 through shift register output lines 1532a-1532m. The shift register output lines 1532a-1532m conduct shift register output signals SO1-SO13 to logic circuit 1508 as logic circuit input signals AI13-AI1, respectively. Also, second shift register 1504 is electrically coupled to control signal line 1514 that conducts control signal CSYNC to second shift register 1504. In addition, second shift register 1504 receives timing pulses from timing pulses T1-T4.

Second shift register 1504 is electrically coupled to first timing signal line 1516 that conducts timing signal T1 to second shift register 1504 as first pre-charge signal PRE1. Second shift register 1504 is electrically coupled to first evaluation signal line 1520 that conducts a reduced voltage level T2 timing signal to second shift register 1504 as first evaluation signal EVAL1. Second shift register 1504 is electrically coupled to third timing signal line 1524 that conducts timing signal T3 to second shift register 1504 as second pre-charge signal PRE2. Second shift register 1504 is electrically coupled to second evaluation signal line 1528 that conducts a reduced voltage level T4 timing signal to second shift register 1504 as second evaluation signal EVAL2.

Direction circuit 1510 is electrically coupled to first shift register 1502 through forward direction signal line 1540 and to second shift register 1504 through reverse direction signal line 1542. The forward direction signal line 1540 conducts the forward direction signal DIRF from direction circuit 1510 to first shift register 1502. The reverse direction signal line 1542 conducts the reverse direction signal DIRR from direction circuit 1510 to second shift register 1504. Also, direction circuit 1510 is electrically coupled to control signal line 1514 that conducts control signal CSYNC to direction circuit 1510. In addition, direction circuit 1510 receives timing pulses from timing signals T3-T6.

Direction circuit 1510 is electrically coupled to third timing signal line 1524 that conducts timing signal T3 to direction circuit 1510 as fourth pre-charge signal PRE4. Direction circuit 1510 is electrically coupled to second evaluation signal line 1528 that conducts the reduced voltage T4 timing signal to direction circuit 1510 as fourth evaluation signal EVAL4. Also, direction circuit 1510 is electrically coupled to fifth timing signal line 1544 that conducts timing signal T5 to direction circuit 1510 as third pre-charge signal PRE3. In addition, direction circuit 1510 is electrically coupled to third resistor divide network 1546 through third evaluation signal line 1548. The third resistor divide network 1546 is electrically coupled to sixth timing signal line 1550 that conducts timing signal T6 to third resistor divide network 1546. The third resistor divide network 1546 provides a reduced voltage T6 timing signal to direction circuit 1510 as third evaluation signal EVAL3.

The first logic circuit 1506 is electrically coupled to shift register output lines 1512a-1512m to receive shift register output signals SO1-SO13 as input signals AI1-AI13, respectively. Also first logic circuit 1506 is electrically coupled to address lines 1552a-1552g to provide address signals ~A1, ~A2, . . . ~A7, respectively. The second logic circuit 1508 is electrically coupled to shift register output lines 1532a-1532m to receive shift register output signals SO1-SO13 as input signals AI13-AI1, respectively. Also, second logic circuit 1508 is electrically coupled to address lines 1552a-1552g to provide address signals ~A1, ~A2, . . . ~A7, respectively.

The first shift register 1502 and first logic circuit 1506 provide low voltage level signals in address signals ~A1, ~A2, . . . ~A7 to provide thirteen addresses as previously described. The first shift register 1502 and first logic circuit 1506 provide the thirteen addresses in a forward direction from address one to address thirteen. The second shift register 1504 and second logic circuit 1508 provide low voltage level signals in address signals ~A1, ~A2, . . . ~A7 to provide the thirteen addresses in a reverse direction from address thirteen to address one. The direction circuit 1510 conducts direction signals DIRF and DIRR that enable either first shift register 1502 for forward direction operation or second shift register 1504 for reverse direction operation.

The timing signals T1-T6 provide a series of six pulses in a repeating series of six pulses. Each timing signal T1-T6 includes one pulse in the series of six pulses and timing signals T1-T6 provide pulses in order from timing signal T1 to timing signal T6.

The first shift register 1502 includes thirteen shift register cells, such as shift register cell 1400. The thirteen shift register cells 1400 are electrically coupled in series with the output line 1430 of one electrically coupled to the input line 1411 of the next-in-line shift register cell 1400. The first shift register cell 1400 in the series receives control signal CSYNC as input signal SI and provides output signal SO1. The next shift register cell 1400 receives output signal SO1 as input signal SI and provides output signal SO2 and so on, through and including the last shift register cell 1400 that receives the previous output signal SO12 as input signal SI and provides output signal SO13.

First shift register 1502 is initiated by receiving a control pulse in control signal CSYNC coincident with a timing pulse in timing signal T2. In response, a single high voltage level signal is provided at SO1. During each subsequent series of six timing pulses, first shift register 1502 shifts the single high voltage level signal to the next shift register cell 1400 and shift register output signal SO2-SO13. The single high voltage level signal is shifted from shift register output signal SO1 to shift register output signal SO2 and so on, up to and including shift register output signal SO13. After shift register output signal SO13 has been set to a high voltage level, all shift register output signals SO1-SO13 are set to low voltage levels.

The first logic circuit 1506 is similar to logic circuit 406 (shown in FIG. 9). The first logic circuit 1506 receives the single high voltage level signal as an input signal AI1-AI13 and provides the corresponding low voltage level address signals in address signals ~A1, ~A2, . . . ~A7. In response to a high voltage level input signal AI1, first logic circuit 1506 provides address one address signals ~A1 and ~A2 at low voltage levels. In response to a high voltage level input signal AI2, first logic circuit 1506 provides address two address signals ~A1 and ~A3 at low voltage levels and so on, through and including a high voltage level input signal AI13 and first logic circuit 1506 providing address thirteen address signals ~A3 and ~A5 at low voltage levels.

The second shift register 1504 is similar to first shift register 1502. The second shift register 1502 provides a single high voltage level signal as shift register output signal SO1 in response to being initiated by a control pulse coincident with a timing pulse in timing signal T2. In response to each subsequent series of six pulses, the high voltage level signal is shifted to the next shift register cell 1400 and shift register output signal SO2-SO13. The high voltage level signal is shifted from shift register output signal SO1 to shift register output signal SO2 and so on, up to and including shift register output signal SO13. After shift register output signal SO13 has been set to a high voltage level, all shift register output signals SO1-SO13 are at low voltage levels.

The second logic circuit 1508 is similar to logic circuit 406 (shown in FIG. 9) and receives the high voltage level output signals SO1-SO13 as input signals AI13-AI1. The second logic circuit 1508 provides the thirteen addresses in reverse order from address thirteen to address one. In response to a high voltage level signal SO1, which is received as input signal AI13, second logic circuit 1508 provides address thirteen low voltage level address signals ~A3 and ~A5. Next, in response to a high voltage level signal SO2, which is received as input signal AI12, second logic circuit 1508 provides address twelve low voltage level address signals ~A3 and ~A4 and so on, up to and including in response to a high voltage level signal SO13, which is received as input signal AI1, second logic circuit 1508 provides address one low voltage level address signals ~A1 and ~A2.

The direction circuit 1510 is similar to direction circuit 404 of FIG. 10B. If direction circuit 1510 receives a control pulse in control signal CSYNC coincident with a timing pulse in timing signal T4, direction circuit 1510 provides a low voltage level direction signal DIRR and a high voltage level direction signal DIRF to shift in the forward direction, from address one to address thirteen. If direction circuit 1510 receives a control pulse coincidence with a timing pulse in timing signal T6, direction circuit 1510 provides a low voltage level direction signal DIRF and a high voltage level direction signal DIRR to shift in the reverse direction, from address thirteen to address one.

Each shift register 1502 and 1504 includes a direction transistor (not shown) in the first shift register cell 1400 in the series of shift register cells 1400. The direction transistor is situated in series with the input transistor 1410, similar to the series coupling of direction transistors 512 and 514 in shift register cell 403a illustrated in FIG. 10A. The direction transistor is electrically coupled between the drain-source path of input transistor 1410 and reference 1426. The direction transistor in the first shift register cell 1400 in the series of shift register cells 1400 operates similar to direction transistors 512 and 514 in shift register cell 403a of FIG. 10A. A high voltage level direction signal DIRF or DIRR turns on the direction transistor to enable the shift register 1502 or 1504 to be initiated by a control pulse in control signal CSYNC coincident with a timing pulse in timing signal T2. A low voltage level direction signal DIRF or DIRR turns off the direction transistor to disable the shift register 1502 or 1504.

In forward operation, in one series of six pulses direction circuit 1510 receives a control pulse in control signal CSYNC coincident with a timing pulse in timing signal T4 to provide address signals ~A1, ~A2, . . . ~A7 in the forward direction. The high voltage level direction signal DIRF enables first shift register 1502 and the low voltage level direction signal DIRR disables second shift register 1504.

In the next series of six pulses, a control pulse in control signal CSYNC is provided coincident with the timing pulse in timing signal T2. The control pulse coincident with the timing pulse in timing signal T2 initiates first shift register 1502 by discharging internal node 1420 through first evaluation transistor 1408, input transistor 1410 and the direction transistor (not shown). Second shift register 1504 is not initiated as it is disabled.

First shift register 1502 provides a single high voltage level output signal SO1 to first logic circuit 1506 that provides address one address signals ~A1, ~A2, . . . ~A7. Each subsequent series of six pulses, shifts the high voltage level signal to the next shift register output signal SO2-SO13. First logic circuit 1506 receives each high voltage level output signal SO1-SO13 and provides the corresponding addresses, from address one to address thirteen in address signals ~A1, ~A2, . . . ~A7. After shift register output signal SO13 has been high, all shift register output signals SO1-SO13 are set to low voltage levels and all address signals ~A1, ~A2, . . . ~A7 are set to high voltage levels.

In reverse operation, in one series of six pulses direction circuit 1510 receives a control pulse in control signal CSYNC coincident with a timing pulse in timing signal T6 to provide address signals ~A1, ~A2, . . . ~A7 in the reverse direction. The low voltage level direction signal DIRF disables first shift register 1502 and the high voltage level direction signal DIRR enables second shift register 1504.

In the next series of six pulses, a control pulse in control signal CSYNC is provided coincident with the timing pulse in timing signal T2. The control pulse coincident with the timing pulse in timing signal T2 initiates second shift register 1504 by discharging internal node 1420 through first evaluation transistor 1408, input transistor 1410 and the direction transistor (not shown). First shift register 1502 is not initiated as it is disabled.

Second shift register 1504 provides a single high voltage level output signal SO1 to second logic circuit 1508 that provides address thirteen address signals ~A1, ~A2, . . . ~A7. Each subsequent series of six pulses, shifts the high voltage level signal to the next shift register output signal SO2-SO13. Second logic circuit 1508 receives each high voltage level output signal SO1-SO13 and provides the corresponding addresses, from address thirteen to address one in address signals ~A1, ~A2, . . . ~A7. After shift register output signal SO1 has been high, all shift register output signals SO1-SO13 are set to low voltage levels and all address signals ~A1, ~A2, . . . ~A7 are set to high voltage levels.

Figure 20:
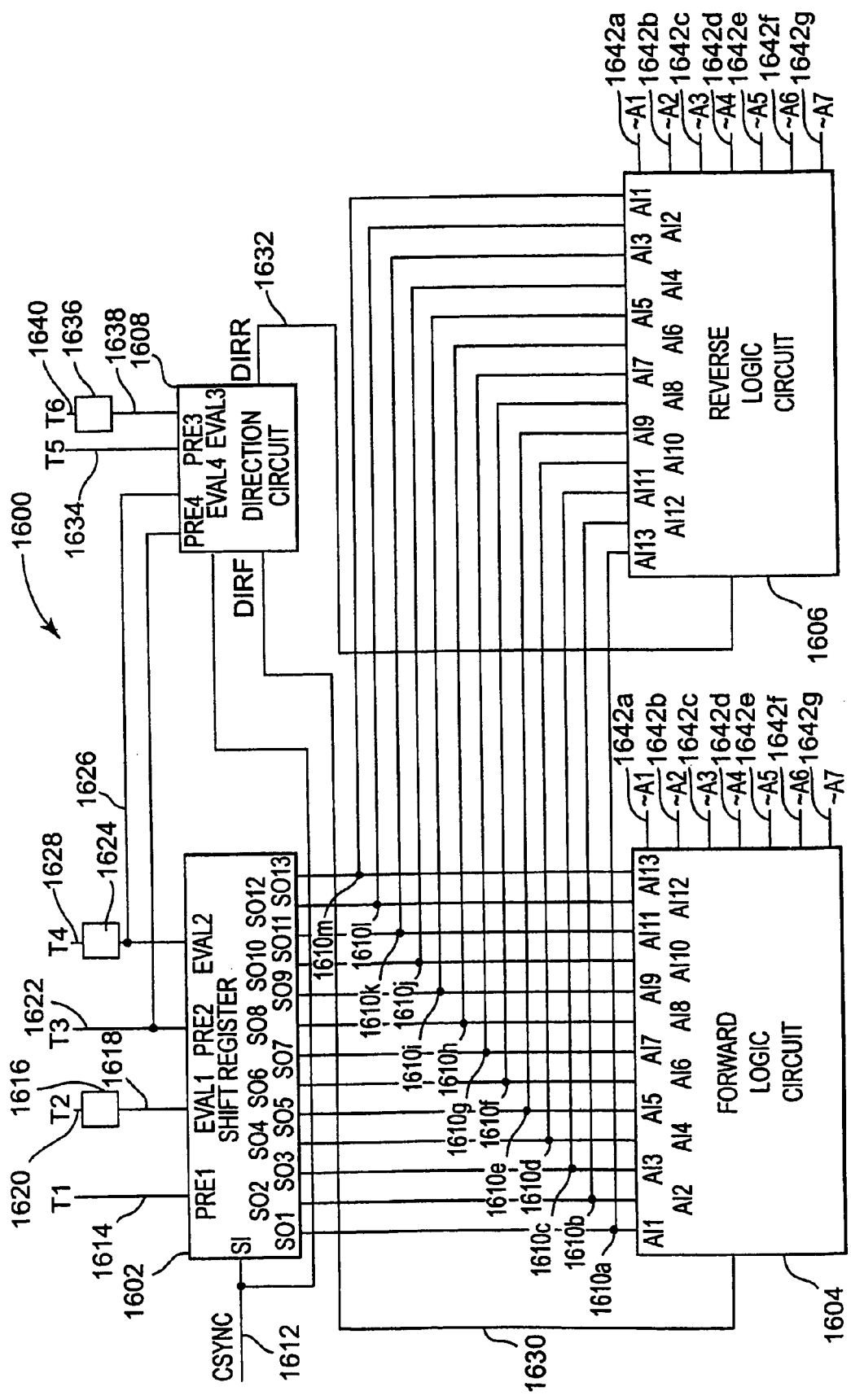
FIG. 20 is a diagram illustrating an address generator that uses the single direction shift register cell in one shift register to provide addresses in forward and reverse directions.

FIG. 20 is a diagram illustrating an address generator 1600 that uses shift register cell 1400 in one shift register 1602 to provide addresses in a forward direction and a reverse direction. The address generator 1600 includes shift register 1602, a forward logic circuit 1604, a reverse logic circuit 1606 and a direction circuit 1608.

The shift register 1602 is electrically coupled to forward logic circuit 1604 and reverse logic circuit 1606 by shift register output lines 1610a-1610m. The shift register output lines 1610a-1610m provide shift register output signals SO1-SO13 to forward logic circuit 1604 as input signals AI1-AI13, respectively. The shift register output lines 1610a-1610m provide shift register output signals SO1-SO13 to reverse logic circuit 1606 as input signals AI13-AI1, respectively. Also, shift register 1602 is electrically coupled to control signal line 1612 that provides control signal CSYNC to shift register 1602. In addition, shift register 1602 receives timing pulses from timing signals T1-T4.

Shift register 1602 is electrically coupled to first timing signal line 1614 that provides timing signal T1 to shift register 1602 as first pre-charge signal PRE1. Shift register 1602 is electrically coupled to first resistor divide network 1616 through first evaluation signal line 1618. The first resistor divide network 1616 is electrically coupled to second timing signal line 1620 that conducts timing signal T2 to first resistor divide network 1616. The first resistor divide network 1616 provides a reduced voltage level T2 timing signal to shift register 1602 through first evaluation signal line 1618 as first evaluation signal EVAL1. Shift register 1602 is electrically coupled to third timing signal line 1622 that provides timing signal T3 to shift register 1602 as second pre-charge signal PRE2. Shift register 1602 is electrically coupled to second resistor divide network 1624 through second evaluation signal line 1626. The second resistor divide network 1624 is electrically coupled to fourth timing signal line 1628 that conducts timing signal T4 to second resistor divide network 1624. The second resistor divide network 1624 provides a reduce voltage level T4 timing signal to shift register 1602 through second evaluation signal line 1626 as second evaluation signal EVAL2.

Direction circuit 1608 is electrically coupled to forward logic circuit 1604 through forward direction signal line 1630 and to reverse logic circuit 1606 through reverse direction signal line 1632. The forward direction signal line 1630 provides the forward direction signal DIRF from direction circuit 1608 to forward logic circuit 1604. The reverse direction signal line 1632 provides the reverse direction signal DIRR from direction circuit 1608 to reverse logic circuit 1606. Also, direction circuit 1608 is electrically coupled to control signal line 1612 that provides control signal CSYNC to direction circuit 1608. In addition, direction circuit 1608 receives timing pulses from timing signal T3-T6.

Direction circuit 1608 is electrically coupled to third timing signal line 1622 to receive timing signal T3 as fourth pre-charge signal PRE4 and to second evaluation signal line 1626 to receive the reduced voltage T4 timing signal as fourth evaluation signal EVAL4. Also, direction circuit 1608 is electrically coupled to fifth timing signal line 1634 that provides timing signal T5 to direction circuit 1608 as third pre-charge signal PRE3. In addition, direction circuit 1608 is electrically coupled to third resistor divide network 1636 through third evaluation signal line 1638. The third resistor divide network 1636 is electrically coupled to sixth timing signal line 1640 that provides timing signal T6 to third resistor divide network 1636. The third resistor divide network 1636 provides a reduced voltage T6 timing signal to direction circuit 1608 as third evaluation signal EVAL3.

The forward logic circuit 1604 is electrically coupled to shift register output lines 1610a-1610m to receive shift register output signals SO1-SO13 as input signals AI1-AI13, respectively. Also, forward logic circuit 1604 is electrically coupled to address lines 1642a-1642g to provide address signals ~A1, ~A2, . . . ~A7, respectively. The reverse logic circuit 1606 is electrically coupled to shift register output lines 1610a-1610m to receive shift register output signals SO1-SO13 as input signals AI13-AI1, respectively. Also, reverse logic circuit 1606 is electrically coupled to address lines 1642a-1642g to provide address signals ~A1, ~A2, . . . ~A7, respectively.

The shift register 1602 and the forward and reverse logic circuits 1604 and 1606 provide low voltage level signals in address signals ~A1, ~A2, . . . ~A7 to provide thirteen addresses as previously described. The shift register 1602 and forward logic circuit 1604 provide the thirteen addresses in a forward direction from address one to address thirteen. The shift register 1602 and reverse logic circuit 1606 provide the thirteen addresses in a reverse direction from address thirteen to address one. The direction circuit 1608 provides direction signals DIRF and DIRR that enable either forward logic circuit 1604 for forward direction operation or reverse logic circuit 1606 for reverse direction operation.

The timing signals T1-T6 provide a series of six pulses. Each timing signal T1-T6 provides one pulse in the series of six pulses and timing signals T1-T6 provide pulses in order from timing signal T1 to timing signal T6.

The shift register 1602 includes thirteen shift register cells such as shift register cell 1400. The thirteen shift register cells 1400 are electrically coupled in series with the output line 1430 of one electrically coupled to the input line 1411 of the next-in-line shift register cell 1400. The first shift register cell 1400 in the series receives control signal CSYNC as input signal SI and provides output signal SO1. The next shift register cell 1400 receives output signal SO1 as input signal SI and provides output signal SO2 and so on, through and including the last shift register cell 1400 that receives the previous output signal SO12 as input signal SI and provides output signals SO13.

Shift register 1602 is initiated by a control pulse in control signal CSYNC coincident with a timing pulse in timing signal T2. In response, a single high voltage level signal is provided at SO1. During each subsequent series of six timing pulses, shift register 1602 shifts the single high voltage level signal to the next shift register cell 1400 and shift register output signal SO1-SO13. The single high voltage level signal is shifted from shift register output signal SO1 to shift register output signal SO2 and so on, up to and including shift register output signal SO13. After shift register output signal SO13 has been set to a high voltage level, all shift register output signals SO1-SO13 are set to low voltage levels.

The forward logic circuit 1604 is similar to logic circuit 406 (shown in FIG. 9). The forward logic circuit 1604 receives the single high voltage level signal as an input signal AI1-AI13 and provides the corresponding low voltage level address signals in address signals ~A1, ~A2, . . . ~A7. In response to a high voltage level input signal AI1, forward logic circuit 1604 provides address one address signals ~A1 and ~A2 at low voltage levels. In response to a high voltage level input signal AI2, forward logic circuit 1604 provides address two address signals ~A1 and ~A3 at low voltage levels, and so on through and including a high voltage level input signal AI13 and forward logic circuit 1604 providing address thirteen address signals ~A3 and ~A5 at low voltage levels.

The reverse logic circuit 1606 is similar to logic circuit 406 (shown in FIG. 9) and receives the high voltage level output signals SO1-SO13 as input signals AI13-AI1, respectively. The reverse logic circuit 1606 provides the thirteen addresses in reverse order from address thirteen to address one. In response to a high voltage level signal SO1, which is received as input signal AI13, reverse logic circuit 1606 provides address thirteen address signals ~A3 and ~A5 at low voltage levels. Next, in response to a high voltage level signal SO2, which is received as input signal AI12, reverse logic circuit 1606 provides address twelve address signals ~A3 and ~A4 at low voltage levels, and so on up to and including in response to high voltage level SO13, which is received as input signal AI1, reverse logic circuit 1606 provides address one address signals ~A1 and ~A2 at low voltage levels.

The direction circuit 1608 is similar to direction circuit 404 of FIG. 10B. If direction circuit 1608 receives a control pulse in control signal CSYNC coincident with a timing pulse in timing signal T4, direction circuit 1608 provides a low voltage level direction signal DIRR and a high voltage level direction signal DIRF to shift in the forward direction, from address one to address thirteen. If direction circuit 1608 receives a control pulse coincident with a timing pulse in timing signal T6, direction circuit 1608 provides a low voltage level direction signal DIRF and a high voltage direction signal DIRR to shift in the reverse direction from address thirteen to address one.

In one embodiment, each logic circuit 1604 and 1606 includes a direction transistor situated in series with the logic evaluation line pre-charge transistor 444. In each logic circuit 1604 and 1606, the drain-source path of the direction transistor is electrically coupled between the drain-source path of logic evaluation line pre-charge transistor 444 and logic evaluation signal line 474. The gate of the direction transistor in forward logic circuit 1604 is electrically coupled to the forward direction line 1630 to receive the forward direction signal DIRF. The gate of the direction transistor in reverse logic transistor 1606 is electrically coupled to the reverse direction line 1632 to receive the reverse direction signal DIRR. In another embodiment, each logic circuit 1604 and 1606 includes a direction transistor situated in series with logic evaluation transistors 440. In each logic circuit 1604 and 1606, the drain-source path of the direction transistor is electrically coupled between each of the drain-source paths of logic evaluation transistors 440 and reference 478.

In one embodiment, a high voltage level direction signal DIRF turns on the direction transistor in forward logic circuit 1604 to enable the timing pulse in timing signal T5 to charge logic evaluation signal line 474, which turns on logic evaluation transistors 440 in forward logic circuit 1604 for providing address signals ~A1, ~A2, . . . ~A7 in the forward direction. A low voltage level direction signal DIRF turns off the direction transistor to disable forward logic circuit 1604. A high voltage level direction signal DIRR turns on the direction transistor in reverse logic circuit 1606 to enable the timing pulse in timing signal T5 to charge logic evaluation signal line 474, which turns on logic evaluation transistors 440 in reverse logic circuit 1606 for providing address signals ~A1, ~A2, . . . ~A7 in the reverse direction. A low voltage level direction signal DIRR turns off the direction transistor in reverse logic circuit 1606 to disable the reverse logic circuit 1606.

In forward operation, in one series of six pulses, direction circuit 1608 receives a control pulse in control signal CSYNC coincident with a timing pulse in timing signal T4 to provide address signals ~A1, ~A2, . . . ~A7 in the forward direction. The high voltage level direction signal DIRF enables forward logic circuit 1604 and the low voltage level direction signal DIRR disables reverse logic circuit 1606.

In the next series of six pulses, a control pulse in control signal CSYNC is provided coincident with the timing pulse in timing signal T2. The control pulse coincident with the timing pulse in timing signal T2 initiates shift register 1602. The shift register 1602 provides a single high voltage level output signal SO1 to forward logic circuit 1604 that provides address one address signals ~A1, ~A2, . . . ~A7. A control pulse in control signal CSYNC is also provided coincident with the timing pulse in timing signal T4 to continue providing address signals ~A1, ~A2, . . . ~A7 in the forward direction.

In each subsequent series of six pulses, a control pulse in control signal CSYNC is provided coincident with the timing pulse in timing signal T4 to continue providing the address signals ~A1, ~A2, . . . ~A7 in the forward direction. Also, in each subsequent series of six pulses, shift register 1602 shifts the high voltage level signal from one shift register output signal SO1-SO13 to the next shift register output signal SO1-SO13. Forward logic circuit 1604 receives each high level output signal SO1-SO13 and provides the corresponding address, from address one to address thirteen in address signals ~A1, ~A2, . . . ~A7. After shift register output signal SO13 has been high, all shift register output signals SO1-SO13 are set to low voltage levels and all address signals ~A1, ~A2, . . . ~A7 are set to high voltage levels.

In reverse operation, in one series of six pulses direction circuit 1608 receives a control pulse in control signal CSYNC coincident with a timing pulse in timing signal T6 to provide address signals ~A1, ~A2, . . . ~A7 in the reverse direction. The low voltage level direction signal DIRF disables forward logic circuit 1604 and the high voltage level direction signal DIRR enables reverse logic circuit 1606.

In the next series of six pulses, a control pulse in control signal CSYNC is provided coincident with the timing pulse in timing signal T2. The control pulse coincident with the timing pulse in timing signal T2 initiates shift register 1602. The shift register 1602 provides a single high voltage level output signal SO1 to reverse logic circuit 1606 as input signal AI13. The reverse logic circuit 1606 provides address thirteen address signals ~A1, ~A2, . . . ~A7. Also, a control pulse in control signal CSYNC is provided coincident with the timing pulse in timing signal T6 to continue providing address signals ~A1, ~A2, . . . ~A7 in the reverse direction.

In each subsequent series of six pulses, a control pulse in control signal CSYNC is provided coincident with the timing pulse in timing signal T6 to continue providing address signals ~A1, ~A2, . . . ~A7 in the reverse direction. Also, in each subsequent series of six pulses, shift register 1602 shifts the high voltage level signal from one shift register output signal SO1-SO13 to the next shift register output signal SO1-SO13. Reverse logic circuit 1606 receives each high voltage level output signal SO1-SO13 and provides the corresponding address from address thirteen to address one in address signals ~A1, ~A2, . . . ~A7. After shift register output signal SO1 has been high, all shift register output signals SO1-SO13 are set to low voltage levels and all address signals ~A1, ~A2, . . . ~A7 are set to high voltage levels.

Figure 21:
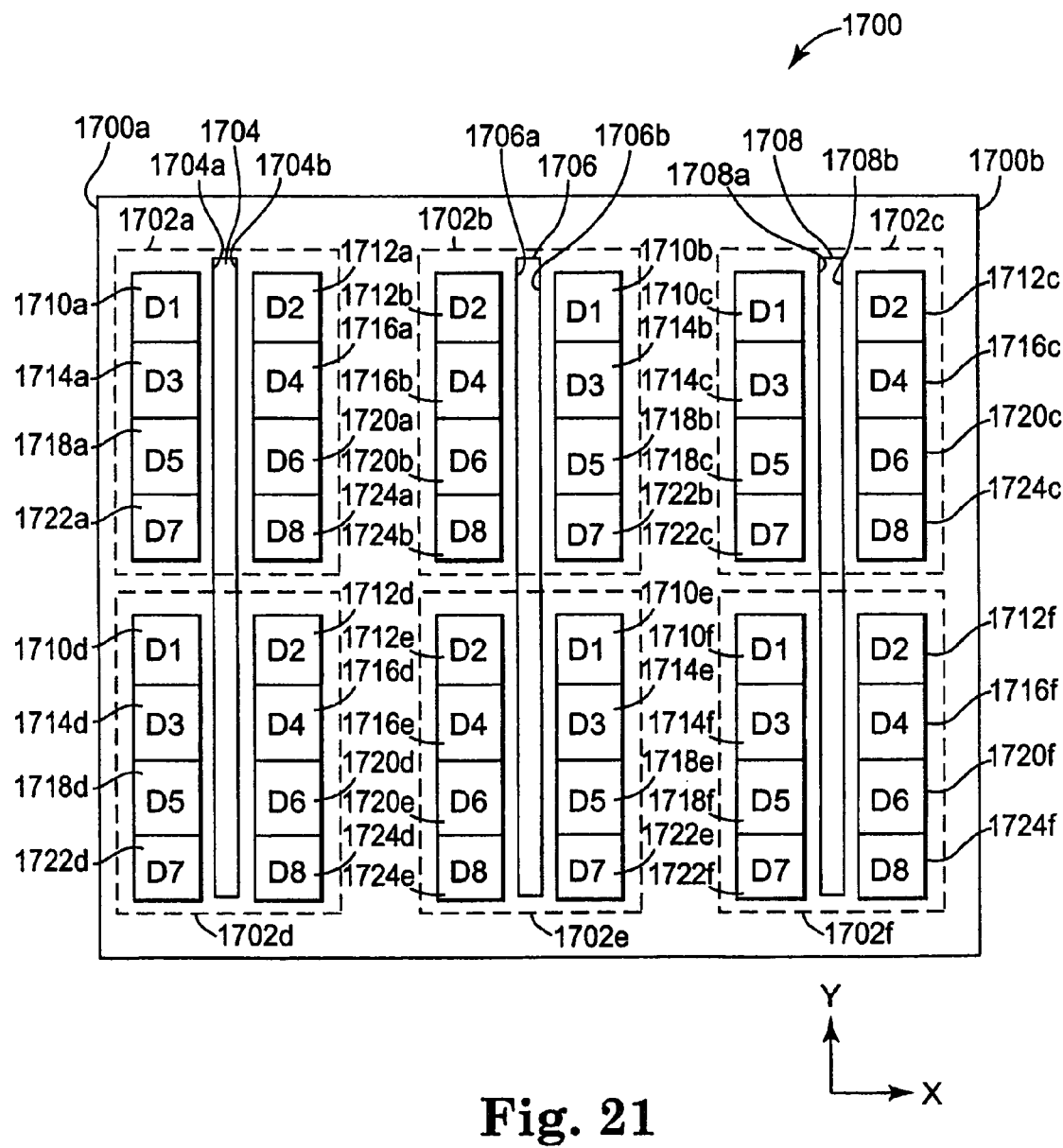
FIG. 21 is a diagram illustrating an example layout of one embodiment of a printhead die.

FIG. 21 is a diagram illustrating an example layout of one embodiment of a printhead die 1700. The printhead die 1700 includes six fire groups 1702a-1702f disposed along three ink fluid feed sources, here depicted as feed slots 1704, 1706 and 1708. Fire groups 1702a and 1702d are disposed along ink feed slot 1704, fire groups 1702b and 1702e are disposed along ink feed slot 1706 and fire groups 1702c and 1702f are disposed along ink feed slot 1708. The ink feed slots 1704, 1706 and 1708 are located parallel to one another and each ink feed slot 1704, 1706 and 1708 includes a length that extends along the y-direction of printhead die 1700. In one embodiment, each of the ink feed slots 1704, 1706 and 1708 supplies a different color ink to drop generators 60 in fire groups 1702a-1702f. In this embodiment, ink feed slot 1704 supplies yellow colored ink, ink feed slot 1706 supplies magenta colored ink and ink feed slot 1708 supplies cyan colored ink. In other embodiments, the ink feed slots 1704, 1706 and 1708 can supply any suitably colored ink of the same or different colors.

The fire groups 1702a-1702f are divided into eight data line groups, indicated at D1-D8. Each data line group D1-D8 includes pre-charged firing cells 120 from each of the fire groups 1702a-1702f. Each of the pre-charged firing cells 120 in a data line group D1-D8 is electrically coupled to one data line 208a-208h. Data line group D1, indicated at 1710a-1710f, includes pre-charged firing cells 120 electrically coupled to data line 208a. Data line group D2, indicated at 1712a-1712f, includes pre-charged firing cells 120 electrically coupled to data line 208b. Data line group D3, indicated at 1714a-1714f, includes pre-charged firing cells 120 electrically coupled to data line 208c. Data line group D4, indicated at 1716a-1716f, includes pre-charged firing cells 120 electrically coupled to data line 208d. Data line group D5, indicated at 1718a-1718f, includes pre-charged firing cells 120 electrically coupled to data line 208e. Data line group D6, indicated at 1720a-1720f, includes pre-charged firing cells 120 electrically coupled to data line 208f. Data line group D7, indicated at 1722a-1722f, includes pre-charged firing cells 120 electrically coupled to data line 208g, and data line group D8, indicated at 1724a-1724f, includes pre-charged firing cells 120 electrically coupled to data line 208h. Each of the pre-charged firing cells 120 in printhead die 1700 is electrically coupled to only one data line 208a-208h. Each data line 208a-208h is electrically coupled to all of the gates of the data transistors 136 in the pre-charged firing cells 120 of the corresponding data line group D1-D8.

Fire group one (FG1) 1702a is disposed along one half of the length of ink feed slot 1704. The ink feed slot 1704 includes opposing sides 1704a and 1704b that extend along the y-direction of printhead die 1700. The pre-charged firing cells 120 in printhead die 1700 include firing resistors 52 that are part of drop generators 60. The drop generators 60 in FG1 1702a are disposed along each of the opposing sides 1704a and 1704b of ink feed slot 1704. The drop generators 60 in FG1 1702a are fluidically coupled to the ink feed slot 1704 to receive ink from the ink feed slot 1704.

Drop generators 60 in data line groups D1, D3, D5 and D7, indicated at 1710a, 1714a, 1718a and 1722a, are disposed along one side 1704a of ink feed slot 1704 and drop generators 60 in data line groups D2, D4, D6 and D8, indicated at 1712a, 1716a, 1720a and 1724a, are disposed along the opposing side 1704b of ink feed slot 1704. The drop generators 60 in data line groups D1, D3, D5 and D7 at 1710a, 1714a, 1718a and 1722a are disposed between one side 1700a of printhead die 1700 and ink feed slot 1704, and drop generators 60 in data line groups D2, D4, D6 and D8 at 1712a, 1716a, 1720a and 1724a are disposed along an inside routing channel of printhead die 1700 between ink feed slot 1704 and ink feed slot 1706. In one embodiment, drop generators 60 in data line groups D1, D3, D5 and D7 at 1710a, 1714a, 1718a and 1722a are disposed along the length of one side 1704a of ink feed slot 1704 and drop generators 60 for data line groups D2, D4, D6 and D8 at 1712a, 1716a, 1720a and 1724a are disposed along the opposing side 1704b of ink feed slot 1704. The drop generators 60 in data line group D1 at 1710a are opposite drop generators 60 in data line group D2 at 1712a. The drop generators 60 in data line group D3 at 1714a are opposite drop generators 60 in data line group D4 at 1716a. The drop generators 60 in data line group D5 at 1718a are opposite drop generators 60 in data line group D6 at 1720a, and drop generators 60 in data line group D7 at 1722a are opposite drop generators 60 in data line group D8 at 1724a.

Fire group four (FG4) 1702d is disposed along the other half of the length of ink feed slot 1704. The drop generators 60 in FG4 1702d are disposed along opposing sides 1704a and 1704b of ink feed slot 1704 and fluidically coupled to ink feed slot 1704 to receive ink from ink feed slot 1704. Drop generators 60 in data line groups D1, D3, D5 and D7, indicated at 1710d, 1714d, 1718d and 1722d, are disposed along one side 1704a of ink feed slot 1704 and drop generators 60 in data line groups D2, D4, D6 and D8, indicated at 1712d, 1716d, 1720d and 1724d, are disposed along the opposing side 1704b of ink feed slot 1704. The drop generators 60 in data line groups D1, D3, D5 and D7 at 1710d, 1714d, 1718d and 1722d are disposed between one side 1700a of printhead die 1700 and ink feed slot 1704, and drop generators 60 in data line groups D2, D4, D6 and D8 at 1712d, 1716d, 1720d and 1724d are disposed along an inside routing channel of printhead die 1700 between ink feed slot 1704 and ink feed slot 1706. In one embodiment, drop generators 60 in data line groups D1, D3, D5 and D7 at 1710d, 1714d, 1718d and 1722d are disposed along the length of one side 1704a of ink feed slot 1704 and drop generators 60 for data line groups D2, D4, D6 and D8 at 1712d, 1716d, 1720d and 1724d are disposed along the opposing side 1704b of ink feed slot 1704. The drop generators 60 in data line group D1 at 1710d are opposite drop generators 60 in data line group D2 at 1712d. The drop generators 60 in data line group D3 at 1714d are opposite drop generators 60 in data line group D4 at 1716d. The drop generators 60 in data line group D5 at 1718d are opposite drop generators 60 in data line group D6 at 1720d, and drop generators 60 in data line group D7 at 1722d are opposite drop generators 60 in data line group D8 at 1724d.

Fire group two (FG2) 1702b is disposed along one half of the length of ink feed slot 1706. The ink feed slot 1706 includes opposing sides 1706a and 1706b that extend along the y-direction of printhead die 1700. The drop generators 60 in FG2 1702b are disposed along each of the opposing sides 1706a and 1706b of ink feed slot 1706. The drop generators 60 in FG2 1702*b* are fluidically coupled to the ink feed slot 1706 to receive ink from ink feed slot 1706.

Drop generators 60 in data line groups D1, D3, D5 and D7, indicated at 1710*b*, 1714*b*, 1718*b* and 1722*b*, are disposed along one side 1706*b* of ink feed slot 1706, and drop generators 60 in data line groups D2, D4, D6 and D8, indicated at 1712*b*, 1716*b*, 1720*b* and 1724*b*, are disposed along the opposing side 1706*a* of ink feed slot 1706. The drop generators 60 in data line groups D1, D3, D5 and D7 at 1710*b*, 1714*b*, 1718*b* and 1722*b* are disposed along an inside channel between ink feed slot 1706 and ink feed slot 1708, and drop generators 60 in data line groups D2, D4, D6 and D8 at 1712*b*, 1716*b*, 1720*b* and 1724*b* are disposed along an inside channel between ink feed slot 1704 and ink feed slot 1706. In one embodiment, drop generators 60 in data line groups D1, D3, D5 and D7 at 1710*b*, 1714*b*, 1718*b* and 1722*b* are disposed along the length of one side 1706*b* of ink feed slot 1706 and drop generators 60 for data line groups D2, D4, D6 and D8 at 1712*b*, 1716*b*, 1720*b* and 1724*b* are disposed along the opposing side 1706*a* of ink feed slot 1706. The drop generators 60 in data line group D1 at 1710*b* are opposite drop generators 60 in data line group D2 at 1712*b*. The drop generators 60 in data line group D3 at 1714*b* are opposite drop generators 60 in data line group D4 at 1716*b*. The drop generators 60 in data line group D5 at 1718*b* are opposite drop generators 60 in data line group D6 at 1720*b*, and drop generators 60 in data line group D7 at 1722*b* are opposite drop generators 60 in data line group D8 at 1724*b*.

Fire group five (FG5) 1702*e* is disposed along the other half of the length of ink feed slot 1706. The drop generators 60 in FG5 1702*e* are disposed along opposing sides 1706*a* and 1706*b* of ink feed slot 1706 and fluidically coupled to ink feed slot 1706 to receive ink from ink feed slot 1706. Drop generators 60 in data line groups D1, D3, D5 and D7, indicated at 1710*e*, 1714*e*, 1718*e* and 1722*e*, are disposed along one side 1706*b* of ink feed slot 1706 and drop generators 60 in data line groups D2, D4, D6 and D8, indicated at 1712*e*, 1716*e*, 1720*e* and 1724*e*, are disposed along the opposing side 1706*a* of ink feed slot 1706. The drop generators 60 in data line groups D1, D3, D5 and D7 at 1710*e*, 1714*e*, 1718*e* and 1722*e* are disposed along an inside channel between ink feed slot 1706 and ink feed slot 1708, and drop generators 60 in data line groups D2, D4, D6 and D8 at 1712*e*, 1716*e*, 1720*e* and 1724*e* are disposed along an inside channel of printhead die 1700 between ink feed slot 1704 and ink feed slot 1706. In one embodiment, drop generators 60 in data line groups D1, D3, D5 and D7 at 1710*e*, 1714*e*, 1718*e* and 1722*e* are disposed along the length of one side 1706*b* of ink feed slot 1706 and drop generators 60 for data line groups D2, D4, D6 and D8 at 1712*e*, 1716*e*, 1720*e* and 1724*e* are disposed along the opposing side 1706*a* of ink feed slot 1706. The drop generators 60 in data line group D1 at 1710*e* are opposite drop generators 60 in data line group D2 at 1712*e*. The drop generators 60 in data line group D3 at 1714*e* are opposite drop generators 60 in data line group D4 at 1716*e*. The drop generators 60 in data line group D5 at 1718*e* are opposite drop generators 60 in data line group D6 at 1720*e*, and drop generators 60 in data line group D7 at 1722*e* are opposite drop generators 60 in data line group D8 at 1724*e*.

Fire group three (FG3) 1702*c* is disposed along one half of the length of ink feed slot 1708. Ink feed slot 1708 includes opposing sides 1708*a* and 1708*b* that extend along the y-direction of printhead die 1700. The drop generators 60 in FG3 1702*c* are disposed along each of the opposing sides 1708*a* and 1708*b* of ink feed slot 1708. The drop generators 60 in FG3 1702*c* are fluidically coupled to the ink feed slot 1708 to receive ink from ink feed slot 1708.

Drop generators 60 in data line groups D1, D3, D5 and D7, indicated at 1710*c*, 1714*c*, 1718*c* and 1722*c*, are disposed along one side 1708*a* of ink feed slot 1708, and drop generators 60 in data line groups D2, D4, D6 and D8, indicated at 1712*c*, 1716*c*, 1720*c* and 1724*c*, are disposed along the opposing side 1708*b* of ink feed slot 1708. The drop generators 60 in data line groups D1, D3, D5 and D7 at 1710*c*, 1714*c*, 1718*c* and 1722*c* are disposed along an inside channel between ink feed slot 1706 and ink feed slot 1708, and drop generators 60 in data line groups D2, D4, D6 and D8 at 1712*c*, 1716*c*, 1720*c* and 1724*c* are disposed between one side 1700*b* of printhead die 1700 and ink feed slot 1708. In one embodiment, drop generators 60 in data line groups D1, D3, D5 and D7 at 1710*c*, 1714*c*, 1718*c* and 1722*c* are disposed along the length of one side 1708*a* of ink feed slot 1708 and drop generators 60 for data line groups D2, D4, D6 and D8 at 1712*c*, 1716*c*, 1720*c* and 1724*c* are disposed along the opposing side 1708*b* of ink feed slot 1708. The drop generators 60 in data line group D1 at 1710*c* are opposite drop generators 60 in data line group D2 at 1712*c*. The drop generators 60 in data line group D3 at 1714*c* are opposite drop generators 60 in data line group D4 at 1716*c*. The drop generators 60 in data line group D5 at 1718*c* are opposite drop generators 60 in data line group D6 at 1720*c*, and drop generators 60 in data line group D7 at 1722*c* are opposite drop generators 60 in data line group D8 at 1724*c*.

Fire group six (FG6) 1702*f* is disposed along the other half of the length of ink feed slot 1708. The drop generators 60 in FG6 1702*f* are disposed along opposing sides 1708*a* and 1708*b* of ink feed slot 1708 and fluidically coupled to ink feed slot 1708 to receive ink from ink feed slot 1708. Drop generators 60 in data line groups D1, D3, D5 and D7, indicated at 1710*f*, 1714*f*, 1718*f* and 1722*f*, are disposed along one side 1708*a* of ink feed slot 1708 and drop generators 60 in data line groups D2, D4, D6 and D8, indicated at 1712*f*, 1716*f*, 1720*f* and 1724*f*, are disposed along the opposing side 1708*b* of ink feed slot 1708. The drop generators 60 in data line groups D1, D3, D5 and D7 at 1710*f*, 1714*f*, 1718*f* and 1722*f* are disposed along an inside channel between ink feed slot 1706 and ink feed slot 1708, and drop generators 60 in data line groups D2, D4, D6 and D8 at 1712*f*, 1716*f*, 1720*f* and 1724*f* are disposed between one side 1700*b* of printhead die 1700 and ink feed slot 1708. In one embodiment, drop generators 60 in data line groups D1, D3, D5 and D7 at 1710*f*, 1714*f*, 1718*f* and 1722*f* are disposed along the length of one side 1708*a* of ink feed slot 1708 and drop generators 60 for data line groups D2, D4, D6 and D8 at 1712*f*, 1716*f*, 1720*f* and 1724*f* are disposed along the opposing side 1708*b* of ink feed slot 1708. The drop generators 60 in data line group D1 at 1710*f* are opposite drop generators 60 in data line group D2 at 1712*f*. The drop generators 60 in data line group D3 at 1714*f* are opposite drop generators 60 in data line group D4 at 1716*f*. The drop generators 60 in data line group D5 at 1718*f* are opposite drop generators 60 in data line group D6 at 1720*f*, and drop generators 60 in data line group D7 at 1722*f* are opposite drop generators 60 in data line group D8 at 1724*f*.

Drop generators 60 between ink feed slot 1704 and one side 1700*a* of printhead die 1700 are in data line groups D1 at 1710*a* and 1710*d*, D3 at 1714*a* and 1714*d*, D5 at 1718*a* and 1718*d* and D7 at 1722*a* and 1722*d*. Drop generators 60 between ink feed slot 1708 and the other side 1700*b* of printhead die 1700 are in data line groups D2 at 1712*c* and 1712*f*, D4 at 1716*c* and 1716*f*, D6 at 1720*c* and 1720*f* and D8 at 1724*c* and 1724*f*. Thus, four data lines 208*a*, 208*c*, 208*e* and 208*g* are routed between ink feed slot 1704 and one side 1700*a* of printhead die 1700, as opposed to routing all eight data lines 208*a*-208*h*. Also, four data lines 208*b*, 208*d*, 208*f* and 208h are routed between ink feed slot 1708 and the other side 1700b of printhead die 1700, as opposed to routing all eight data lines 208a-208h.

In addition, drop generators 60 between ink feed slots 1704 and 1706 are in data line groups D2 at 1712a, 1712b, 1712d and 1712e, D4 at 1716a, 1716b, 1716d and 1716e, D6 at 1720a, 1720b, 1720d and 1720e, and D8 at 1724a, 1724b, 1724d and 1724e. Also, drop generators 60 between ink feed slots 1706 and 1708 are in data line groups D1 at 1710b, 1710c, 1710e and 1710f, D3 at 1714b, 1714c, 1714e and 1714f, D5 at 1718b, 1718c, 1718e and 1718f, and D7 at 1722b, 1722c, 1722e and 1722f. Thus, four data lines 208b, 208d, 208f and 208h are routed between ink feed slots 1704 and 1706 and four data lines 208a, 208c, 208e and 208g are routed between ink feed slots 1706 and 1708, as opposed to routing all eight data lines 208a-208h between the ink feed slots 1704 and 1706, and ink feed slots 1706 and 1708. The size of printhead die 1700 is reduced by routing four data lines instead of eight data lines 208a-208h.

In one embodiment, printhead die 1700 includes 600 drop generators 60. Each of the six fire groups 1702a-1702f includes 100 drop generators 60. Six data line groups in each of the fire groups 1702a-1702f include 13 drop generators 60 and two of the data line groups in each of the fire groups 1702a-1702f include 11 drop generators 60. In other embodiments, printhead die 1700 can include any suitable number of drop generators 60, such as 400 drop generators 60 or more than 600 drop generators 60. In addition, printhead die 1700 can include any suitable number of fire groups, data line groups and drop generators 60 in each fire group and data line group. Further, the printhead die may include a fewer or greater number of fluid feed sources.

Figure 22:
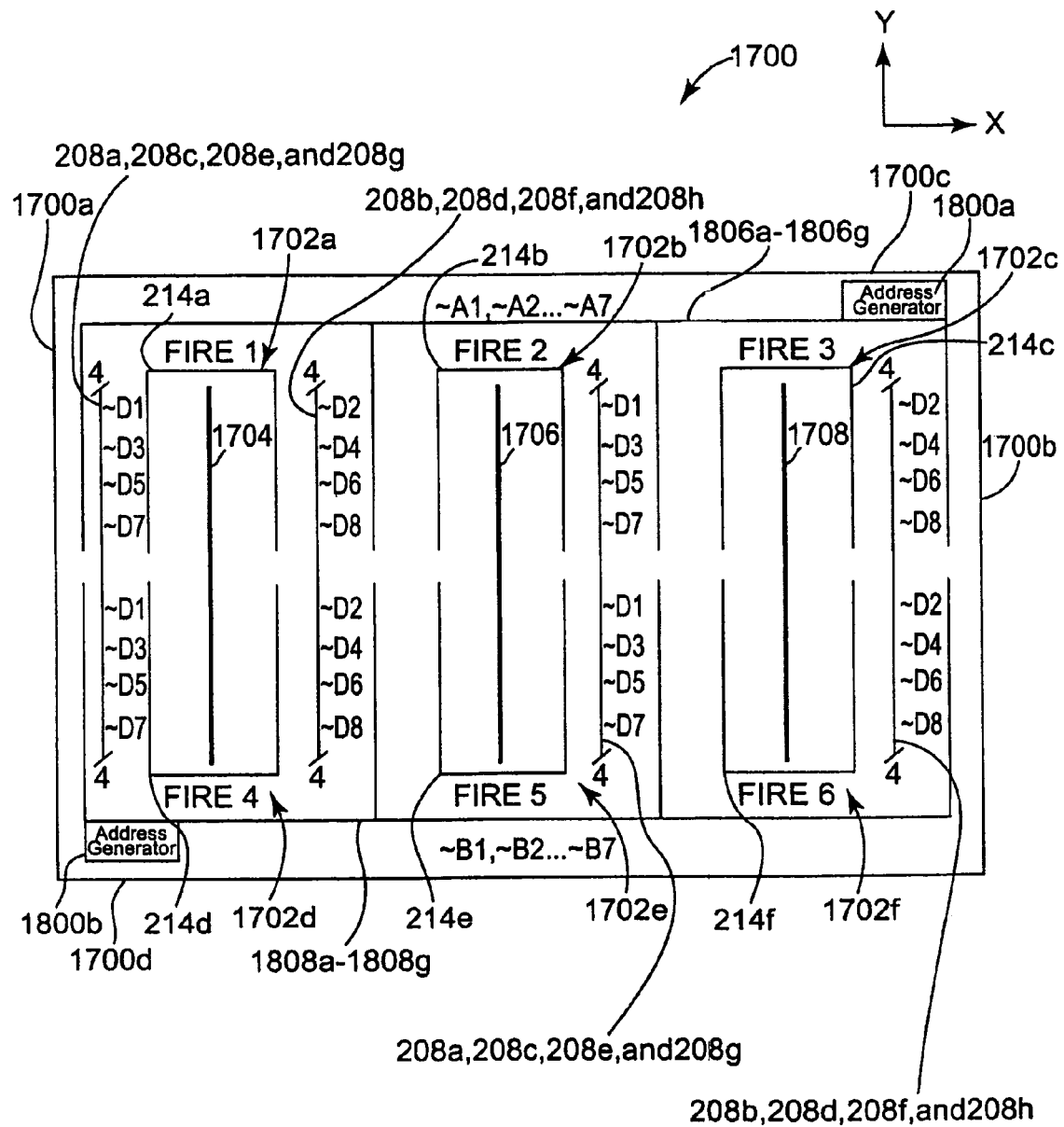
FIG. 22 is a diagram illustrating another aspect of the example layout of one embodiment of a printhead die.

FIG. 22 is a diagram illustrating another aspect of the example layout of one embodiment of printhead die 1700. The printhead die 1700 includes data lines 208a-208h, fire lines 214a-214f, ink feed sources, e.g. ink feed slots 1704, 1706 and 1708 and the six fire groups 1702a-1702f. In addition, printhead die 1700 includes address generators 1800a and 1800b and two sets of address lines 1806a-1806g and 1808a-1808g. Address generator 1800a is electrically coupled to address lines 1806a-1806g, and address generator 1800b is electrically coupled to address lines 1808a-1808g. Address lines 1806a-1806g are electrically coupled to pre-charged firing cells 120 in row subgroups in fire groups 1702a-1702c, and address lines 1808a-1808g are electrically coupled to pre-charged firing cells 120 in row subgroups in fire groups 1702d-1702f. The address lines 1806a-1806g and 1808a-1808g are electrically coupled to pre-charged firing cells 120 in row subgroups as previously described for address lines 206a-206g, respectively.

The address generators 1800a and 1800b are similar to address generators 1000 and 1002 illustrated in FIG. 13. Accordingly, suitable embodiments of address generators 1800a and 1800b can be implemented as illustrated in FIGS. 9-12.

The address generators 1800a and 1800b supply address signals ~A1, ~A2...~A7 and ~B1, ~B2...~B7 to fire groups 1702a-1702f through address lines 1806a-1806g and 1808a-1808g. Address generator 1800a supplies address signals ~A1,...~A2...~A7 to fire groups 1702a-1702c through address lines 1806a-1806g. Address generator 1800b supplies address signals ~B1, ~B2...~B7 to fire groups 1702d-1702f through address lines 1808a-1808g. The address signals ~A1, ~A2...~A7 are supplied by address generator 1800a to fire groups 1702a-1702c as the select signals SEL1, SEL2 and SEL3 are provided on select lines 212a-212c. The address signals ~B1, ~B2...~B7 are supplied by address generator 1800b to fire groups 1702d-1702f as the select signals SEL4, SEL5 and SEL6 are provided on select lines 212d-212f. In one cycle through fire groups 1702a-1702f, address generator 1800a supplies address signals ~A1, ~A2...~A7 to half the fire groups 1702a-1702c and address generator 1800b supplies address signals ~B1, ~B2...~B7 to the other half of the fire groups 1702d-1702f. In one embodiment, the address generators 1800a and 1800b are synchronized to provide the same address on address lines 1806a-1806g and 1808a-1808g during one cycle through fire groups 1702a-1702f. After each cycle through fire groups 1702a-1702f, the address generators 1800a and 1800b change address signals ~A1, ~A2...~A7 and ~B1, ~B2...~B7 to address the next sequential row subgroup in the sequence of thirteen row subgroups.

The address generators 1800a and 1800b are located in opposite corners of printhead die 1700. Address generator 1800a is located in the corner bounded by printhead die sides 1700b and 1700c. Address generator 1800b is located in the corner bounded by printhead die sides 1700a and 1700d.

The seven address lines 1806a-1806g are routed between ink feed slot 1708 and printhead die side 1700b, and along printhead die side 1700c to between ink feed slot 1704 and printhead die side 1700a. In addition, address lines 1806a-1806g are routed between ink feed slots 1704 and 1706, and between ink feed slots 1706 and 1708. The address lines 1806a-1806g are routed along one half of the length of ink feed slots 1704, 1706 and 1708 to electrically couple with pre-charged firing cells 120 in fire groups 1702a-1702c. The layout of address generators 1800a and 1800b may vary, and may be utilized to increase the frequency of operation by reducing the length of the signal paths to the pre-charged firing cells 120.

The seven address lines 1808a-1808g are routed between ink feed slot 1704 and printhead die side 1700a, and along printhead die side 1700d to between ink feed slot 1708 and printhead die side 1700b. In addition, address lines 1808a-1808g are routed between ink feed slots 1704 and 1706, and between ink feed slots 1706 and 1708. The address lines 1808a-1808g are routed along the other half of the length of ink feed slots 1704, 1706 and 1708 to electrically couple with pre-charged firing cells 120 in fire groups 1702d-1702f.

Data lines 208a, 208c, 208e and 208g are routed between printhead die side 1700a and ink feed slot 1704 and between ink feed slots 1706 and 1708. Each of the data lines 208a, 208c, 208e and 208g that are routed between printhead die side 1700a and ink feed slot 1704 is electrically coupled to pre-charged firing cells 120 in two fire groups 1702a and 1702d. Each of the data lines 208a, 208c, 208e and 208g that are routed between ink feed slots 1706 and 1708 is electrically coupled to pre-charged firing cells 120 in four fire groups 1702b, 1702c, 1702e and 1702f. Data line 208a is electrically coupled to pre-charged firing cells 120 in data line group D1 at 1710 to provide data signal ~D1. Data line 208c is electrically coupled to pre-charged firing cells 120 in data line group D3 at 1714 to provide data signal ~D3. Data line 208e is electrically coupled to pre-charged firing cells 120 in data line group D5 at 1718 to provide data signal ~D5, and data line 208g is electrically coupled to pre-charged firing cells 120 in data line group D7 at 1722 to provide data signal ~D7. The data lines 208a, 208c, 208e and 208g receive data signals ~D1, ~D3, ~D5 and ~D7 and provide the data signals ~D1, ~D3, ~D5 and ~D7 to pre-charged firing cells 120 in each of the fire groups 1702a-1702f. In one embodiment, data lines 208a, 208c, 208e and 208g are not routed the entire length of ink feed slots 1704, 1706 and 1708. Instead, each of the data lines 208a, 208c, 208e and 208g is routed to its respective data line group from a bond pad located along the side of printhead die 1700 nearest the data line group in the fire groups 1702a-1702f. Data lines 208a and 208c are electrically coupled to a bond pad along side 1700c of printhead die 1700, and data lines 208e and 208g are electrically coupled to a bond pad along side 1700d of printhead die 1700.

Data lines 208b, 208d, 208f and 208h are routed between ink feed slots 1704 and 1706 and between ink feed slot 1708 and printhead die side 1700b. Each of the data lines 208b, 208d, 208f and 208h that are routed between ink feed slots 1704 and 1706 is electrically coupled to pre-charged firing cells 120 in four fire groups 1702a, 1702b, 1702d and 1702e. Each of the data lines 208b, 208d, 208f and 208h that are routed between ink feed slot 1708 and printhead die side 1700b is electrically coupled to pre-charged firing cells 120 in two fire groups 1702c and 1702f. Data line 208b is electrically coupled to pre-charged firing cells 120 in data line group D2 at 1712 to provide data signal ~D2. Data line 208d is electrically coupled to pre-charged firing cells 120 in data line group D4 at 1716 to provide data signal ~D4. Data line 208f is electrically coupled to pre-charged firing cells 120 in data line group D6 at 1720 to provide data signal ~D6, and data line 208h is electrically coupled to pre-charged firing cells 120 in data line group D8 at 1724 to provide data signal ~D8. The data lines 208b, 208d, 208f and 208h receive data signals ~D2, ~D4, ~D6 and ~D8 and provide the data signals ~D2, ~D4, ~D6 and ~D8 to pre-charged firing cells 120 in each of the fire groups 1702a-1702f. In one embodiment, the data lines 208b, 208d, 208f and 208h are not routed the entire length of ink feed slots 1704, 1706 and 1708. Instead, each of the data lines 208b, 208d, 208f and 208h is routed to its respective data line group from a bond pad located along the side of printhead die 1700 nearest the data line group in fire groups 1702a-1702f. Data line 208b and 208d are electrically coupled to a bond pad along side 1700c of printhead die 1700, and data lines 208f and 208h are electrically coupled to a bond pad along side 1700d of printhead die 1700.

The conductive fire lines 214a-214f are located along ink feed slots 1704, 1706 and 1708 to supply energy signals FIRE1, FIRE2 . . . FIRE6 to the fire groups 1702a-1702f, respectively. The fire lines 214a-214f supply energy to firing resistors 52 in conducting pre-charged firing cells 120 to heat and eject ink from drop generators 60. To uniformly eject ink from each drop generator 60 in a fire group 1702a-1702f, the corresponding fire line 214a-214f is configured to uniformly supply energy to each firing resistor 52 in the fire group 1702a-1702f.

Energy variation is the maximum percent difference in power dissipated through any two firing resistors 52 in one of the fire groups 1702a-1702f. The highest amount of power is found in the first firing resistor 52 of a fire group 1702a-1702f, the firing resistor 52 nearest the bond pad receiving the energy signal FIRE1, FIRE2 . . . FIRE6, as only a single firing resistor 52 is energized. The lowest amount of power is found in the last firing resistor 52 of a fire group 1702a-1702f as all firing resistors 52 in a row subgroup are energized. Layout contributions to energy variation include fire line width, ground line width, metal thickness and the length of the fire line 214a-214f. Energy variations of 10 to 15 percent are preferred and energy variations up to 20 percent have been found to be suitable energy variations.

Fire groups 1702a-1702f and fire lines 214a-214f are laid out along ink feed slots 1704, 1706 and 1708 to achieve a suitable energy variation. The pre-charged firing cells 120 in a fire group 1702a-1702f are located along opposing sides of an ink feed slot 1704, 1706 or 1708. Instead of having all pre-charged firing cells 120 in a fire group 1702a-1702f along the entire length of one side of an ink feed slot 1704, 1706 or 1708, the pre-charged firing cells 120 in a fire group 1702a-1702f are located along half of the length of each of the opposing sides of an ink feed slot 1704, 1706 or 1708. The length of the corresponding fire line 214a-214f is reduced to half the length of an ink feed slot 1704, 1706 or 1708 from one end of the ink feed slot 1704, 1706 and 1708, as compared to the entire length of an ink feed slot 1704, 1706 and 1708. Each of the fire lines 214a-214f are disposed on both sides of an ink feed slot 1704, 1706 or 1708 and electrically coupled at one end of the ink feed slot 1704, 1706 or 1708 to form a substantially U-shaped fire line 214a-214f. The substantially U-shaped fire lines 214a-214f are effectively half the length of a fire line that extends the entire length of an ink feed slot 1704, 1706 and 1708. The table below compares energy variation for substantially U-shaped fire lines 214a-214f with that of linear fire lines, that is, fire lines that run the entire length of one side of an ink feed slot 1704, 1706 and 1708.

| Row | Fire group shape | Fire line width | Gnd line width | Die width | Metal thickness | % evar |
|---|---|---|---|---|---|---|
| A | Substantially U-shaped | 250 um | 115 um | 4200 um | 360 nm | 11% |
| B | Linear | 250 um | 115 um | 4200 um | 360 nm | 52% |
| C | Linear | 250 um | 115 um | 4200 um | 1440 nm (4x thick) | 36% |
| D | Linear | 750 um | 615 um | ~7200 um | 360 nm | 11% |
| E | Linear | 515 um | 380 um | ~5790 um | 1140 nm (4x thick) | 11% |

As shown in the table, using a linear fire group with the same fire line, ground line and die width results in a larger and unsuitable energy variation (11 percent verses 52 percent). The energy variation difference is improved slightly by increasing metal thickness by four times to reduce fire line resistance. However, the energy variation is still unsuitable (11 percent verses 36 percent). Alternatively, to reduce the energy variation to 11 percent in a linear fire group arrangement, the die width is increased.

The substantially U-shaped fire lines 214a-214f are electrically coupled to pre-charged firing cells 120 located along each of the opposing sides of ink feed slots 1704, 1706 and 1708. Fire line 214a is electrically coupled to each of the pre-charged firing cells 120 in FG1 at 1702a. The fire line 214a is disposed along each of the opposing sides of ink feed slot 1704 and extends from one end of ink feed slot 1704 to half the length of ink feed slot 1704 in the y-direction. The fire line 214a supplies energy signal FIRE1 and energy pulses to FG1 at 1702a.

Fire line 214b is electrically coupled to each of the pre-charged firing cells 120 in FG2 at 1702b. The fire line 214b is disposed along each of the opposing sides of ink feed slot 1706 and extends from one end of ink feed slot 1706 to half the length of ink feed slot 1706 in the y-direction. The fire line 214b supplies energy signal FIRE2 and energy pulses to FG2 at 1702b.

Fire line 214c is electrically coupled to each of the pre-charged firing cells 120 in FG3 at 1702c. The fire line 214c is disposed along each of the opposing sides of ink feed slot 1708 and extends from one end of ink feed slot 1708 to half the length of ink feed slot 1708 in the y-direction. The fire line 214c supplies the energy signal FIRE3 and energy pulses to FG3 at 1702c.

Fire line 214d is electrically coupled to each of the pre-charged firing cells 120 in FG4 at 1702d. The fire line 214d is disposed along each of the opposing sides of ink feed slot 1704 and extends from one end of ink feed slot 1704 to half the length of ink feed slot 1704 in the y-direction. The fire line 214*d* supplies the energy signal FIRE4 and energy pulses to FG4 at 1702*d*.

Fire line 214*e* is electrically coupled to each of the pre-charged firing cells 120 in FG5 at 1702*e*. The fire line 214*e* is disposed along each of the opposing sides of ink feed slot 1706 and extends from one end of ink feed slot 1706 to half the length of ink feed slot 1706 in the y-direction. The fire line 214*e* supplies the energy signal FIRE5 and energy pulses to FG5 at 1702*e*.

Fire line 214*f* is electrically coupled to each of the pre-charged firing cells 120 in FG6 at 1702*f*. The fire line 214*f* is disposed along each of the opposing sides of ink feed slot 1708 and extends from one end of ink feed slot 1708 to half the length of ink feed slot 1708 in the y-direction. The fire line 214*f* supplies the energy signal FIRE6 and energy pulses to FG6 at 1702*f*.

Figure 23:
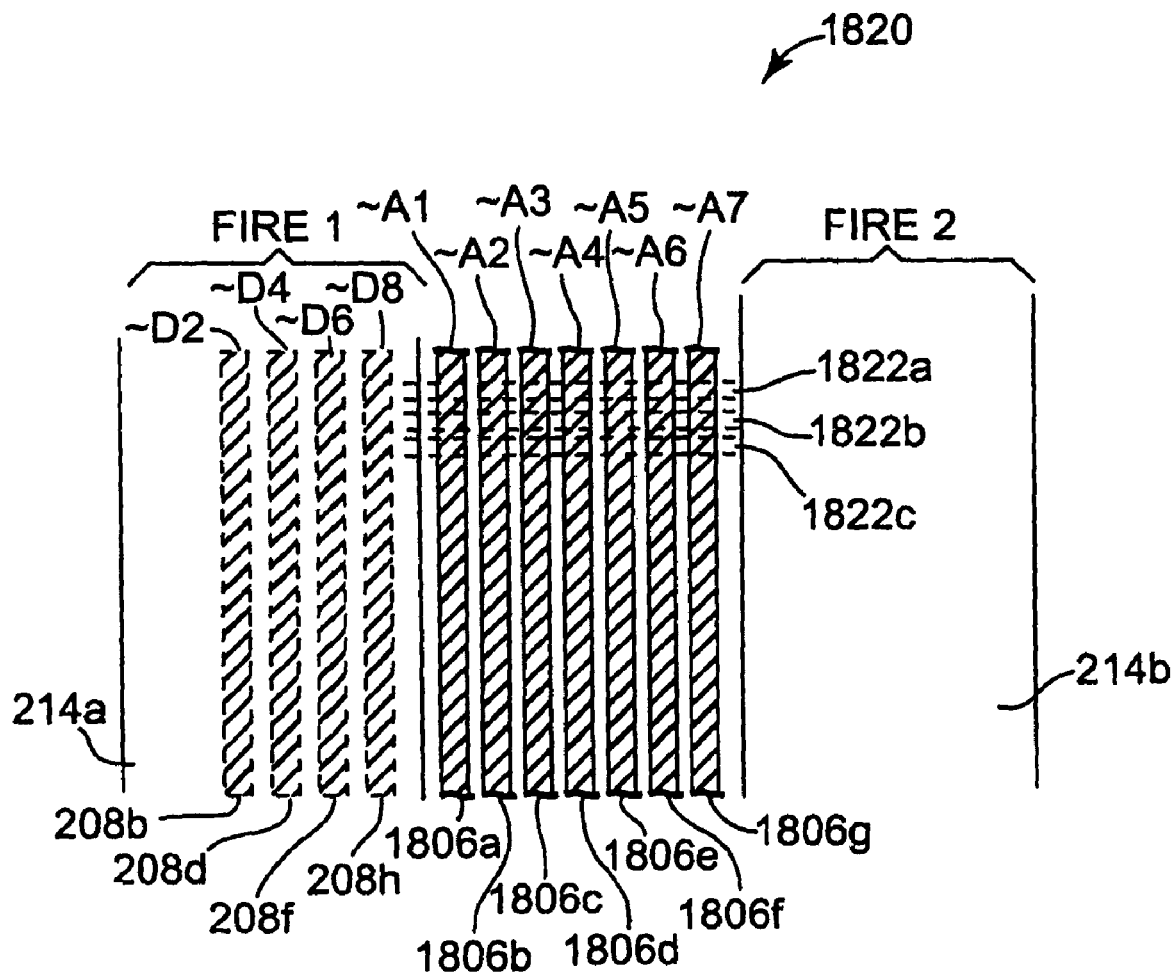
FIG. 23 is a diagram illustrating a plan view of a section of one embodiment of a printhead die.

FIG. 23 is a diagram illustrating a plan view of a section 1820 of one embodiment of printhead die 1700. The section 1820 is located in the channel between ink feed slots 1704 and 1706, and adjacent data line groups D6 at 1720*a* and 1720*b*. The section 1820 includes address lines 1806*a*-1806*g*, fire lines 214*a* and 214*b* and data lines 208*b*, 208*d*, 208*f* and 208*h*. In addition, section 1820 includes cross-connection lines 1822*a*-1822*c*. The address lines 1806*a*-1806*g*, data lines 208*b*, 208*d*, 208*f* and 208*h* and fire lines 214*a* and 214*b* are disposed parallel to each other and parallel to the length of ink feed slots 1704 and 1706. The cross-connection lines 1822*a*-1822*c* are disposed orthogonal to ink feed slots 1704 and 1706.

The address lines 1806*a*-1806*g* and data lines 208*b*, 208*d*, 208*f* and 208*h* are conductive lines formed as part of first layer metal. The fire lines 214*a* and 214*b* are conductive lines formed as part of second layer metal and cross-connection lines 1822*a*-1822*c* are formed as part of polysilicon. The polysilicon layer is insulated from the first layer metal by a first insulating layer. The first layer metal is separated and insulated from the second layer metal by a second insulating layer.

The address lines 1806*a*-1806*g* are disposed between fire lines 214*a* and 214*b*, such that address lines 1806*a*-1806*g* and fire lines 214*a* and 214*b* do not overlap. Overlapping substantially all of address lines 1806*a*-1806*g* and fire lines 214*a* and 214*b* along the length of ink feed slots 1704 and 1706 is minimized to reduce cross-talk between fire lines 214*a* and 214*b* and address lines 1806*a*-1806*g*, as compared to the cross-talk between overlapping fire lines 214*a* and 214*b* and address lines 1806*a*-1806*g*. The data lines 208*b*, 208*d*, 208*f* and 208*h* and fire lines 214*a* and 214*b* overlap along the length of ink feed slots 1704 and 1706.

The address lines 1806*a*-1806*g* receive address signals ~A1, ~A2, . . . ~A7 from onboard address generator 1800*a* and data lines 208*b*, 208*d*, 208*f* and 208*h* receive data signals ~D2, ~D4, ~D6 and ~D8 from external circuitry. The cross-connection lines 1822*a*-1822*c* are electrically coupled to selected data lines 208*b*, 208*d*, 208*f* and 208*h* or selected address lines 1806*a*-1806*g* through vias between the polysilicon layer and first layer metal. The cross-connection lines 1822*a*-1822*c* receive and supply signals across the channel between ink feed slots 1704 and 1706, to the individual pre-charged firing cells 120. The fire lines 214*a* and 214*b* receive fire signals FIRE1 and FIRE2 from external circuitry.

The routing scheme in section 1820 is used between ink feed slots 1704 and 1706, between ink feed slots 1706 and 1708, between ink feed slot 1704 and one side 1700*a* of printhead die 1700, and between ink feed slot 1708 and the other side 1700*b* of printhead die 1700.

Figure 24:
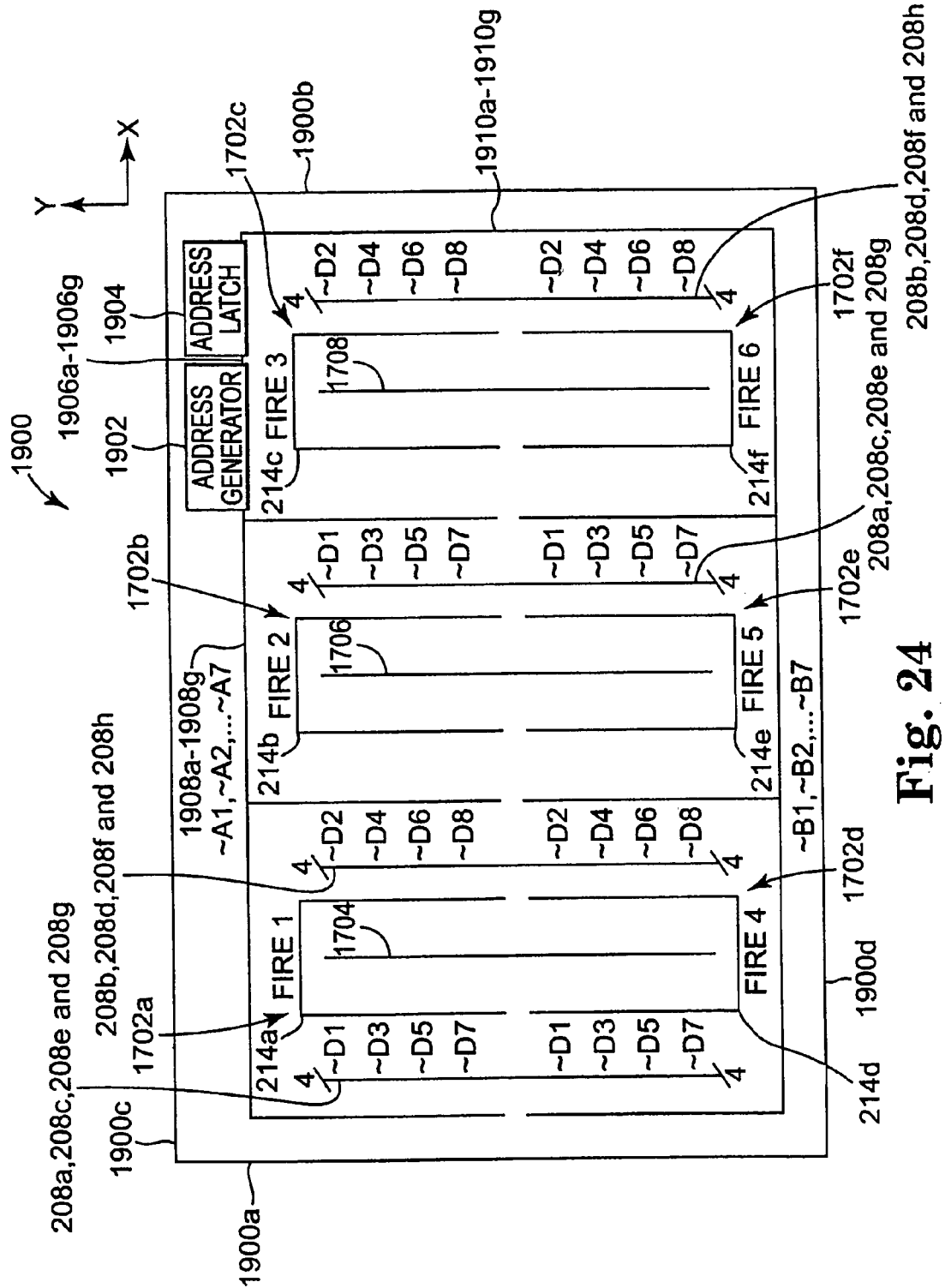
FIG. 24 is a diagram illustrating an example layout of another embodiment of a printhead die.

FIG. 24 is a diagram illustrating an example layout of one embodiment of a printhead die 1900. The printhead die 1900 includes components that are similar to components in printhead die 1700 and similar numbers are used for similar components. The printhead die 1900 includes data lines 208*a*-208*h*, fire lines 214*a*-214*f*, ink feed slots 1704, 1706 and 1708, and the six fire groups, indicated at 1702*a*-1702*f*. In addition, printhead die 1900 includes address generator 1902, address latch 1904, address lines 1908*a*-1908*g* and latched address lines 1910*a*-1910*g*. Address generator 1902 is electrically coupled to address lines 1908*a*-1908*g* and address latch 1904 is electrically coupled to latched address lines 1910*a*-1910*g*. In addition, address generator 1902 is electrically coupled to address latch 1904 through interconnect lines 1906*a*-1906*g*.

One embodiment of address generator 1902 is similar to address generator 1200 shown in FIG. 15. Accordingly, a suitable embodiment of address generator 1902 can be implemented as illustrated in FIGS. 9-12.

Address latch 1904 is one embodiment of an address generator and may be utilized in lieu of a second address generator on printhead die 1900. While address generator 1902 generates addresses based on all external signals (e.g., CSYNC and Timing Signals T1-T6), address latch 1904 generates addresses based on a received internal address provided by address generator 1902 and on external timing signals. A suitable embodiment of address latch 1904 is similar to latch circuit 1202, shown in FIG. 15, which includes seven latch registers, such as latch register 1220, illustrated in FIGS. 16 and 17.

Address lines 1908*a*-1908*g* are electrically coupled to pre-charged firing cells 120 in fire groups 1702*a*, 1702*b* and a first part of fire group 1702*c*. Latched address lines 1910*a*-1910*g* are electrically coupled to pre-charged firing cells 120 in fire groups 1702*d*-1702*f* and a second part of fire group 1702*c*. The first part of fire group 1702*c* is disposed between ink feed slot 1706 and ink feed slot 1708 and includes data line groups D1, D3, D5 and D7 at 1710*c*, 1714*c*, 1718*c* and 1722*c*. The second part of fire group 1702*c* is disposed between ink feed slot 1708 and printhead die side 1900*b* and includes data line groups D2, D4, D6 and D8 at 1712*c*, 1716*c*, 1720*c* and 1724*c*. The first part of fire group 1702*c* includes half of the pre-charged firing cells 120 in fire group 1702*c* and the second part of fire group 1702*c* includes the other half of the pre-charged firing cells 120 in fire group 1702*c*. The address lines 1908*a*-1908*g* and latched address lines 1910*a*-1910*g* are electrically coupled to row subgroups as previously described for address lines 206*a*-206*g*, respectfully. That is, address line 1908*a*/1910*a* is electrically coupled to row subgroups as address line 206*a* is coupled to row subgroups, address line 1908*b*/1910*b* is electrically coupled to row subgroups as address line 206*b* is coupled to row subgroups and so on, up to and including address line 1908*g*/1910*g* being electrically coupled to row subgroups as address line 206*g* is coupled to row subgroups.

The address generator 1902 supplies address signals ~A1, ~A2, . . . ~A7 to address latch 1904 and to fire groups 1702*a*, 1702*b* and the first part of fire group 1702*c*. Address generator 1902 supplies address signals ~A1, ~A2, . . . ~A7 to address latch 1904 through interconnect lines 1906*a*-1906*g* and to fire groups 1702*a*, 1702*b* and the first part of fire group 1702*c* through address lines 1908*a*-1908*g*. Address signal ~A1 is supplied on interconnect line 1906*a* and address line 1908*a*, address signal ~A2 is supplied on interconnect line 1906*b* and address line 1908b and so on, up to and including address signal ~A7 that is supplied on interconnect line 1906g and address line 1908g.

The address latch 1904 receives address signals ~A1, ~A2, . . . ~A7 and supplies latched address signals ~B1, ~B2, . . . ~B7 to fire groups 1702d-1702f and the second part of fire group 1702c. The address latch 1904 receives address signals ~A1, ~A2, . . . ~A7 on interconnect lines 1906a-1906g. The received signals ~A1, ~A2, . . . ~A7 are latched into address latch 1904, which supplies corresponding latched address signals ~B1, ~B2, . . . ~B7. The latched address signals ~B1, ~B2, . . . ~B7 are supplied to fire groups 1702d-1702f and the second part of fire group 1702c through latched address lines 1910a-1910g.

The address latch 1904 receives address signal ~A1 on interconnect line 1906a and latches in address signal ~A1 to supply latched address signal ~B1 on latched address line 1910a. Address latch 1904 receives address signal ~A2 on interconnect line 1906b and latches in the address signal ~A2 to supply latched address signal ~B2 on latched address line 1910b, and so on, up to address latch 1904 receiving address signal ~A7 on interconnect line 1906g and latching in address signal ~A7 to supply latched address signal ~B7 on latched address line 1910g.

The address generator 1902 supplies valid address signals ~A1, ~A2, . . . ~A7 for three time periods. During these three time periods, select signals SEL1, SEL2 and SEL3 are supplied to fire groups 1702a-1702c, respectively, one select signal SEL1, SEL2 or SEL3 per time period. The address latch 1904 latches in valid address signals ~A1, ~A2, . . . ~A7 as select signal SEL1 is supplied to fire group 1702a. The outputs of the address latch 1904 settle to valid latched address signals ~B1, ~B2, . . . ~B7 as select signal SEL2 is supplied to fire group 1702b. Valid address signals ~A1, ~A2, . . . ~A7 and valid latched address signals ~B1, ~B2, . . . ~B7 are supplied to fire group 1702c as select signal SEL3 is supplied to fire group 1702c. The address latch 1904 supplies valid latched address signals ~B1, ~B2, . . . ~B7 for four time periods. During these four time periods, select signals SEL3, SEL4, SEL5 and SEL6 are supplied to fire groups 1702c-1702f, respectively, one select signal SEL3, SEL4, SEL5 or SEL6 per time period.

The address generator 1902 changes address signals ~A1, ~A2, . . . ~A7 to address the next row subgroup of the thirteen row subgroups after the time period including select signal SEL3. The new address signals ~A1, ~A2, . . . ~A7 are valid before the beginning of the next cycle and the time period including select signal SEL1. The address latch 1904 latches in the new address signals ~A1, ~A2, . . . ~A7 after the time period including select signal SEL6. The latched address signals ~B1, ~B2, . . . ~B7 are valid during the next cycle before the time period including select signal SEL3.

In one cycle through fire groups 1702a-1702f, address generator 1902 supplies address signals ~A1, ~A2, . . . ~A7 to fire groups 1702a, 1702b and the first part of 1702c as select signals SEL1, SEL2 and SEL3 are supplied to fire groups 1702a, 1702b and 1702c. Also, latched address signals ~B1, ~B2, . . . ~B7 are supplied to the second part of fire group 1702c and fire groups 1702d-1702f as select signals SEL3, SEL4, SEL5 and SEL6 are supplied to fire groups 1702c-1702f. The address generator 1902 and address latch 1904 supply the same address on address lines 1908a-1908g and latched address lines 1910a-1910g during one cycle through fire groups 1702a-1702f.

The address generator 1902 is disposed adjacent address latch 1904 in one corner of printhead die 1900 bounded by printhead die side 1900b and printhead die side 1900c. With address generator 1902 and address latch 1904 adjacent one another, the reliability of passing address signals ~A1, ~A2, . . . ~A7 from address generator 1902 to address latch 1904 is improved as compared to passing address signals ~A1, ~A2, . . . ~A7 through longer interconnect lines 1906a-1906g.

In other embodiments, address generator 1902 and address latch 1904 can be disposed in different locations on printhead die 1900. In one embodiment, address generator 1902 can be disposed in the corner of printhead die 1900 bounded by printhead die side 1900b and printhead die side 1900c, and address latch 1904 can be disposed between fire groups 1702c and 1702f along printhead die side 1900b. In this embodiment, interconnect lines 1906a-1906g are used to supply address signals ~A1, ~A2, . . . ~A7 to the second part of fire group 1702c between ink feed slot 1708 and printhead die side 1900b. The address generator 1902 supplies address signals ~A1, ~A2, . . . ~A7 to three fire groups 1702a-1702c and address latch 1904 supplies latched address signals ~B1, ~B2, . . . ~B7 to three fire groups 1702d-1702f.

In the example embodiment, the seven address lines 1908a-1908g are routed along printhead die side 1900c to between ink feed slot 1704 and printhead die side 1900a. In addition, address lines 1908a-1908g are routed between ink feed slots 1704 and 1706, and between ink feed slots 1706 and 1708. The address lines 1908a-1908g are routed along one half of the length of ink feed slots 1704, 1706 and 1708 to electrically couple with pre-charged firing cells 120 in fire groups 1702a, 1702b and the first part of fire group 1702c.

The seven latched address lines 1910a-1910g are routed along the entire length of ink feed slot 1708 between ink feed slot 1708 and printhead die side 1900b. The latched address lines 1910a-1910g are also routed along printhead die side 1900d to between ink feed slot 1704 and printhead die side 1900a. In addition, address lines 1910a-1910g are routed between ink feed slots 1704 and 1706, and between ink feed slots 1706 and 1708. The address lines 1910a-1910g are routed along the entire length of ink feed slot 1708 between ink feed slot 1708 and printhead die side 1900b and along the other half of the lengths of ink feed slots 1704, 1706 and 1708 to electrically couple with pre-charged firing cells 120 in the second part of fire group 1702c and fire groups 1702d, 1702e and 1702f.

Data lines 208a, 208c, 208e and 208g are routed between printhead die side 1900a and ink feed slot 1704 and between ink feed slots 1706 and 1708. Each of the data lines 208a, 208c, 208e and 208g routed between printhead die side 1900a and ink feed slot 1704 is electrically coupled to pre-charged firing cells 120 in two fire groups 1702a and 1702d. Each of the data lines 208a, 208c, 208e and 208g routed between ink feed slots 1706 and 1708 is electrically coupled to pre-charged firing cells 120 in four fire groups 1702b, 1702c, 1702e and 1702f. Data line 208a is electrically coupled to pre-charged firing cells 120 in data line group D1 at 1710 to supply data signal ~D1. Data line 208c is electrically coupled to pre-charged firing cells 120 in data line group D3 at 1714 to supply data signal ~D3. Data line 208e is electrically coupled to pre-charged firing cells 120 in data line group D5 at 1718 to supply data signal ~D5, and data line 208g is electrically coupled to pre-charged firing cells 120 in data line group D7 at 1722 to supply data signal ~D7. The data lines 208a, 208c, 208e and 208g receive data signals ~D1, ~D3, ~D5 and ~D7 and supply data signals ~D1, ~D3, ~D5 and ~D7 to pre-charged firing cells 120 in each of the fire groups 1702a-1702f. In one embodiment, data lines 208a, 208c, 208e and 208g are not routed the entire length of ink feed slots 1704, 1706 and 1708. Instead, each of the data lines 208a, 208c, 208e and 208g is routed to its respective data line group from a bond pad located along the side of printhead die 1900 nearest the data line group in fire groups 1702a-1702f. Data lines 208a and 208c are electrically coupled to a bond pad along side 1900c of printhead die 1900, and data lines 208e and 208f are electrically coupled to a bond pad along side 1900d of printhead die 1900.

Data lines 208b, 208d, 208f and 208h are routed between ink feed slots 1704 and 1706 and between ink feed slot 1708 and printhead die side 1900b. Each of the data lines 208b, 208d, 208f and 208h routed between ink feed slots 1704 and 1706 is electrically coupled to pre-charged firing cells 120 in four fire groups 1702a, 1702b, 1702d and 1702e. Each of the data lines 208b, 208d, 208f and 208h routed between ink feed slot 1708 and printhead die side 1900b is electrically coupled to pre-charged firing cells 120 in two fire groups 1702c and 1702f. Data line 208b is electrically coupled to pre-charged firing cells 120 in data line group D2 at 1712 to supply data signal ~D2. Data line 208d is electrically coupled to pre-charged firing cells 120 in data line group D4 at 1716 to supply data signal ~D4. Data line 208f is electrically coupled to pre-charged firing cells 120 in data line group D6 at 1720 to supply data signal ~D6, and data line 208h is electrically coupled to pre-charged firing cells 120 in data line group D8 at 1724 to supply data signal ~D8. The data lines 208b, 208d, 208f and 208h receive data signals ~D2, ~D4, ~D6 and ~D8 and supply the data signals ~D2, ~D4, ~D6 and ~D8 to pre-charged firing cells 120 in each of the fire groups 1702a-1702f. In one embodiment, the data lines 208b, 208d, 208f and 208h are not routed the entire length of ink feed slots 1704, 1706 and 1708. Instead, each of the data lines 208b, 208d, 208f and 208h is routed to its respective data line group from a bond pad located along the side of printhead die 1900 nearest the data line group in fire groups 1702a-1702f. Data line 208b and 208d are electrically coupled to a bond pad along side 1900c of printhead die 1900, and data lines 208f and 208h are electrically coupled to a bond pad along side 1900d of printhead die 1900.

The conductive fire lines 214a-214f are located along ink feed slots 1704, 1706 and 1708 to supply energy signals FIRE1, FIRE2 . . . FIRE6 to fire groups 1702a-1702f, respectively. The fire lines 214a-214f supply energy to firing resistors 52 in conducting pre-charged firing cells 120 to heat and eject ink from drop generators 60. To uniformly eject ink from each drop generator 60 in a fire group 1702a-1702f, the corresponding fire line 214a-214f is configured to uniformly supply energy to each firing resistor 52 in the fire group 1702a-1702f.

Energy variation is the maximum percent difference in power dissipated through any two firing resistors 52 in one of the fire groups 1702a-1702f. The highest amount of power is found in the first firing resistor 52 of a fire group 1702a-1702f as only a single firing resistor 52 is energized, where the first firing resistor 52 is the firing resistor 52 nearest the bond pad receiving the energy signal FIRE1, FIRE2 . . . FIRE6. The lowest amount of power is found in the last firing resistor 52 of a fire group 1702a-1702f as all firing resistors 52 in a row subgroup are energized. Layout contributions to energy variation include fire line width, ground line width, metal thickness and the length of the fire line 214a-214f. Energy variations of 10 to 15 percent are preferred and energy variations up to 20 percent have been found to be suitable energy variations.

Fire groups 1702a-1702f and fire lines 214a-214f are laid out along ink feed slots 1704, 1706 and 1708 to achieve a suitable energy variation. The pre-charged firing cells 120 in a fire group 1702a-1702f are located along opposing sides of an ink feed slot 1704, 1706 or 1708. Instead of having all pre-charged firing cells 120 in a fire group 1702a-1702f along the entire length of one side of an ink feed slot 1704, 1706 or 1708, the pre-charged firing cells 120 in a fire group 1702a-1702f are located along half of the length of each of the opposing sides of an ink feed slot 1704, 1706 or 1708. The length of the corresponding fire line 214a-214f is reduced to half the length of an ink feed slot 1704, 1706 or 1708 from one end of the ink feed slot 1704, 1706 and 1708, as compared to the entire length of an ink feed slot 1704, 1706 and 1708. Each of the fire lines 214a-214f are disposed on both sides of an ink feed slot 1704, 1706 or 1708 and electrically coupled at one end of the ink feed slot 1704, 1706 or 1708 to form a substantially U-shaped fire line 214a-214f. The substantially U-shaped fire lines 214a-214f are effectively half the length of a fire line that extends the entire length of an ink feed slot 1704, 1706 and 1708. The table below compares energy variation for substantially U-shaped fire lines 214a-214f with that of linear fire lines, that is, fire lines that run the entire length of one side of an ink feed slot 1704, 1706 and 1708.

| Row | Fire group shape | Fire width | Gnd width | Die width | Metal thickness | % evar |
| --- | --- | --- | --- | --- | --- | --- |
| A | Substantially U-shaped | 250 um | 115 um | 4200 um | 360 nm | 11% |
| B | Linear | 250 um | 115 um | 4200 um | 360 nm | 52% |
| C | Linear | 250 um | 115 um | 4200 um | 1440 nm (4x thick) | 36% |
| D | Linear | 750 um | 615 um | ~7200 um | 360 nm | 11% |
| E | Linear | 515 um | 380 um | ~5790 um | 1140 nm (4x thick) | 11% |

As shown in the table, using a linear fire group with the same fire line, ground line and die width results in a larger and unsuitable energy variation (11 percent verses 52 percent). The energy variation difference is improved slightly by increasing metal thickness by four times to reduce fire line resistance. However, the energy variation is still unsuitable (11 percent verses 36 percent). Alternatively, to reduce the energy variation to 11 percent in a linear fire group arrangement, the die width is increased.

The substantially u-shaped fire lines 214a-214f are electrically coupled to pre-charged firing cells 120 disposed along each of the opposing sides of ink feed slots 1704, 1706 and 1708. Fire line 214a is electrically coupled to each of the pre-charged firing cells 120 in FG1 at 1702a. The fire line 214a is disposed along each of the opposing sides of ink feed slot 1704 and extends from one end of ink feed slot 1704 to half the length of ink feed slot 1704 in the y-direction. The fire line 214a supplies energy signal FIRE1 and energy pulses to FG1 at 1702a.

Fire line 214b is electrically coupled to each of the pre-charged firing cells 120 in FG2 at 1702b. The fire line 214b is disposed along each of the opposing sides of ink feed slot 1706 and extends from one end of ink feed slot 1706 to half the length of ink feed slot 1706 in the y-direction. The fire line 214b supplies energy signal FIRE2 and energy pulses to FG2 at 1702b.

Fire line 214c is electrically coupled to each of the pre-charged firing cells 120 in FG3 at 1702c. The fire line 214c is disposed along each of the opposing sides of ink feed slot 1708 and extends from one end of ink feed slot 1708 to half the length of ink feed slot 1708 in the y-direction. The fire line 214c supplies the energy signal FIRE3 and energy pulses to FG3 at 1702c.

Fire line 214d is electrically coupled to each of the pre-charged firing cells 120 in FG4 at 1702d. The fire line 214d is disposed along each of the opposing sides of ink feed slot 1704 and extends from one end of ink feed slot 1704 to half the length of ink feed slot 1704 in the y-direction. The fire line 214d supplies the energy signal FIRE4 and energy pulses to FG4 at 1702d.

Fire line 214e is electrically coupled to each of the pre-charged firing cells 120 in FG5 at 1702e. The fire line 214e is disposed along each of the opposing sides of ink feed slot 1706 and extends from one end of ink feed slot 1706 to half the length of ink feed slot 1706 in the y-direction. The fire line 214e supplies the energy signal FIRE5 and energy pulses to FG5 at 1702e.

Fire line 214f is electrically coupled to each of the pre-charged firing cells 120 in FG6 at 1702f. The fire line 214f is disposed along each of the opposing sides of ink feed slot 1708 and extends from one end of ink feed slot 1708 to half the length of ink feed slot 1708 in the y-direction. The fire line 214f supplies the energy signal FIRE6 and energy pulses to FG6 at 1702f.

While FIGS. 21 through 24 depict layouts that show address generators and/or an address latch on the printhead die, the address signals may be provided from an external source as well. Where the address signals are provided from an external source, address generators and/or address latches need not be provided on the printhead die. In this case, the layouts described in FIGS. 21 through 24 may be exactly the same.

Figure 25A:
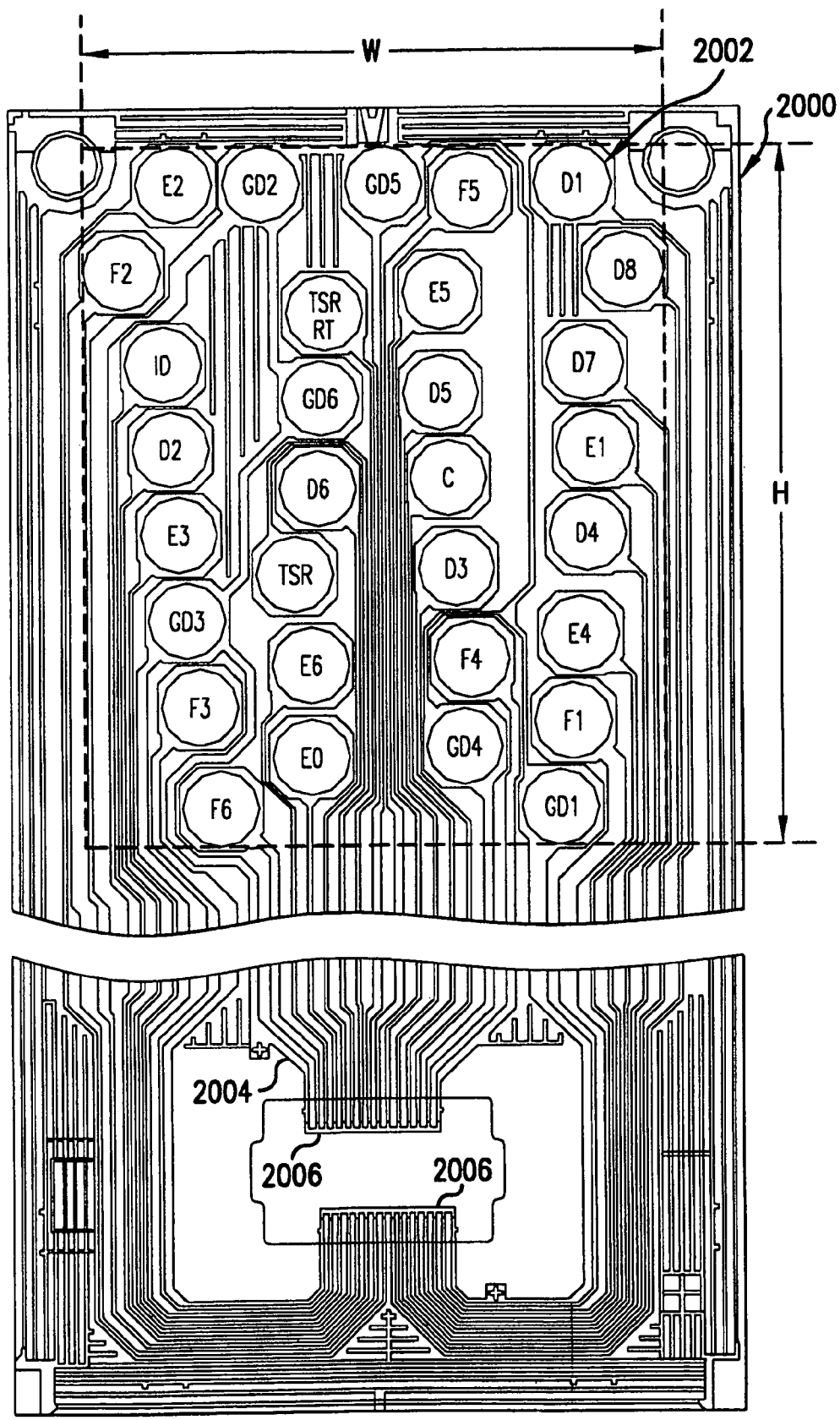
FIGS. 25A and 25B are diagrams illustrating contact areas of a flex circuit that may be utilized to couple external circuitry to a printhead die.
Figure 25B:
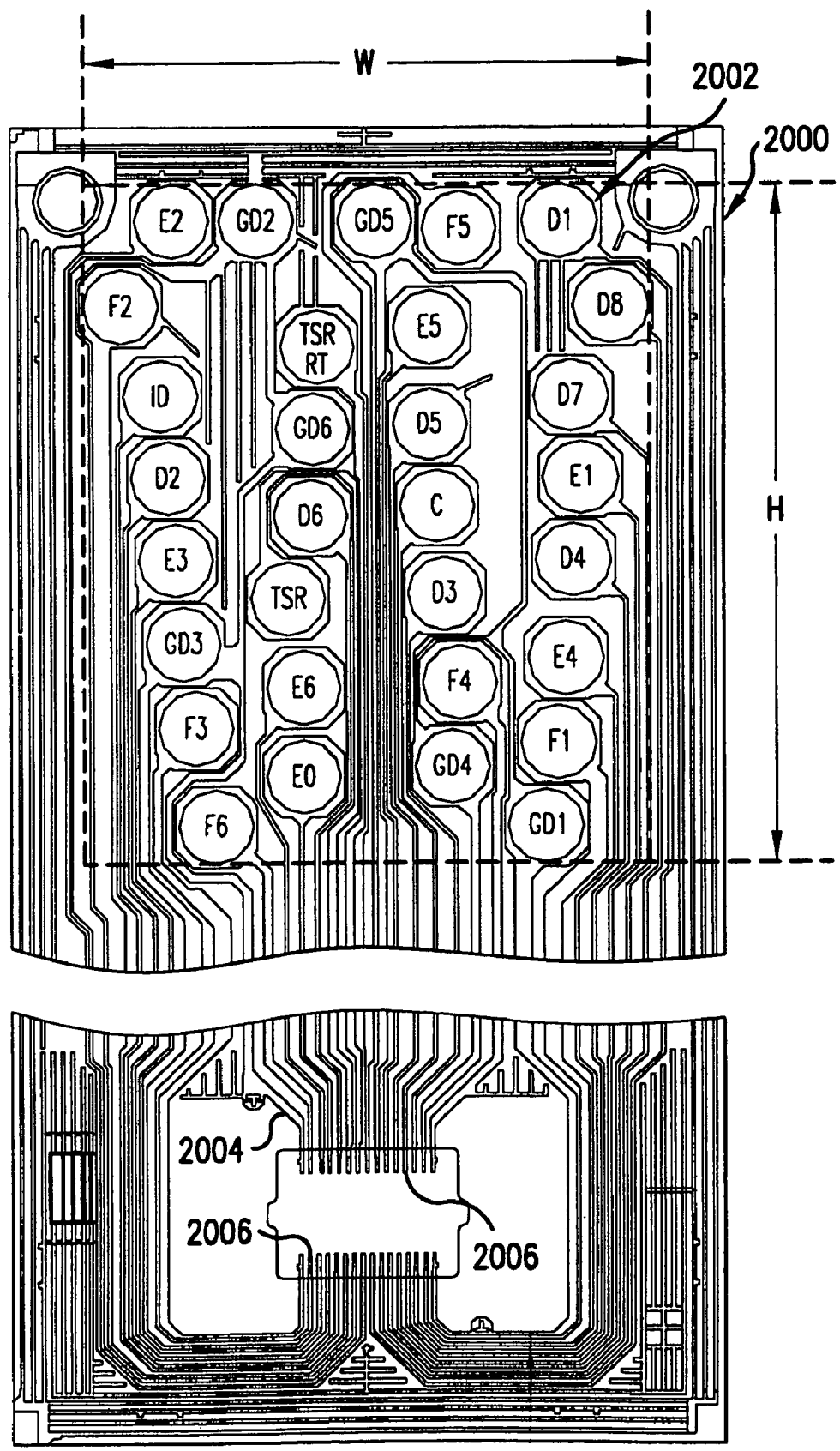

Referring to FIGS. 25A and 25B, diagrams illustrating contact areas 2000 of a flex circuit 2002 that may be utilized to couple external circuitry to a printhead die 40 are illustrated. The contact areas 2000 are electrically coupled via conductive paths 2004 to contacts 2006 which provide coupling to the printhead die.

Enable line contact areas E0-E6 are configured to receive enable signals from an external source and to provide the enable signals, e.g. select signals SEL1-SEL6, precharge signals PRE1-PRE6, and the LATCH signal. However, it should be noted that the relationship between the lines described with respect to FIGS. 4-8 and 11-24 and the contact areas E0-E6 need not be one to one, e.g. signal PRE1 need not be provided at contact area E0. All that is required is that appropriate select lines and precharge lines are coupled to the appropriate enable contact areas.

Data line contact areas D1-D8 are configured to receive signals which provide print data representative of an image to be printed and to provide data signals D1-D8 respectively, to the individual data line groups, e.g. data line groups D1-D8. Fire line contact areas F1-F6 configured to receive energy pulses and to provide the energy signals along fire lines Fire1-Fire6 to the appropriate fire groups, e.g. fire groups 202a-202f and 1702a-1702f. Ground line contact areas GD1-GD6 are configured provide a return path for signals that are conducted by the firing resistors from the fire groups, e.g. fire groups 202a-202f or fire groups 1702a-1702f. Control signal contact area C is configured to receive a signal for controlling the internal operation of the printhead die, e.g. the CSYNC signal.

Temperature sense resistor contact area TSR allows a printer coupled to an ink jet cartridge to determine a temperature of the printhead die, based upon a measurement of the resistor. A temperature sense resistor return contact area TSR-RT provides a return path for signals provided at temperature sense resistor contact area TSR.

An identification bit contact area ID is coupled to identification circuitry on printhead die that allows a printer to determine the operating parameters of the printhead die and print cartridge.

In one embodiment, an electrical path between contact areas 2000 and the pre-charged firing cells 120 comprises conductive paths 2004, contacts 2006, and the appropriate signal lines, e.g. data lines 208a-208h, pre-charge lines 210a-210f, select lines 212a-212f, or ground lines. It should be noted that pre-charge lines 210a-210f and select lines 212a-212f may be coupled to enable line contact areas E0-E6.

It should be noted that in certain embodiments the high voltage levels discussed herein are at or above approximately 4.0 volts, while the low voltage levels discussed herein are at or below approximately 1.0 volts. Other embodiments may use different voltage levels than the previously described levels.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A fluid ejection device, comprising:
a first fire line adapted to receive a first energy signal having energy pulses;
a first address generator configured to provide first address signals;
first resistors electrically coupled to the first fire line and to receive at least some of the first address signals, the first resistors configured to conduct in response to the first energy signal to eject fluid based on the first address signals and data signals indicative of image data;
a second fire line adapted to receive a second energy signal having energy pulses;
a second address generator configured to provide second address signals;
second resistors electrically coupled to the second fire line and to receive the second address signals, the second resistors configured to conduct in response to the second energy signal to eject fluid based on the second address signals and the data signals indicative of the image data; and
a direction signal coupled to the first and second address generators that operates a shift register of the generators in a forward or a reverse direction.

2. The fluid ejection device of claim 1, wherein the first address generator is configured to generate the first address signals based on timing signals received by the fluid ejection device and the second address generator is configured to generate the second address signals based on the timing signals.

3. The fluid ejection device of claim 2, comprising a control line adapted to receive a control signal having control pulses, wherein each of the control pulses coincide with a pulse of the timing signals to control operation of the first and second address generators.

4. The fluid ejection device of claim 1, wherein the first address generator provides valid first address signals for three of six pulses in a repeating series of six pulses and the second address generator provides valid second address signals for another three of the six pulses in the repeating series of six pulses.

5. The fluid ejection device of claim 4, wherein the valid first address signals and the valid second address signals reference the same address during one cycle through the repeating series of six pulses.

6. The fluid ejection device of claim 1, comprising:
a latch configured to receive first address signals and provide latched address signals based upon the first address signals; and
second resistors configured to eject fluid based on the latched address signals.

7. The fluid ejection device of claim 6, comprising signal lines adapted to receive timing signals that provide a repeating series of pulses, wherein each of the signal lines is adapted to receive a different one of a repeating series of pulses.

8. The fluid ejection device of claim 7, comprising a control line adapted to receive a control signal having control pulses that coincide with at least one of the pulses in the repeating series of pulses and to conduct the control pulses to the first address generator.

9. The fluid ejection device of claim 1, wherein the shift register is configured to provide output signals, and wherein at least one of the first address generator and the second address generator comprises:
logic configured to receive the output signals and provide the corresponding one of the first address signals or the second address signals in response to the output signals.

10. A printhead die comprising:
a first line adapted to conduct first pulses;
a second line adapted to conduct second pulses;
a controller including
a shift register configured to provide at least one of a set of output signals, and
switches configured so that at least two of the switches receive a predetermined one of the output signals and each of the at least two switches provides a different one of a set of address signals;
a first group of resistors coupled to conduct based upon a first at least two signals of the set of address signals and the first pulses; and
a second group of resistors coupled to conduct based upon a second at least two signals of the set of address signals and the second pulses, wherein the first at least two signals and the second at least two signals each comprise at least one different signal from the other.

11. The printhead die of claim 10, wherein the controller provides the set of address signals in a predetermined pattern.

12. The printhead die of claim 11, wherein the predetermined pattern comprises sequentially providing at least two signals of the set of address signals during any time period.

13. The printhead die of claim 12, wherein the time period during which each group of at least two signals is provided has a same duration.

14. The printhead die of claim 10, wherein the set of address signals includes at least a first state and a second state, and wherein when the set of address signals are in the first state only the first group of resistors are coupled to conduct and when the set of address signals are in the second state only the second group of resistors are coupled to conduct.

15. The printhead die of claim 10, wherein the set of address signals comprises a plurality of states and wherein the states are provided in a sequence as the set of address signals by the controller.

16. The printhead die of claim 15, wherein the set of address signals are provided in a second sequence that is an inverse of the sequence, based upon a direction signal received by the controller.

17. The printhead die of claim 10,
wherein each of the at least two of the switches is a field-effect transistor,
wherein the gates of all the transistors are coupled to the predetermined one of the output signals, and
wherein the drain of each of the transistors is coupled to a different line, each different line providing one of the set of address signals.

* * * * *